US012788832B2

(12) United States Patent
Horti et al.

(10) Patent No.: US 12,788,832 B2
(45) Date of Patent: Nov. 10, 2026

(54) POSITRON EMISSION TOMOGRAPHY (PET) RADIOTRACERS FOR IMAGING MACROPHAGE COLONY-STIMULATING FACTOR 1 RECEPTOR (CSF1R) IN NEUROINFLAMMATION

(71) Applicant: The Johns Hopkins University, Baltimore, MD (US)

(72) Inventors: Andrew G. Horti, Ellicott City, MD (US); Ravi Naik, Baltimore, MD (US); Robert F. Dannals, Sparks, MD (US); Martin G. Pomper, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 17/253,336

(22) PCT Filed: Jun. 26, 2019

(86) PCT No.: PCT/US2019/039234

§ 371 (c)(1),
(2) Date: Dec. 17, 2020

(87) PCT Pub. No.: WO2020/006075

PCT Pub. Date: Jan. 2, 2020

(65) Prior Publication Data

US 2021/0290784 A1 Sep. 23, 2021

Related U.S. Application Data

(60) Provisional application No. 62/689,958, filed on Jun. 26, 2018.

(51) Int. Cl.
*A61K 51/04* (2006.01)

(52) U.S. Cl.
CPC ................................ *A61K 51/0459* (2013.01)

(58) Field of Classification Search
CPC ................................................. A61K 51/0459
USPC ....................................................... 424/1.89
See application file for complete search history.

(56) References Cited

FOREIGN PATENT DOCUMENTS

WO WO 2006/047504 5/2006
WO WO2006047504 A1 5/2006
WO WO-2017189961 A1 * 11/2017 ............ A61K 45/06

OTHER PUBLICATIONS

Frank et al. J. Label Compd Radiopharm. 2007, 50, 746-769. (Year: 2007).*
Illig et al. J. Med. Chem. 2011, 54, 7860-7883. (Year: 2011).*
Zhou et al. J. Cereb. Blood Flow Metab. 2021, 41(9) 2410-2422. (Year: 2021).*
International Search Report and Written Opinion for PCT/US2019/039234. Mailed Oct. 18, 2019. 10 pages.
Aguzzi et al., Microglia: scapegoat, saboteur, or something else? Science. Jan. 11, 2013;339(6116):156-61.
Aid et al., Neuronal overexpression of cyclooxygenase-2 does not alter the neuroinflammatory response during brain innate immune activation. Neurosci Lett. Jul. 12, 2010;478(3):113-8.
Akiyama et al., Expression of the receptor for macrophage colony stimulating factor by brain microglia and its upregulation in brains of patients with Alzheimer's disease and amyotrophic lateral sclerosis. Brain Res. Mar. 7, 1994;639(1):171-4.
Alterman et al., Colony stimulating factor-1 expression in human glioma. Mol Chem Neuropathol. Feb.-Apr. 1994;21(2-3):177-88.
Beeton et al., Induction and clinical scoring of chronic-relapsing experimental autoimmune encephalomyelitis. J Vis Exp. 2007;(5):224.
Berge et al., Pharmaceutical salts. J Pharm Sci. Jan. 1977;66(1):1-19.
Bernard-Gauthier et al., 5-(4-((4-[18F]fluorobenzyl)oxy)-3-methoxybenzyl) pyrimidine-2, 4-diamine: A selective dual inhimitor for potential PET imaging of Trk/CSF-1R. Bioorganic & Medicinal Chemistry Letters, 2014, vol. 24, No. 20. pp. 4784-4790.
Boissonneault et al., Powerful beneficial effects of macrophage colony-stimulating factor on beta-amyloid deposition and cognitive impairment in Alzheimer's disease. Brain. Apr. 2009;132(Pt 4):1078-92.
Catorce et al., LPS-induced Murine Neuroinflammation Model: Main Features and Suitability for Pre-clinical Assessment of Nutraceuticals. Curr Neuropharmacol. 2016;14(2):155-64.
Chitu et al., Emerging Roles for CSF-1 Receptor and its Ligands in the Nervous System. Trends Neurosci. Jun. 2016;39(6):378-393.
Coughlin et al., The distribution of the alpha7 nicotinic acetylcholine receptor in healthy aging: An in vivo positron emission tomography study with [ 18 F]ASEM. Neuroimage. Jan. 15, 2018;165:118-124.
Deczkowska et al., Disease-Associated Microglia: A Universal Immune Sensor of Neurodegeneration. Cell. May 17, 2018;173(5):1073-1081.
Denardo et al., Leukocyte complexity predicts breast cancer survival and functionally regulates response to chemotherapy. Cancer Discov. Jun. 2011;1(1):54-67.
Dickens et al., Detection of microglial activation in an acute model of neuroinflammation using PET and radiotracers 11C-(R)-PK11195 and 18F-GE-180. J Nucl Med. Mar. 2014;55(3):466-72.
Dobos et al., The role of indoleamine 2,3-dioxygenase in a mouse model of neuroinflammation-induced depression. J Alzheimers Dis. 2012;28(4):905-15.
El-Gamal et al., Recent Advances of Colony-Stimulating Factor-1 Receptor (CSF-1R) Kinase and Its Inhibitors. J Med Chem. Jul. 12, 2018;61(13):5450-5466.
Elmore et al., Colony-stimulating factor 1 receptor signaling is necessary for microglia viability, unmasking a microglia progenitor cell in the adult brain. Neuron. Apr. 16, 2014;82(2):380-97.

(Continued)

*Primary Examiner* — Michael G. Hartley
*Assistant Examiner* — Sean R Donohue
(74) *Attorney, Agent, or Firm* — Casimir Jones, SC; Bradley P. Loren

(57) ABSTRACT

Positron emission tomography (PET) radiotracers for imaging macrophage colony stimulating factor-1 receptors in a subject afflicted with or suspected of being afflicted with a neuroinflammatory or neurodegenerative disease or disorder are disclosed.

3 Claims, 20 Drawing Sheets

(56) References Cited

OTHER PUBLICATIONS

Foster. Developing and testing integrated multicompartment models to describe a single-input multiple-output study using the SAAM II software system. Adv Exp Med Biol. 1998;445:59-78.
Ginhoux et al., Fate mapping analysis reveals that adult microglia derive from primitive macrophages. Science. Nov. 5, 2010;330(6005):841-5.
Hannestad et al., Endotoxin-induced systemic inflammation activates microglia: [$^{11}$C]PBR28 positron emission tomography in nonhuman primates. Neuroimage. Oct. 15, 2012;63(1):232-9.
Heppner et al., Immune attack: the role of inflammation in Alzheimer disease. Nat Rev Neurosci. Jun. 2015;16(6):358-72.
Hickman et al., TREM2 and the neuroimmunology of Alzheimer's disease. Biochem Pharmacol. Apr. 15, 2014;88(4):495-8.
Horti et al., 18F-FNDP for PET Imaging of Soluble Epoxide Hydrolase. J Nucl Med. Nov. 2016;57(11):1817-1822.
Horti et al., PET imaging of microglia by targeting macrophage colony-stimulating factor 1 receptor (CSF1R). Proc Natl Acad Sci U S A. Jan. 29, 2019;116(5):1686-1691.
Illig et al., Discovery of novel FMS kinase inhibitors as anti-inflammatory agents. Bioorg Med Chem Lett. Mar. 1, 2008;18(5):1642-8.
Janssen et al., PET Imaging of Microglial Activation-Beyond Targeting TSPO. Molecules. Mar. 8, 2018;23(3):607.
Jones et al., Behavioral and pathological outcomes in MOG 35-55 experimental autoimmune encephalomyelitis. J Neuroimmunol. Aug. 13, 2008;199(1-2):83-93.
Keren-Shaul et al., A Unique Microglia Type Associated with Restricting Development of Alzheimer's Disease. Cell. Jun. 15, 2017;169(7):1276-1290.e17.
Krauser et al., Phenotypic and metabolic investigation of a CSF-1R kinase receptor inhibitor (BLZ945) and its pharmacologically active metabolite. Xenobiotica. Feb. 2015;45(2):107-23.
Lee et al., Macrophage colony-stimulating factor in human fetal astrocytes and microglia. Differential regulation by cytokines and lipopolysaccharide, and modulation of class II MHC on microglia. J Immunol. Jan. 15, 1993;150(2):594-604.
Lentz et al., Exploring the relationship of macrophage colony-stimulating factor levels on neuroaxonal metabolism and cognition during chronic human immunodeficiency virus infection. J Neurovirol. Oct. 2010;16(5):368-76.
Logan et al., Graphical analysis of reversible radioligand binding from time-activity measurements applied to [N-11C-methyl]-(-)-cocaine PET studies in human subjects. J. Cereb. Blood Flow Metab. 1990. 10(5):740-747.
Lue et al., Inflammatory repertoire of Alzheimer's disease and nondemented elderly microglia in vitro. Glia. Jul. 2001;35(1):72-9.
Masgrau et al., Should We Stop Saying 'Glia' and 'Neuroinflammation'? Trends Mol Med. Jun. 2017;23(6):486-500.
Melnikova et al., Reversible pathologic and cognitive phenotypes in an inducible model of Alzheimer-amyloidosis. J Neurosci. Feb. 27, 2013;33(9):3765-79.
Michaelson et al., CSF-1 deficiency in mice results in abnormal brain development. Development. Sep. 1996;122(9):2661-72.
Miyaura et al., Palladium-Catalyzed Cross-Coupling Reactions of Organoboron Compounds. Chem Rev. 1995, 95, 2457-2483.
Murphy et al., Expression of macrophage colony-stimulating factor receptor is increased in the AbetaPP(V717F) transgenic mouse model of Alzheimer's disease. Am J Pathol. Sep. 2000;157(3):895-904.
Naik et al., PET tracer for imaging the macrophage colony stimulating factor receptor (CSF1R) in rodent brain. Journal of Nuclear Medicine. 2018, vol. 59. Suppl 1 p. 547.
Nandi et al., The CSF-1 receptor ligands IL-34 and CSF-1 exhibit distinct developmental brain expression patterns and regulate neural progenitor cell maintenance and maturation. Dev Biol. Jul. 15, 2012;367(2):100-13.
Palle et al., Cytokine Signaling in Multiple Sclerosis and Its Therapeutic Applications. Med Sci (Basel). Oct. 13, 2017;5(4):23.
Peyraud et al., CSF-1R Inhibitor Development: Current Clinical Status. Curr Oncol Rep. Sep. 5, 2017;19(11):70.
Prieto-Morin et al., CSF1R-related leukoencephalopathy mimicking primary progressive multiple sclerosis. J Neurol. Sep. 2016;263(9):1864-5.
Qin et al., Systemic LPS causes chronic neuroinflammation and progressive neurodegeneration. Glia. Apr. 1, 2007;55(5):453-62.
Rahmim et al., Statistical dynamic image reconstruction in state-of-the-art high-resolution PET. Phys Med Biol. Oct. 21, 2005;50(20):4887-912.
Raivich et al., Regulation of MCSF receptors on microglia in the normal and injured mouse central nervous system: a quantitative immunofluorescence study using confocal laser microscopy. J Comp Neurol. Jun. 8, 1998;395(3):342-58.
Smith et al., M-CSF increases proliferation and phagocytosis while modulating receptor and transcription factor expression in adult human microglia. J Neuroinflammation. Jul. 17, 2013;10:85.
Stabin et al., OLINDA/EXM: the second-generation personal computer software for internal dose assessment in nuclear medicine. J Nucl Med. Jun. 2005;46(6):1023-7.
Stabin et al., Physical models and dose factors for use in internal dose assessment. Health Phys. Sep. 2003;85(3):294-310.
Tronel et al., Molecular Targets for PET Imaging of Activated Microglia: The Current Situation and Future Expectations. Int J Mol Sci. Apr. 11, 2017;18(4):802.
Walker et al., Studies on Colony Stimulating Factor Receptor-1 and Ligands Colony Stimulating Factor-1 and Interleukin-34 in Alzheimer's Disease Brains and Human Microglia. Front Aging Neurosci. Aug. 9, 2017;9:244.
Wall et al., Cyano-Substituted 2-Carboxyimidazoles: Synthesis of 4-Cyano-1-{[2-(tri-methylsilyl)ethoxy]methyl}-1H-imidazole-2-carboxylate Potassium Salt. Synthesis. 2008 (21), 3377-3379.
Wustrow et al., ChemInform Abstract: Coupling of Aryloboronic Acids with a Partially Reduced Pyridine Derivatives. ChemInform. 1991. 23(19):197.
Wuts et al., Greene's Protective Groups in Organic Synthesis, Fourth Edition. Wiley-Interscience, 2007. TOC only. 6 pages.
Yan et al., An intracellular protein that binds amyloid-beta peptide and mediates neurotoxicity in Alzheimer's disease. Nature. Oct. 16, 1997;389(6652):689-95.
Zhang et al., An RNA-sequencing transcriptome and splicing database of glia, neurons, and vascular cells of the cerebral cortex. J Neurosci. Sep. 3, 2014;34(36):11929-47.
Bauer et al., Synthesis and in vivo evaluation of [11C]tariquidar, a positron emission tomography radiotracer based on a third-generation P-glycoprotein inhibitor. Bioorg Med Chem. Aug. 1, 2010;18(15):5489-9.
Mathews et al., Radiosynthesis and validation of [5-cyano-N-(4-(4-[11C]methylpiperazin-1-yl)-2-(piperidin-1-yl)phenyl) furan-2-carboxamide] ([11C]CPPC), a PET radiotracer for imaging CSF1R, a microglia-specific marker. J Labelled Comp Radiopharm. Nov. 2019;62(13):903-908.
Moss et al., Glossary of class names of organic compounds and reactive intermediates based on structure (IUPAC Recommendations 1995). Pure & Applied Chemistry, Pergamon Press, Oxford, GB, Jan. 1, 1995;67(8/9):1307-1375.
Extended European Search Report for EP 19825817.0, mailed Feb. 21, 2022, 18 pages.
Illig et al., "Optimization of a Potent Class of Arylamide Colony-Stimulating Factor-1 Receptor Inhibitors Leading to Anti-inflammatory Clinical Candidate 4-Cyano-N-[2-(1-cyclohexen-1-yl)-4-[1-[(dimethylamino)-acetyl]-4-piperidinyl]phenyl]-1H-imidazole-2-carboxamide (JNJ-28312141)", J. Med Chem. 2011, 54, 7860-7883.
Bauer F. et al.,Bioorganic & Medicinal Chemistry, "Synthesis and in vivo evaluation of [11C]tariquidar, a positron emission tomography radiotracer based on a third-generation P-glycoprotein inhibitor", 2010, 18, pp. 5489-5549.
Bernard-Gauthier V. et al., Bioorganic & Medicinal Chemistry Letters, 5-(4-((4-[18F]fluorobenzyl)oxy)-3-methoxybenzyl)pyrimidine-2-4-diamine: A selective dual inhibitor for potential PET imaging of Trk/CSF-1R, 2014, 24, pp. 4784-4790.

(56) References Cited

OTHER PUBLICATIONS

Illig C. R. et al., Bioorganic & Medicinal Chemistry Letters, "Discovery of novel FMS kinase inhibitors as anti-inflammatory agents", Apr. 2008, 18, pp. 1642-1648.
Naik R. et al., "PET tracer for imaging the macrophage cology stimulating factor receptor (CSF1R) in rodent brain", Journal of Nuclear Medicine, May 1, 2018, vol. 59 (Issue supplement 1), 547, 10 pages.
Coughlin et al., First-in-human use of $^{11}$C-CPPC with positron emission tomography for imaging the macrophage colony-stimulating factor 1 receptor, EJNMMI Research (2022) 12:64, pp. 1-8.
Mills et al., Exploring [$^{11}$C]CPPC as a CSF1R-targeted PET Imaging Marker for Early Parkinson's Disease Severity, medRxiv 2023.05.28.23290647; doi: https://doi.org/10.1101/2023.05.28.23290647, 29 pages.
Eckelman W.C., et al., "Receptor-Binding Radiotracers: A Class of Potential Radiopharmaceuticals", The Journal of Nuclear Medicine, 1979, vol. 20, No. 4, pp. 350-357.
Foss C.A., et al., "A Radioligand for in Vitro Autoradiography of CSF1R in Post-mortem CNS Tissues", EJNMMI Research, 2024, vol. 14, Article No. 76, pp. 1-12.
Friden M., et al., "Identification of Positron Emission Tomography (PET) Tracer Candidates by Prediction of the Target-bound Fraction in the Brain", EJNMMI Research, 2014, vol. 4, Article No. 50, pp. 1-8.
Halldin C., et al., "Brain Radioligands—State of the Art and New Trends", The Quarterly Journal of Nuclear Medicine, 2001, vol. 45, No. 2, pp. 139-152.
Mills K.A., et al., "Exploring [11 C]CPPC as a CSF1R-Targeted PET Imaging Marker for Early Parkinson's Disease Severity", The Journal of Clinical Investigation, 2025, vol. 135, No. 12, e186591, 11 Pages.
Radchenko V., et al., "18th European Symposium on Radiopharmacy and Radiopharmaceuticals", EJNMMI Radiopharmacy and Chemistry, vol. 1 Supplementary 1, Salzburg, Austria. Apr. 7-10, 2016, Jun. 16, 2016, pp. 1-37.
Zhang L., et al., "Strategies to Facilitate the Discovery of Novel CNS PET Ligands", EJNMMI Radiopharmacy and Chemistry, 2016, 1;13, vol. 1, No. 1, pp. 1-12.

* cited by examiner

Pre-KRL

Pre-CPPC

[11C]CPPC

POSITRON EMISSION TOMOGRAPHY (PET) RADIOTRACERS FOR IMAGING MACROPHAGE COLONY-STIMULATING FACTOR 1 RECEPTOR (CSF1R) IN NEUROINFLAMMATION

FEDERALLY SPONSORED RESEARCH OR DEVELOPMENT

This invention was made with government support under AG054802 awarded by the National Institutes of Health. The government has certain rights in the invention.

BACKGROUND

Positron emission tomography (PET) is the most advanced method by which to quantify brain receptors and their occupancy by endogenous ligands or drugs in vivo. PET imaging of putative neuroinflammatory states (Masgrau R, et al. (2017)) has been attempted using radioligands that target the translocator protein (TSPO), which reports on reactive glial cells. Due to limitations of TSPO-targeted PET, including a lack of cell type specificity and sensitivity to genotype, researchers have developed PET radiotracers targeting other aspects of neuroinflammation (P2X7, COX-2, CB2, ROS, A2AR, MMP) [see Tronel C, et al. (2017): Janssen B, et al. (2018)]. Nevertheless, newer imaging targets, such as P2X7 receptor, are likewise fraught with limitations, including lack of cell-specific expression (FIG. 7). An agent that targets only reactive microglia, which represent up to 10% of cells within the brain (Aguzzi A, et al. (2013)), might provide a more specific and less ambiguous readout of neuroinflammatory states by imaging this cellular mediator of injury and repair within the CNS.

Within the brain the macrophage colony-stimulating factor 1 receptor (CSF1R) (also known as c-FMS, CD-115, or M-CSFR) is mainly expressed by microglia, while its expression in other cells including neurons is low (Akiyama H, et al. (1994); Zhang Y, et al. (2014)) (FIG. 7). CSF1R is a cell surface protein in a subfamily of tyrosine kinase receptors activated by two homodimeric ligands, CSF1 and IL-34 (Peyraud F, et al. (2017)). CSF1R is the primary regulator of the survival, proliferation, differentiation, and function of hematopoietic precursor cells (Chitu V. et al. (2016)). CSF1R directly controls the development, survival, and maintenance of microglia and plays a pivotal role in neuroinflammation (Ginhoux F, et al. (2010); Elmore M R, et al. (2014); Walker D G, et al. (2017); Smith A M, et al. (2013); Palle P, et al. (2017)). Inhibition of CSF1R has been pursued as a way to treat a variety of inflammatory and neuroinflammatory disorders (El-Gamal M I, et al. (2018)). Regional distribution of CSF1R in the healthy mammalian brain has not been studied in detail, but expression analysis in mice has demonstrated enhanced levels of CSF1R in superior cortical regions and lower levels in other regions of the brain (Lue L F, et al. (2001)).

Several reports demonstrated up-regulation of CSF1R and CSF1 in the postmortem brain in Alzheimer's disease (AD) (Akiyama H, et al. (1994). Walker D G, et al. (2017), Lue L F, et al. (2001)). Studies in mice showed moderate expression of CSF1R in control brain and high expression in microglia located near amyloid beta (AP) deposits in transgenic mouse models of AD (Murphy G M Jr, et al. (2000); Yan S D, et al. (1997); Boissonneault V, et al. (2009)). The gene encoding the cognate ligand for CSF1R, CSF1, is up-regulated in stage 2 disease-associated microglia (DAM), which may play a salutary role in keeping AD in check (Deczkowska A, et al. (2018); Keren-Shaul H, et al. (2017)). Traumatic brain injury in rodents led to a high and specific increase in CSF1R levels in injured regions (Raivich G, et al. (1998)). CSF1R is altered in lesions due to multiple sclerosis (Prieto-Morin C, et al. (2016)). Up-regulated CSF1R was demonstrated in brain tumors (Alterman R L and Stanley E R (1994)). HIV-associated cognitive impairment correlated with levels of CSF1R (Lentz M R, et al. (2010)). Clinical PET imaging of CSF1R could advance understanding of the CSF1R pathway relevant to neuroinflammation in CNS disorders and guide development of new antiinflammatory CSF1R therapies.

Suitable PET radiotracers for imaging of CSF1R are not available. The only published radiolabeled CSF1R inhibitor was synthesized in 2014 (Bernard-Gauthier V, Schirrmacher R (2014)), but imaging studies with this radiotracer have not been reported.

SUMMARY

The presently disclosed subject matter provides an imaging agent for imaging macrophage colony stimulating factor receptor (CSF1R) in a subject afflicted or suspected of being afflicted with one or more neuroinflammatory or neurodegenerative diseases or conditions.

In some aspects, the presently disclosed subject matter provides an imaging agent for imaging macrophage colony stimulating factor receptor (CSF1R) in a subject afflicted or suspected of being afflicted with one or more neuroinflammatory or neurodegenerative diseases or conditions, the imaging agent comprising a compound of formula (I):

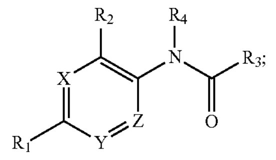

(I)

wherein:

X, Y, and Z are each independently selected from the group consisting of —N— and —$CR_5$—, wherein $R_5$ is selected from the group consisting of H, substituted or unsubstituted $C_1$-$C_8$ alkyl, or R*, wherein R* is a moiety comprising a radioisotope suitable for positron emission tomography (PET) imaging or the radioisotope itself;

$R_1$ is selected from the group consisting of substituted or unsubstituted heteroalkyl, substituted or unsubstituted heteroaryl, $C_1$-$C_8$ alkoxyl, $C_1$-$C_8$ alkylamino, $C_1$-$C_8$ dialkylamino, —N($C_1$-$C_8$ alkyl)($SO_2$)($C_1$-$C_8$ alkyl), wherein $R_1$ optionally can be substituted with R* or $R_1$ can be a radioisotope suitable for PET imaging;

$R_2$ is substituted or unsubstituted heteroalkyl, wherein $R_2$ optionally can be substituted with R*;

$R_3$ is substituted or unsubstituted heteroaryl, wherein $R_3$ optionally can be substituted with R*; and $R_4$ is selected from the group consisting of H, substituted or unsubstituted $C_1$-$C_8$ alkyl, $C_1$-$C_8$ alkoxyl, cycloalkyl, cycloheteroalkyl, aryl, and heteroaryl; or a pharmaceutically acceptable salt thereof;

wherein at least one of $R_1$, $R_2$, $R_3$ or $R_5$ is substituted with R* or is a radioisotope suitable for PET imaging.

In other aspects, the presently disclosed subject matter provides a method for imaging macrophage colony stimulating factor receptor (CSF1R) in a subject afflicted or suspected of being afflicted with one or more neuroinflammatory or neurodegenerative diseases or conditions, the method comprising administering to the subject an effective amount of an imaging agent of formula (I), or a pharmaceutically acceptable salt thereof and taking a PET image.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 3:
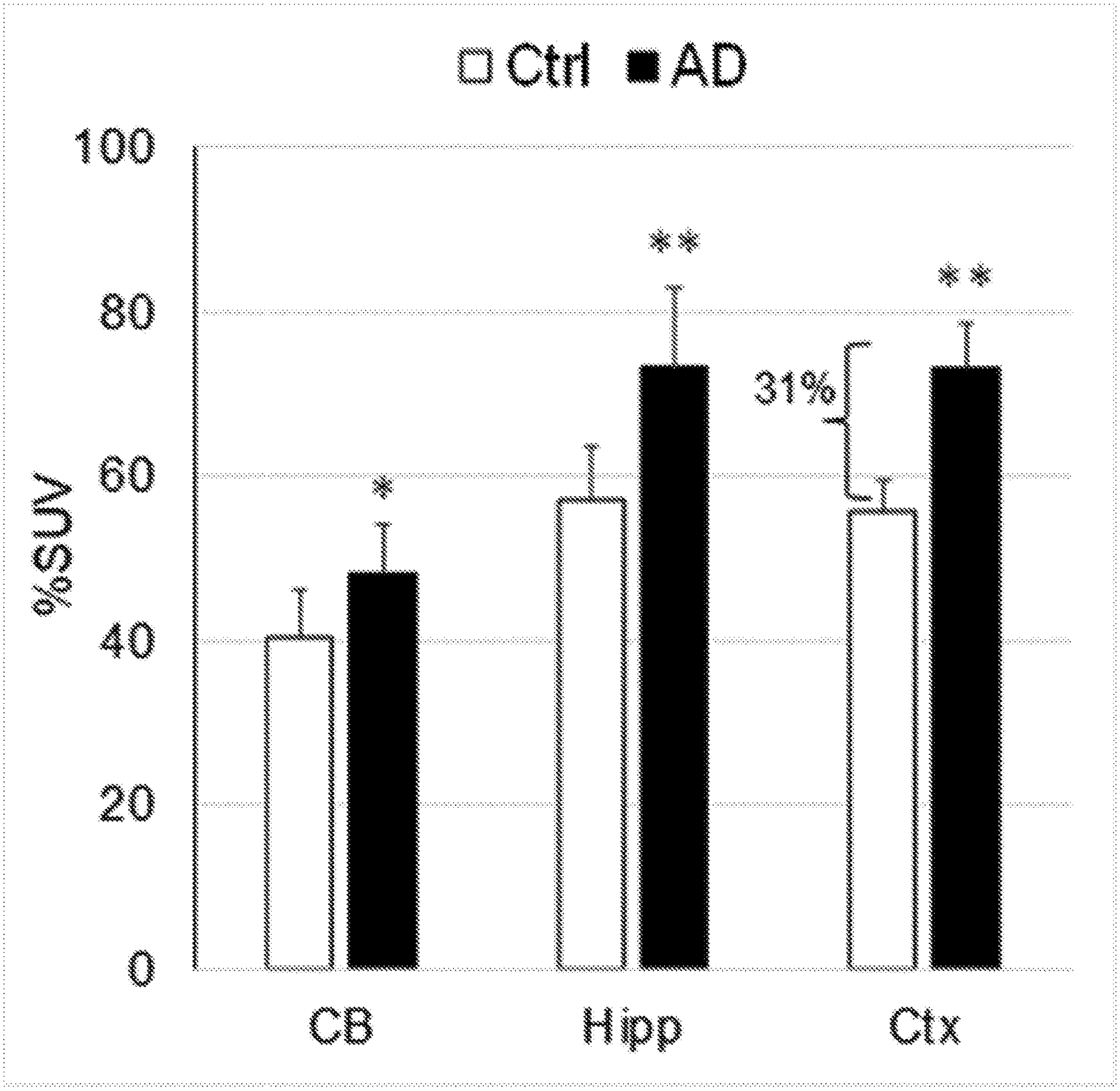
Figure 5A:
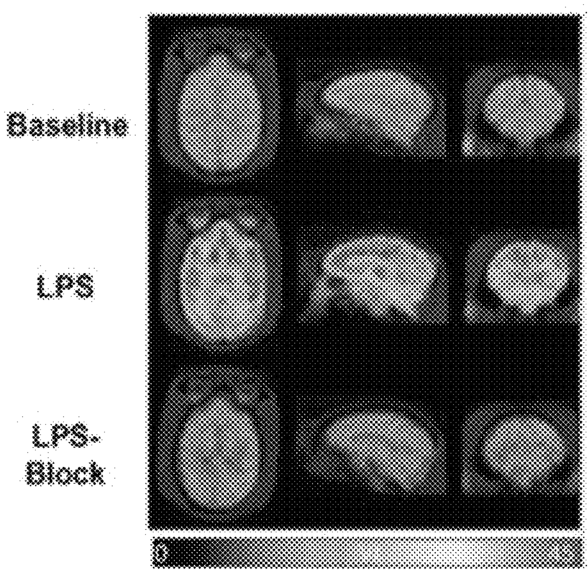
Figure 5B:
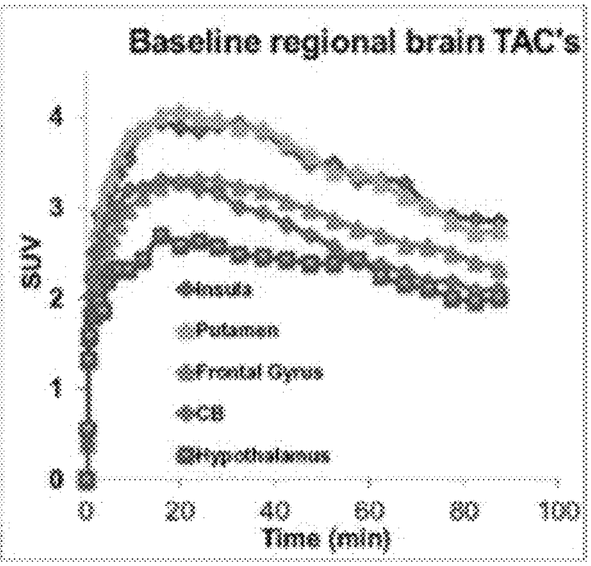
Figure 5C:
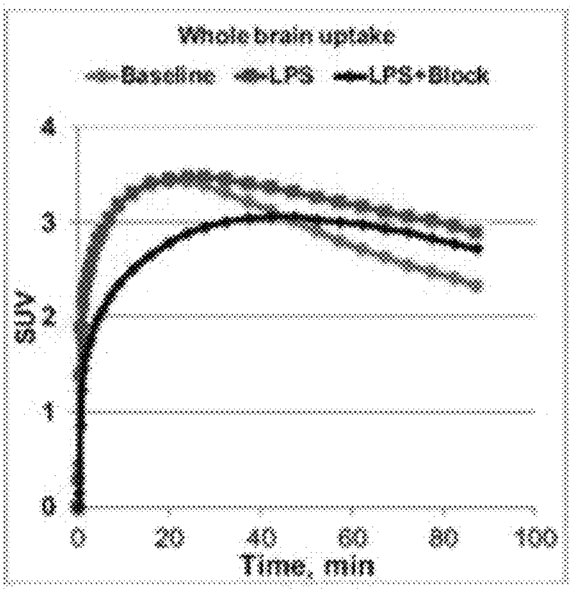
Figure 5D:
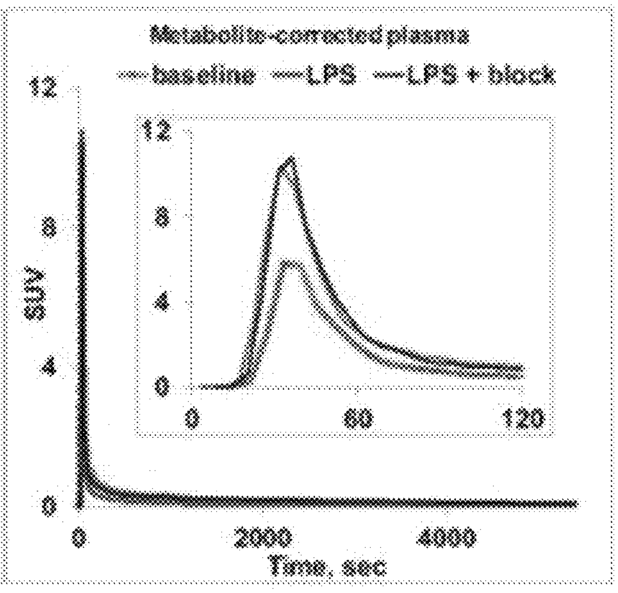
Figure 6:
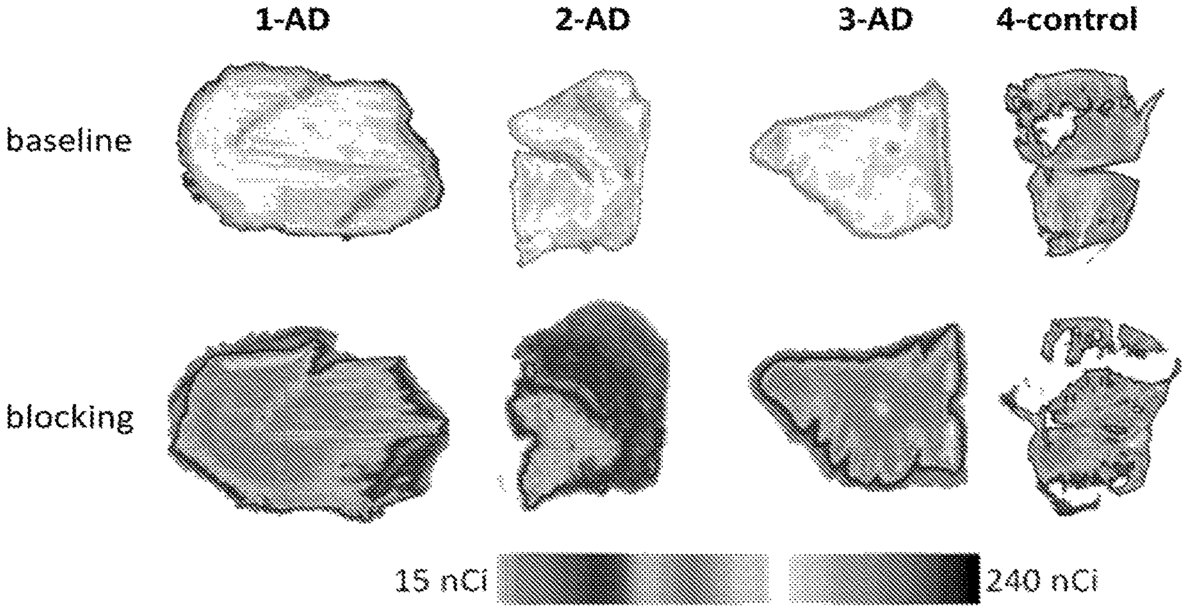
Figure 7A:
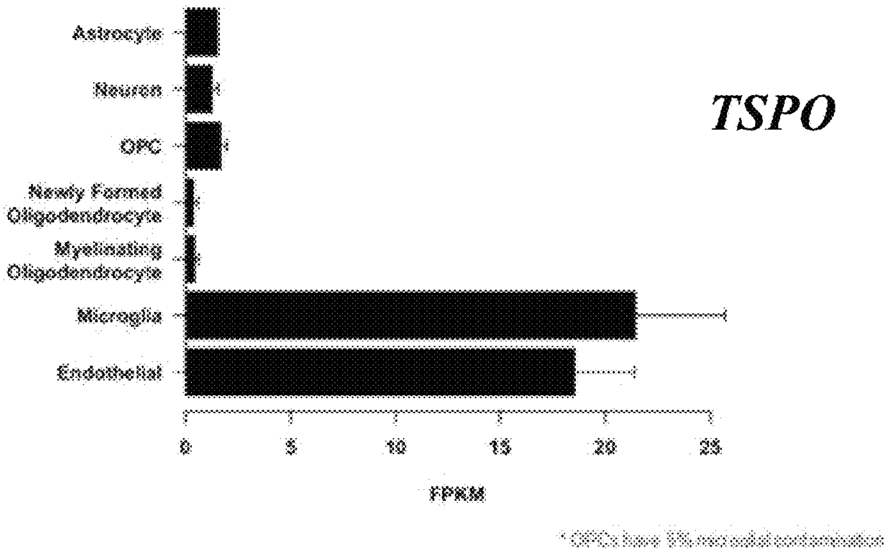
Fig. 7A (Prior Art)
Figure 7B:
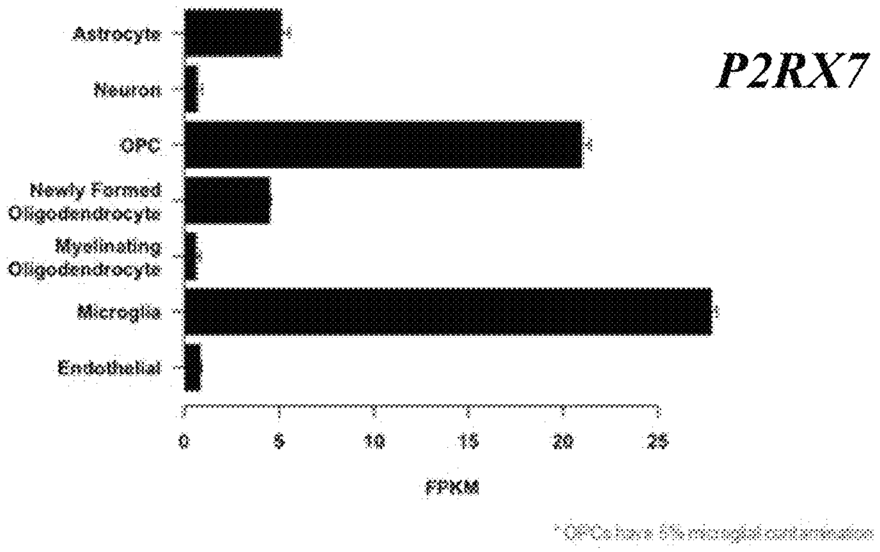
Fig. 7B (Prior Art)
Figure 7C:
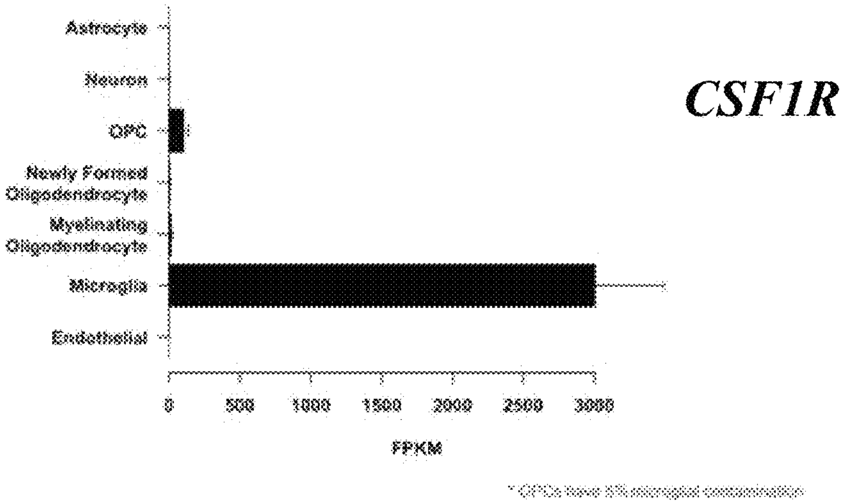
Fig. 7C (Prior Art)
Figure 8:
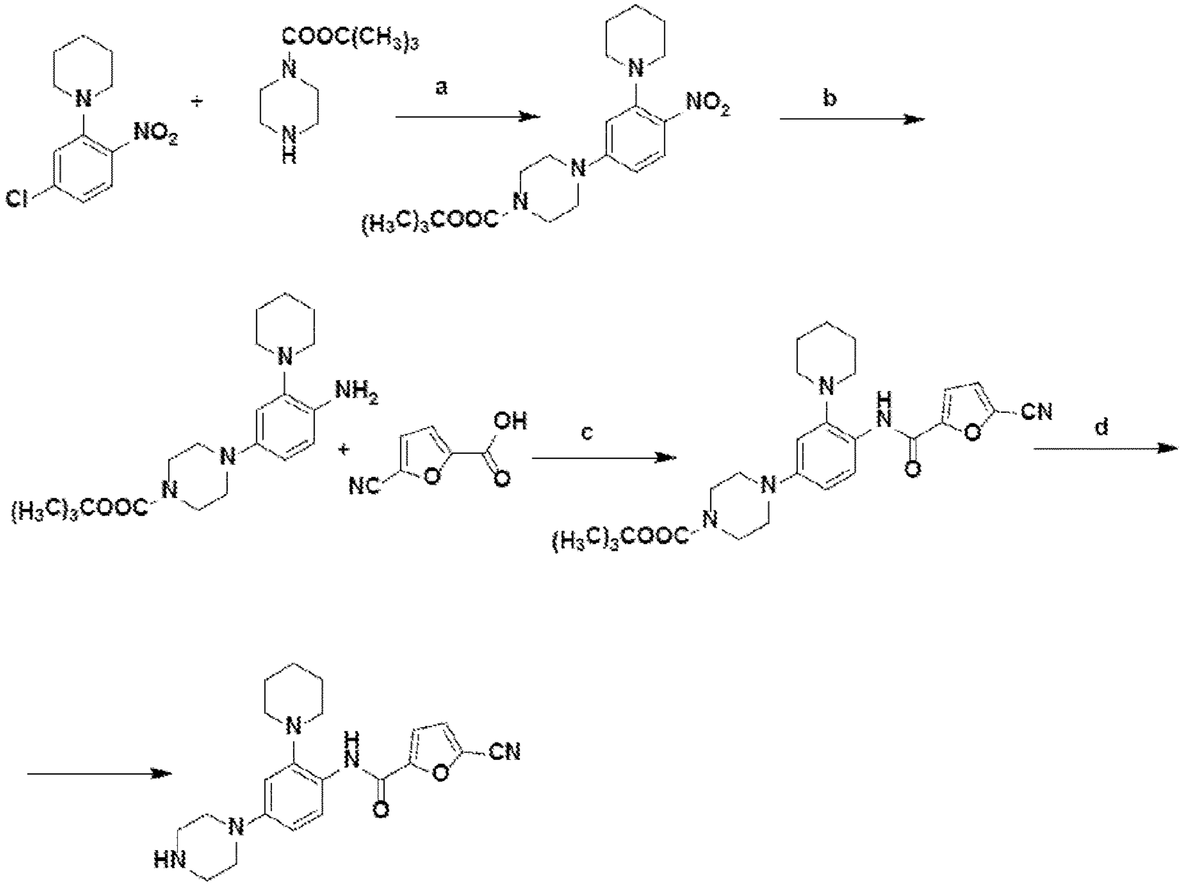
Figure 9:
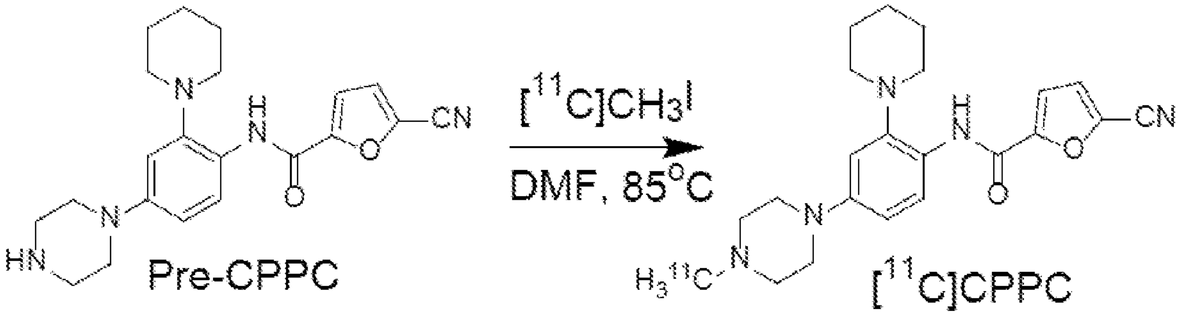
Figure 10:
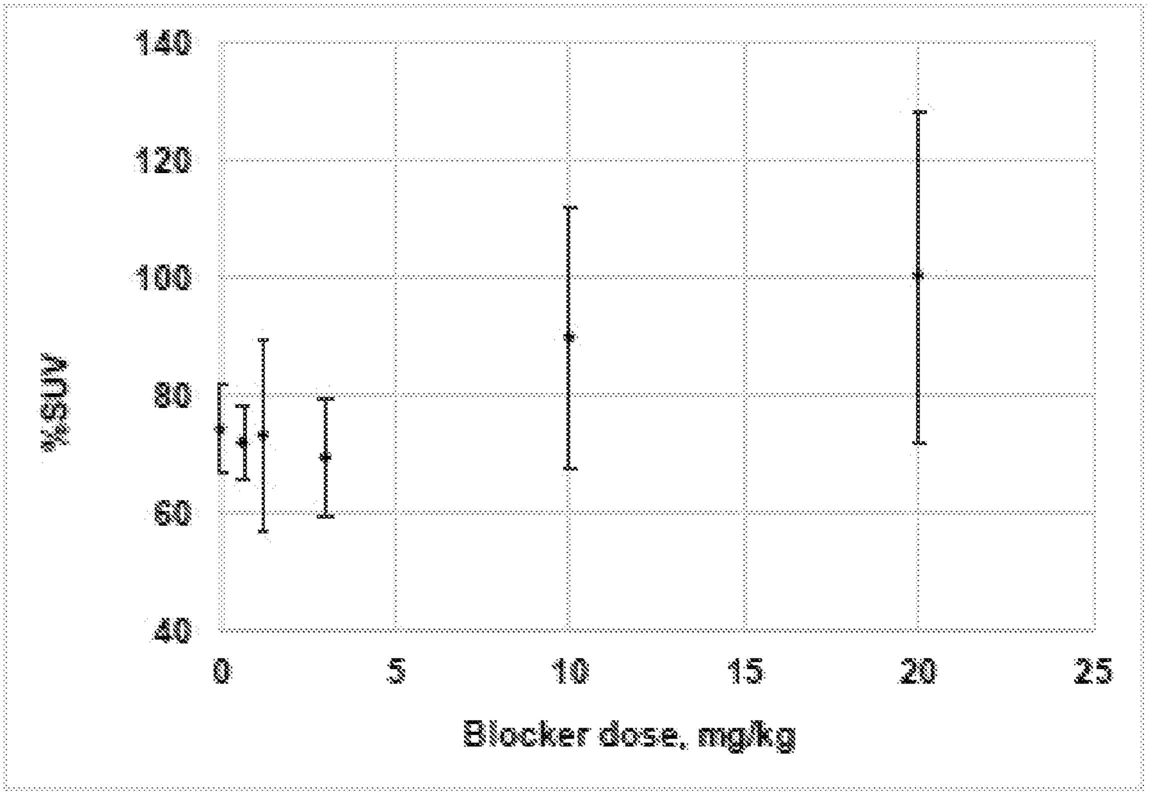
Figure 12:
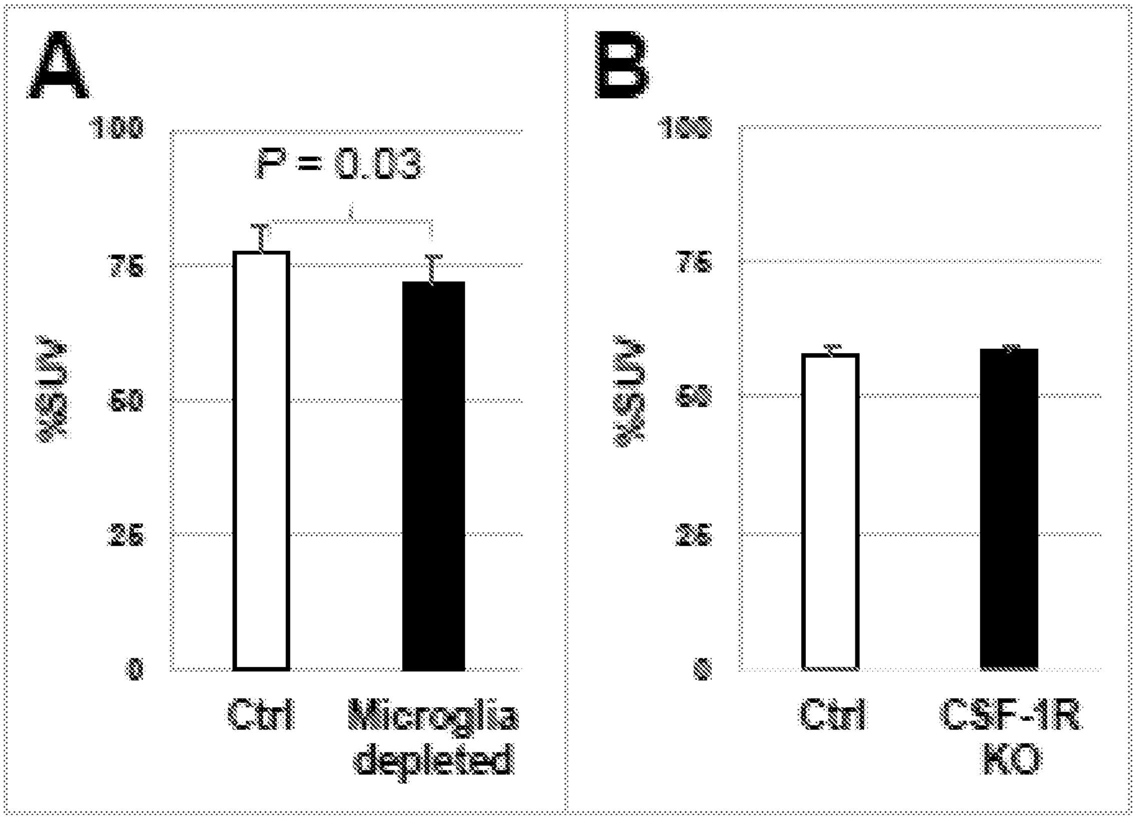
Figure 13:
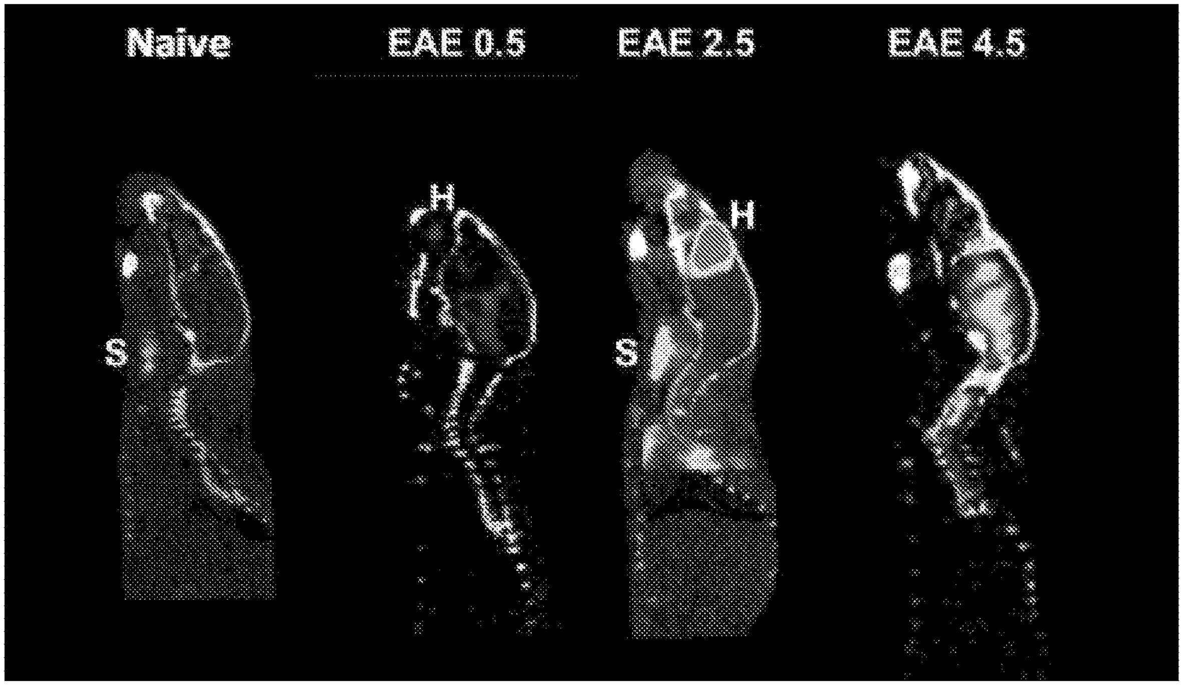
Figure 15:
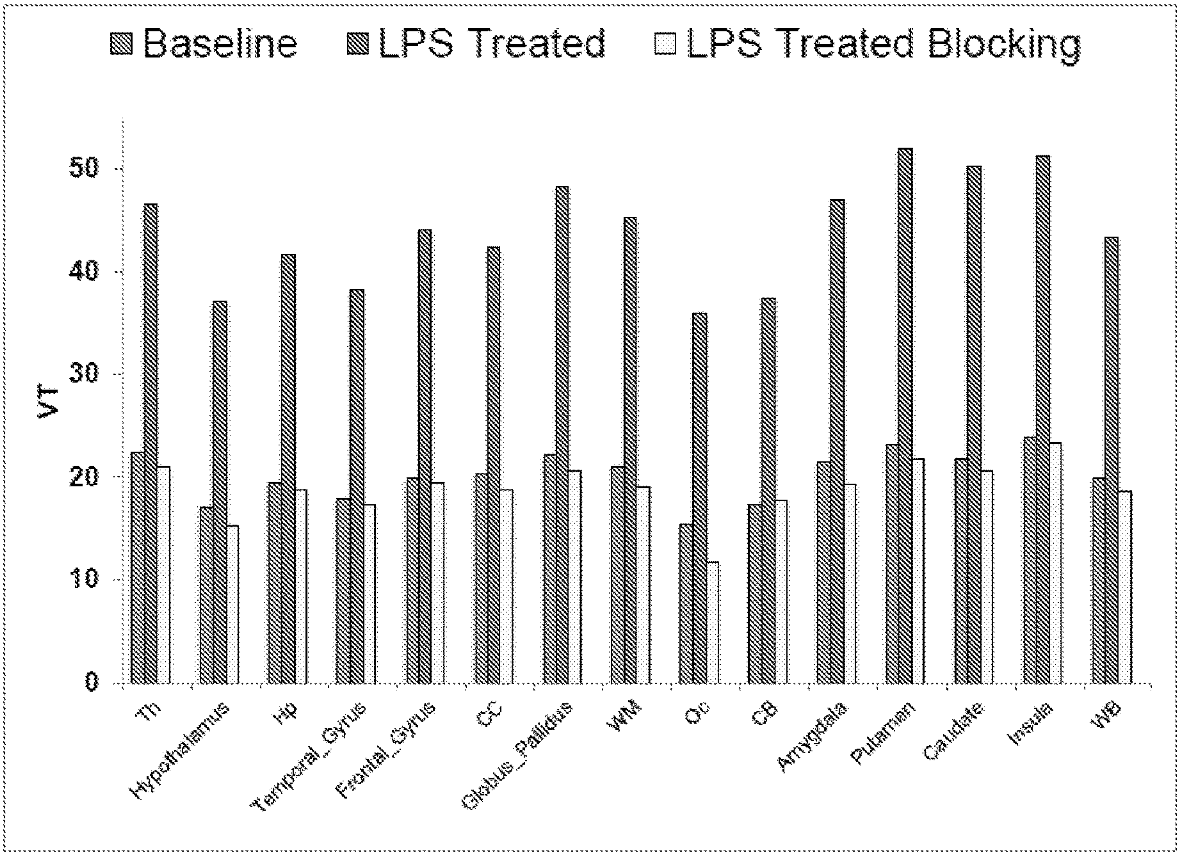
Figure 16:
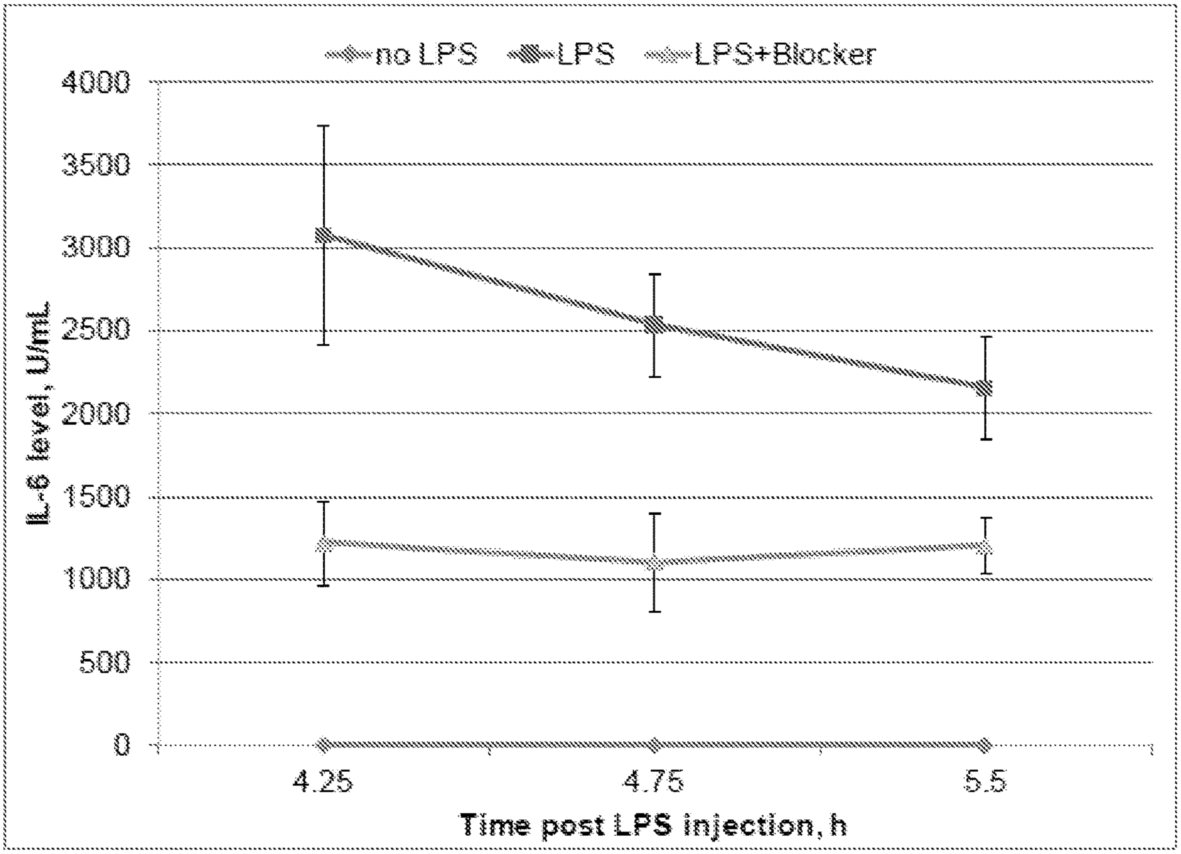
Figure 19:
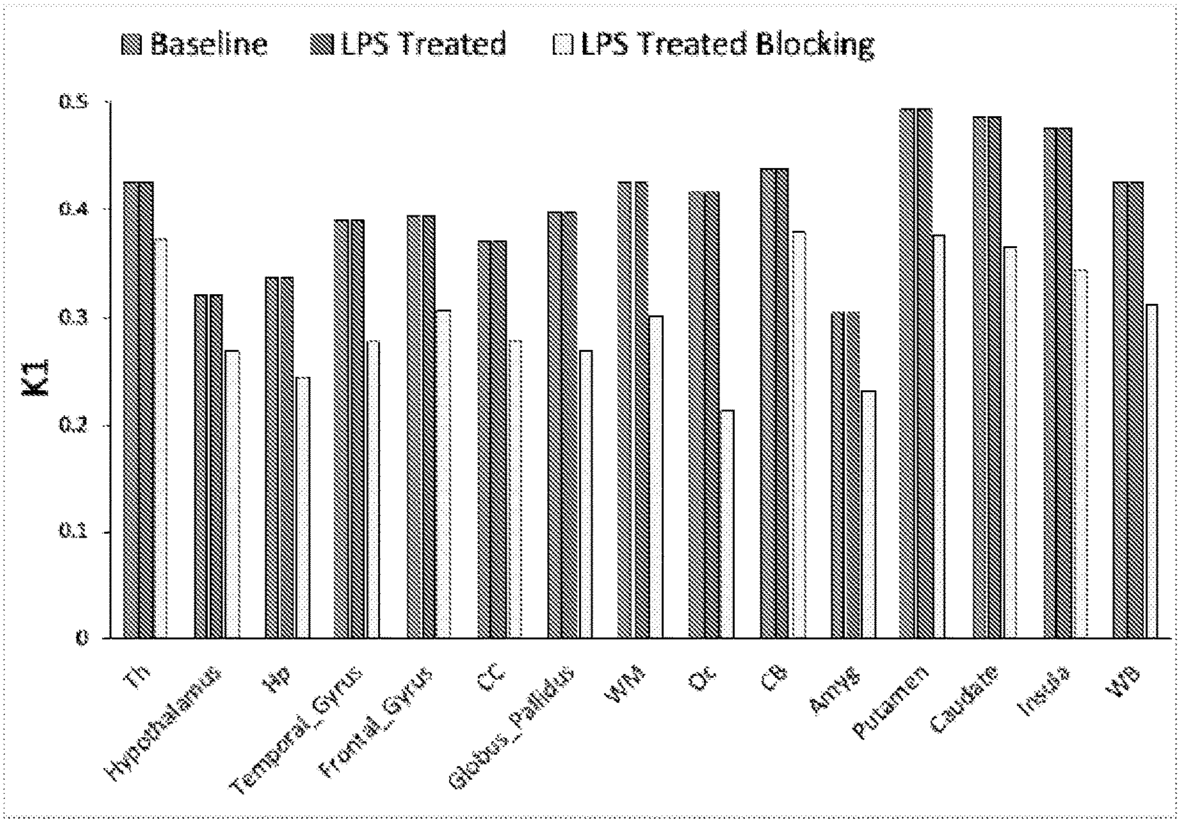
Figure 20:
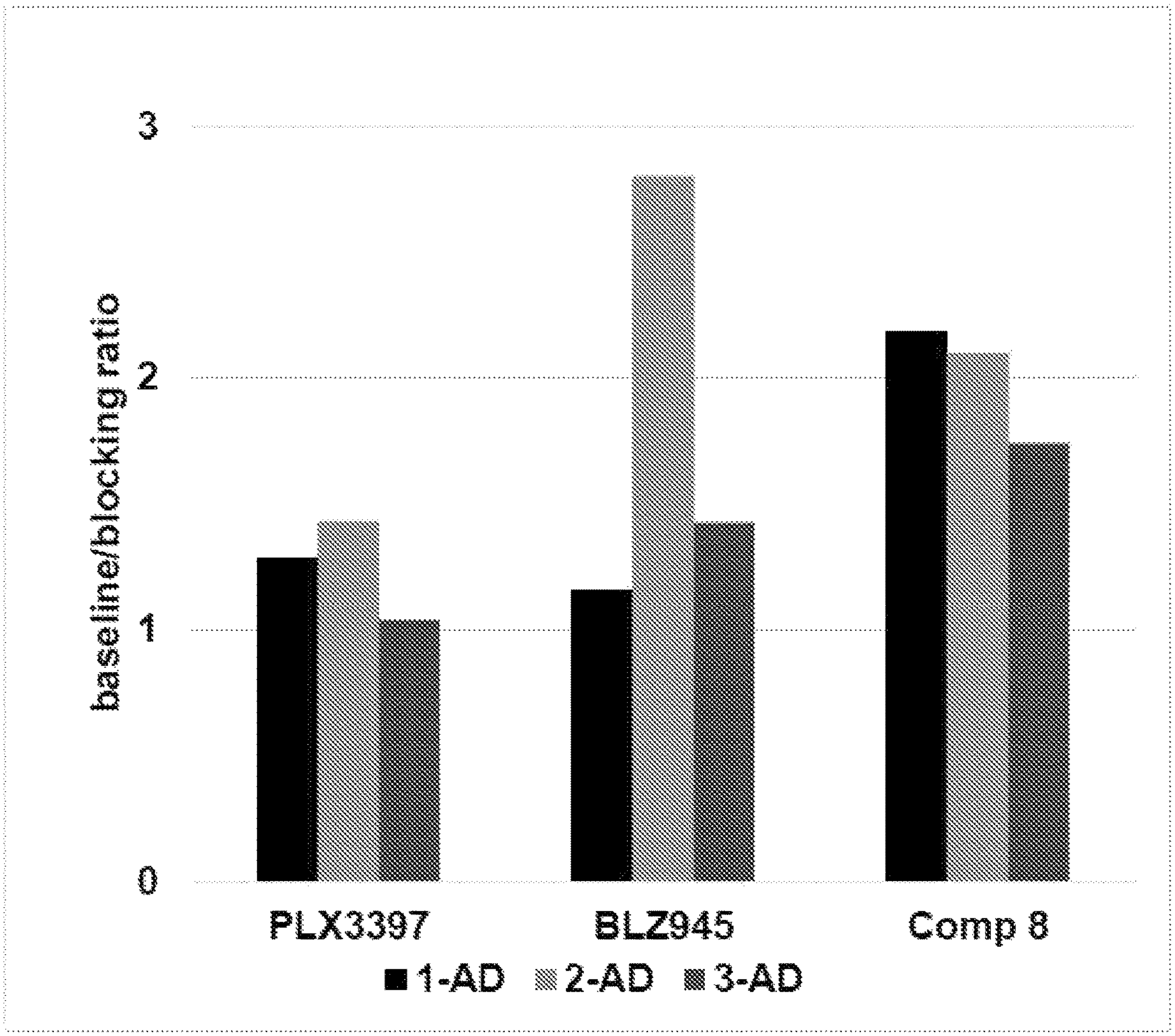

Having thus described the presently disclosed subject matter in general terms, reference will now be made to the accompanying Figures, which are not necessarily drawn to scale, and wherein:

FIG. 1A and FIG. 1B show a comparison of [$^{11}$C]CPPC brain uptake in sham and LPS: right forebrain injected mice, baseline, and blocking. Two independent experiments (FIG. 1A and FIG. 1B) were performed. The time point was 45 min after radiotracer injection; LPS (5 μg in 0.5 μL) or saline (0.5 μL) was injected into the right forebrain (ipsilateral frontal quadrant) 2-3 d before the radiotracer study. Blocker (CPPC) was injected i.p. 5 min before the radiotracer. (FIG. 1A) The regions of interest (ROIs) are cerebellum (CB), ipsilateral hemisphere (IH), and contralateral hemisphere (CH). The data are mean % SUV±SD (n=3). (FIG. 1B) The ROIs are cerebellum (CB), contralateral hemisphere (CH), ipsilateral caudal quadrant (ICQ), and ipsilateral frontal quadrant (IFQ). The data are mean % SUV±SD (n=4). Statistical analysis: comparison of LPS-baseline versus sham or LPS-block. *P<0.05; no asterisk indicates P>0.05 (ANOVA);

FIG. 2A, FIG. 2B, and FIG. 2C show brain uptake of CSF1R radiotracer [$^{11}$C]CPPC in control (Ctrl), LPS (i.p.)-treated mice (LPS base), and LPS (i.p.)-treated mice plus blocking with CSF1R inhibitors (LPS block) in three independent experiments. The time point was 45 min after radiotracer injection [LPS (10 mg/kg)]. (FIG. 2A) Data are mean % SUV±SD (n=5). CB, cerebellum. (FIG. 2B) Data are mean SUVR±SD (n=5). Blocker (CPPC, 1 mg/kg, i.p.) was injected in the LPS-treated mice. (FIG. 2C) Data are mean SUVR±SD (n=3-6). Blocker (compound 8, 2 mg/kg, i.p.) was injected in the LPS-treated mice. Statistical analysis: comparison of LPS-baseline versus control or LPS-block. *P<0.01; **P=0.03; no asterisk indicates P>0.05 (ANOVA);

FIG. 3 shows the comparison of the [$^{11}$C]CPPC brain uptake in transgenic AD (n=6) and control (n=5) mice. Time-point—45 min after radiotracer injection. Data: mean % SUV±SD. *P=0.04, **P<0.005 (ANOVA). The uptake of [$^{11}$C]CPPC was significantly greater in AD mouse brain regions. CB, cerebellum; Ctx, cortex; Hipp, hippocampus;

FIG. 4A and FIG. 4B show [$^{11}$C]CPPC PET/CT imaging in murine EAE. (FIG. 4A) MIP (Top), coronal (Middle), and sagittal (Bottom) slices showing radiotracer uptake from 45 to 60 min per projection in the indicated mice. Color scale range shows % ID/g tissue. (FIG. 4B) Regional brain uptake normalized by uptake in control animal vs. EAE severity. BS, brainstem; FCTX, frontal cortex;

FIG. 5A, FIG. 5B, FIG. 5C, and FIG. 5D show PET imaging of [$^{11}$C]CPPC in the same baboon in baseline, LPS, and LPS-plus-blocking experiments. The LPS dose was 0.05 mg/kg (i.v.), 4 h before radiotracer injection. (FIG. 5A) Parametric (VT) images. (FIG. 5B) Baseline regional brain SUV time-uptake curves of [$^{11}$C]CPPC. (FIG. 5C) Whole-brain SUV time-uptake curves of [$^{11}$C]CPPC: baseline (green), after LPS treatment (red) and blocking after LPS treatment (black). (FIG. 5D) Metabolite-corrected plasma SUV time-uptake curves of [$^{11}$C]CPPC: baseline (green), after LPS treatment (red), and LPS-plus-blocking (black). The Inset in FIG. 5D shows first 120 s of scanning;

FIG. 6 shows postmortem human autoradiography/[$^{11}$C]CPPC images (baseline and blocking) in inferior parietal lobe gray matter slices. Three subjects with Alzheimer's disease (1-AD, 2-AD, and 3-AD) and control (4-control) subject. See also FIG. 20 and Tables 5 and 6;

FIG. 7 shows that in the CNS cells the CSF1R gene is mainly expressed in microglia, whereas TSPO and P2RX7 genes exhibit multi-cellular expression. Abbreviations: OPC=Oligodendrocyte progenitor cells; FPKM=fragments per kilobase of transcript per million mapped reads. The graphs are from http://web.stanford.edu/group/barres_lab/brain_maseq.html;

FIG. 8 shows the synthesis of pre-CPPC;

FIG. 9 shows the radiosynthesis of [$^{11}$C]CPPC;

FIG. 10 shows a blocking study with [$^{11}$C]CPPC and blocker CPPC. The study demonstrated an insignificant blockade with lower doses (0.6-3 mg/kg) and insignificant gradual increase of uptake with escalating doses (10-20 mg/kg) of unlabeled CPPC at time-point of 45 min after the tracer injection. Data: % SUV±SD (n=5);

FIG. 11A and FIG. 11B show a comparison of baseline and blocking uptake of [$^{11}$C]CPPC in the cortex of CD1 mice in the same experiment without (FIG. 11A) and with blood correction (FIG. 11B). FIG. 11A: mean % SUV±SD (n=3). No significant difference between the baseline and blocking with two doses of unlabeled CPPC (0.6 and 3 mg/kg) (P>0.05). FIG. 11B: Data: mean cortex SUVR±SD (n=3). In the mice injected with two doses of CPPC blocker, the blood corrected SUVR value was significantly lower (P=0.05) than that in baseline (ANOVA). This experiment demonstrates that [$^{11}$C]CPPC specifically radiolabels CSF-1R in CD1 mouse brain cortex;

FIG. 12A and FIG. 12B show a comparison of whole brain uptake of [$^{11}$C]CPPC in control vs. microglia-depleted (FIG. 12A) and control vs. CSF1R knock-out (FIG. 12B) mice, 45 min after radiotracer injection. FIG. 12A: Data are mean % SUV±SD (n=5). FIG. 12B: Data are mean % SUV to blood±SD (n=5). Statistical analysis—ANOVA;

FIG. 13 shows sagittal slices of [$^{11}$C]CPPC PET/CT images in EAE mice with no thresholding. All images are scaled to the same maximum displayed in FIG. 4. S=salivary gland; H=Harderian gland;

FIG. 14A, FIG. 14B, and FIG. 14C show LPS treatment induced elevated expression of CSF1R in mouse brain. FIG. 14A: Relative level of Csf1r mRNA measured by quantitative real time PCR (n=5). FIG. 14B: Western blot analyses of total mouse brain extracts from control and LPS-treated mice brain. Each lane represents a mouse. FIG. 14C: Band intensities of the CSF1R were calculated and normalized with those of GAPDH from FIG. 14B (n=5);

FIG. 15 shows regional VT values of [$^{11}$C]CPPC in baseline (green), LPS-treated (red) and LPS plus blocker (yellow) baboon studies. Abbreviations: Th=thalamus; Hp=hippocampus; CC=corpus callosum; WM=white matter; Oc=occipital cortex; CB=cerebellum; Amyg=amygdala; WB=whole brain;

FIG. 16 shows levels of inflammatory cytokine IL-6 in baboon serum. The IL-6 level increased after the LPS injection and reduced in the LPS-plus-blocker study. IL-6 was measured with ELISA kit. Briefly: At three different time points (post injection 15, 45, and 90 minute), 2 mL of baboon peripheral blood was collected into BD Vacutainer (BD Biosciences, cat #367983, La Jolla, CA) and centrifuged down at 2,000×g for 10 min at room temperature. Serum was collected into sterile tubes and stored in −80 °C for future immunoassay. Serum samples were thawed on ice and the IL-6 level was measured using IL-6 Monkey Instant ELISA™ (Thermo Fisher Scientific, cat #BMS641INST, Halethorpe, MD) according to the manufacturer's protocol;

FIG. 17A and FIG. 17B show HPLC analysis of [$^{11}$C] CPPC ([$^{11}$C]JHU11744) radiometabolites in baboon plasma. FIG. 17A—Radio-HPLC chromatograms of [$^{11}$C]CPPC and blood plasma sample collected at different time intervals, FIG. 17B—time depended decrease of relative percentage of [$^{11}$C]CPPC in control and LPS or LPS and blocking agent treated baboons;

FIG. 18A, FIG. 18B, FIG. 18C, and FIG. 18D show representative plots of [$^{11}$C]CPPC kinetic analysis using (FIG. 18A) compartmental modeling and (FIG. 18B) Logan analysis, demonstrating both are suitable methods (representative region shown: putamen, green markers: PET study data points, solid lines: fitted data; (FIG. 18C) Comparisons of VT results by compartmental modeling and Logan analysis, in a representative baseline study, demonstrating they are highly comparable/correlated ($R^2$=0.9657); (FIG. 18D) Representative time consistency plots of regional VT estimates (region: putamen), showing stable results (<2.5% changes) were obtained using 60 min post injections;

FIG. 19 shows regional K1 values of [$^{11}$C]CPPC in baseline (green), LPS-treated (red) and LPS plus blocker (yellow) baboon studies. Abbreviations: Th=thalamus; Hp=hippocampus; CC=corpus callosum; WM=white matter; Oc=occipital cortex; CB=cerebellum; Amyg=amygdala; WB=whole brain; and FIG. 20 shows the baseline/blocking ratio with various blockers (PLX3397; BLZ945 and compound 8) in the autoradiography experiments with [$^{11}$C]CPPC in the AD postmortem human brain slices.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. PET RADIOTRACERS FOR IMAGING MACROPHAGE COLONY-STIMULATING FACTOR 1 RECEPTOR (CSF1R) IN NEUROINFLAMMATION

The macrophage colony stimulating factor-1 (CSF1) is one of the most common pro-inflammatory cytokine responsible for various inflammatory disorders. CSF1 interacts with its receptor, CSF1R, and leads to differentiation and proliferation of cells of monocyte/macrophage linage. Increased levels of CSF1R expression are associate with various neuroinflammation disorders, including, but not limited to, Alzheimer's disease (AD), brain tumors, multiple sclerosis (MS), traumatic brain injury, and the like. See Walker et al, 2017.

In the CNS, the CSF-1R's are mainly expressed by microglia (Akiyama, et al., 1994; Raivich et al., 1998), while the expression in other cells, including neurons is low. Chitu et al., 2016. Potentially, the CSF1R represents a selective binding site for imaging of microglial activation in neuroinflammation. On the contrary, the most commonly-used biomarkers of neuroinflammation, TSPO and P2RX7, both exhibit multi-cellular expression, Raivich et al., 1998, and, thus, cannot be considered as selective binding sites of microglial activation. See FIG. 10.

The potent and selective CSF1R inhibitor, 5-cyano-N-(4-(4-methylpiperazin-1-yl)-2-(piperidin-1-yl)phenyl)furan-2-carboxamide (1), was developed by the pharmaceutical industry as a potential anti-inflammatory agent. Illig et al., 2008.

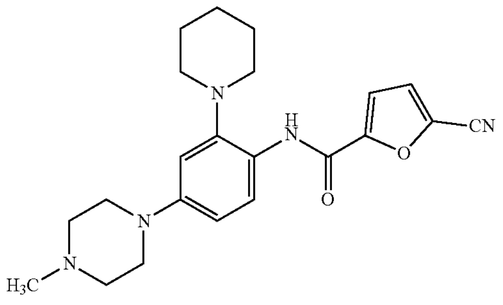 [SMILES: CN1CCN(c2ccc(NC(=O)c3ccc(C#N)o3)c(N3CCCCC3)c2)CC1]

5-cyano-N-(4-(4-methylpiperazin-1-yl)-2-(piperidin-1-yl)phenyl)furan-2-carboxamide (1)

The presently disclosed subject matter provides, in part, the radiosynthesis of [$^{11}$C]1 ([$^{11}$C]CMPPF; [$^{11}$C]JHU11744; 5-cyano-N-(4-(4-[$^{11}$C]methylpiperazin-1-yl)-2-(piperidin-1-yl)phenyl)furan-2-carboxamide), and its evaluation for PET imaging of CSF1R in neuroinflammation.

[$^{11}$C]1

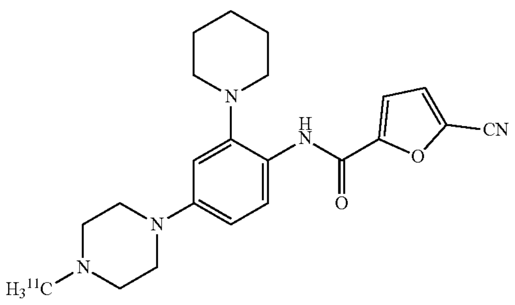 [SMILES: [11CH3]N1CCN(c2ccc(NC(=O)c3ccc(C#N)o3)c(N3CCCCC3)c2)CC1]

More generally, the presently disclosed subject matter provides a series of PET radiotracers for imaging macrophage colony-stimulating factor-1 receptor (CSF1R). The binding of the radiotracers at CSF1R was tested in animal models of neuroinflammation, experimental autoimmune encephalomyelitis (EAE) mice (multiple sclerosis model), and post-mortem Alzheimer's disease brain tissue. Particular compounds readily entered the brain in animal models. Yet more particular compounds specifically bound (and labeled) CSF1R in animal models of neuroinflammation. In some embodiments, the presently disclosed compounds exhibited significantly more uptake in animal models of neuroinflammation than in controls. In further embodiments, selected compounds specifically label CSF1R in human Alzheimer's brain tissue. Accordingly, the presently disclosed compounds can be used in studying CSF1R in neuroinflammation and neurodegeneration.

A. Imaging Agents of Formula (I)

In some embodiments, the presently disclosed subject matter provides an imaging agent for imaging macrophage colony stimulating factor receptor (CSF1R) in a subject afflicted or suspected of being afflicted with one or more neuroinflammatory or neurodegenerative diseases or conditions, the imaging agent comprising a compound of formula (I):

(I)

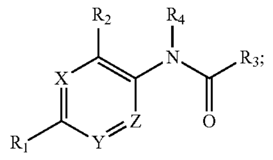

wherein:

X, Y, and Z are each independently selected from the group consisting of —N— and —$CR_5$—, wherein $R_5$ is selected from the group consisting of H, substituted or unsubstituted $C_1$-$C_8$ alkyl, or R*, wherein R* is a moiety comprising a radioisotope suitable for positron emission tomography (PET) imaging or the radioisotope itself;

$R_1$ is selected from the group consisting of substituted or unsubstituted heteroalkyl, substituted or unsubstituted heteroaryl, $C_1$-$C_8$ alkoxyl, $C_1$-$C_8$ alkylamino, $C_1$-$C_8$ dialkylamino, —N($C_1$-$C_8$ alkyl)($SO_2$)($C_1$-$C_8$ alkyl), wherein $R_1$ optionally can be substituted with R* or $R_1$ can be a radioisotope suitable for PET imaging;

$R_2$ is substituted or unsubstituted heteroalkyl, wherein $R_2$ optionally can be substituted with R*;

$R_3$ is substituted or unsubstituted heteroaryl, wherein $R_3$ optionally can be substituted with R*; and $R_4$ is selected from the group consisting of H, substituted or unsubstituted $C_1$-$C_8$ alkyl, $C_1$-$C_8$ alkoxyl, cycloalkyl, cycloheteroalkyl, aryl, and heteroaryl; or a pharmaceutically acceptable salt thereof;

wherein at least one of $R_1$, $R_2$, $R_3$ or $R_5$ is substituted with R* or is a radioisotope suitable for PET imaging.

In some embodiments, $R_1$ is selected from the group consisting of substituted or unsubstituted piperazinyl, substituted or unsubstituted morpholinyl, 1,1-dioxide-thiomorpholinyl, substituted or unsubstituted pyrazolyl, substituted or unsubstituted imidazolyl, $C_1$-$C_8$ alkoxyl, $C_1$-$C_8$ alkylamino, $C_1$-$C_8$ dialkylamino, —N($C_1$-$C_8$ alkyl)($SO_2$)($C_1$-$C_8$ alkyl), wherein $R_1$ optionally can be substituted with R* or $R_1$ can be a radioisotope suitable for PET imaging.

In some embodiments, $R_2$ is selected from the group consisting of substituted or unsubstituted piperidinyl and substituted or unsubstituted morpholinyl, wherein $R_2$ optionally can be substituted with R*.

In some embodiments, $R_3$ is selected from the group consisting of substituted or unsubstituted pyrrolyl and substituted or unsubstituted furanyl, wherein $R_3$ optionally can be substituted with R*.

In certain embodiments, $R_1$ is selected from the group consisting of:

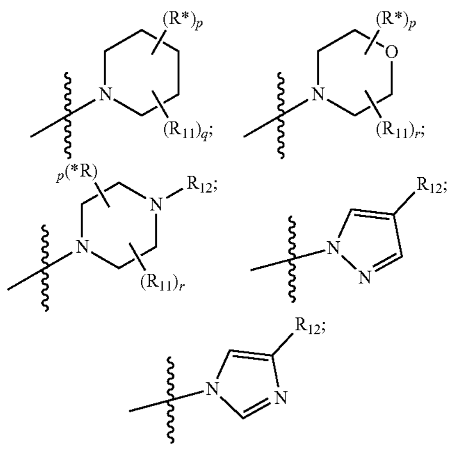

wherein:

p is an integer selected from 0 and 1;

q is an integer selected from the group consisting of 0, 1, 2, 3, 4, and 5;

r is an integer selected from the group consisting of 0, 1, 2, 3, and 4;

$R_{11}$ is selected from the group consisting of $C_1$-$C_8$ substituted or unsubstituted alkyl, $C_1$-$C_8$ alkoxyl, hydroxyl, amino, cyano, halogen, carboxyl, and —$CF_3$; and $R_{12}$ is selected from the group consisting of H, substituted or unsubstituted $C_1$-$C_8$ alkyl, carboxyl, —($SO_2$)—($C_1$-$C_8$ alkyl), and R*.

In certain embodiments, $R_2$ is selected from the group consisting of:

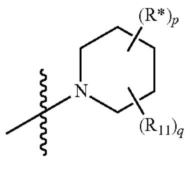

and

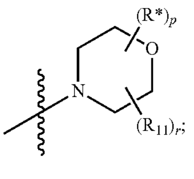

wherein:

p is an integer selected from 0 and 1;

q is an integer selected from the group consisting of 0, 1, 2, 3, 4, and 5;

r is an integer selected from the group consisting of 0, 1, 2, 3, and 4;

$R_{11}$ is selected from the group consisting of $C_1$-$C_8$ substituted or unsubstituted alkyl, $C_1$-$C_8$ alkoxyl, hydroxyl, amino, cyano, halogen, carboxyl, and —$CF_3$.

In certain embodiments, $R_3$ is selected from the group consisting of:

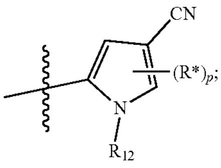
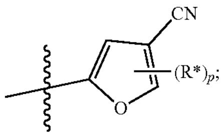
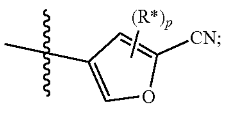
and
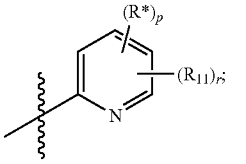

wherein:

p is an integer selected from the group consisting of 0 and 1;

$R_{11}$ is selected from the group consisting of $C_1$-$C_8$ substituted or unsubstituted alkyl, $C_1$-$C_8$ alkoxyl, hydroxyl, amino, cyano, halogen, carboxyl, and —$CF_3$; and $R_{12}$ is selected from the group consisting of H, substituted or unsubstituted $C_1$-$C_8$ alkyl, carboxyl, —($SO_2$)—($C_1$-$C_8$ alkyl), and R*.

In certain embodiments, (a) X, Y, Z are each —$CR_5$—;

(b) X and Z are each —N— and Y is —$CR_5$—;

(c) X is —N— and Y and Z are each —$CR_5$—;

(d) X and Y are N and Z is —$CR_5$—;

(e) X and Y are each —$CR_5$— and Z is N;

wherein $R_5$ at least at one occurrence optionally can be substituted with R*.

In particular embodiments, the compound of formula (I) is a compound of formula (Ia):

(Ia)

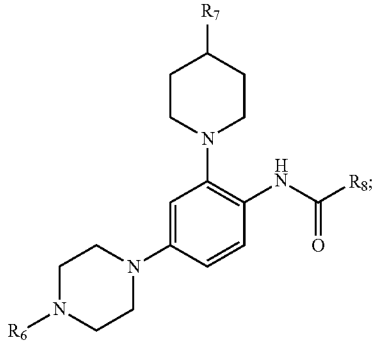

wherein:

$R_6$ is selected from the group consisting of H, $C_1$-$C_8$ alkyl, —C(═O)—O—$R_9$, and —$(CH_2)_n$—$R_{10}$, wherein n is an integer selected from 0, 1, 2, 3, 4, 5, 6, 7, and 8; $R_9$ and $R_{10}$ are each $C_1$-$C_8$ straight chain or branched alkyl, and wherein $R_6$ optionally can be substituted with R* or $R_6$ can be R*;

$R_7$ is selected from the group consisting of H or $C_1$-$C_8$ alkyl, wherein $R_7$ optionally can be substituted with R* or $R_7$ can be R*; and $R_8$ is substituted or unsubstituted pyrrolyl, furanyl, and pyridinyl, wherein $R_8$ optionally can be substituted with R*; or a pharmaceutically acceptable salt thereof;

wherein at least one of $R_6$, $R_7$, or $R_8$ is substituted with R* or is R*.

In more particular embodiments, $R_6$ is selected from the group consisting of hydrogen, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, and —C(═O)—O—($C_1$-$C_8$ alkyl)$_3$; $R_7$ is selected from the group consisting of hydrogen, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl; $R_8$ is selected from the group consisting of

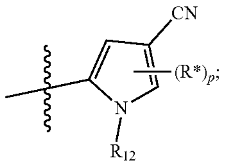
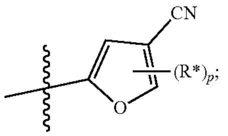
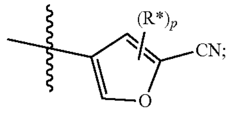
and
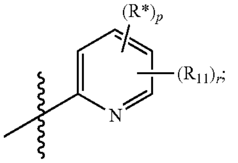

wherein:

p is an integer selected from the group consisting of 0 and 1;

$R_{11}$ is selected from the group consisting of $C_1$-$C_8$ substituted or unsubstituted alkyl, $C_1$-$C_8$ alkoxyl, hydroxyl, amino, cyano, halogen, carboxyl, and —$CF_3$; and $R_{12}$ is selected from the group consisting of H, substituted or unsubstituted $C_1$-$C_8$ alkyl, carboxyl, —($SO_2$)—($C_1$-$C_8$ alkyl), and R*; and wherein each of $R_6$, $R_7$, and $R_8$ optionally can be substituted with R*.

In yet more particular embodiments, the imaging agent is selected from the group consisting of:

5-Cyano-N-(4-(4-methylpiperazin-1-yl)-2-(piperidin-1-yl)phenyl)furan-2-carboxamide (1a);

5-Cyano-N-(4-(4-methylpiperazin-1-yl)-2-(4-methylpiperidin-1-yl)phenyl)furan-2-carboxamide (1c);

4-Cyano-N-(4-(4-methylpiperazin-1-yl)-2-(4-methylpiperidin-1-yl)phenyl)-1H-pyrrole-2-carboxamide (1e);

4-Cyano-N-(4-(4-methylpiperazin-1-yl)-2-(piperidin-1-yl)phenyl)furan-2-carboxamide (1g);

5-Cyano-N-(4-(4-methylpiperazin-1-yl)-2-(piperidin-1-yl)phenyl)furan-3-carboxamide (1h);

6-Fluoro-N-(4-(4-methylpiperazin-1-yl)-2-(piperidin-1-yl)phenyl)picolinamide (1i);

6-Bromo-N-(4-(4-methylpiperazin-1-yl)-2-(piperidin-1-yl)phenyl)picolinamide (1i);

Tert-butyl 4-(4-(5-cyanofuran-2-carboxamido)-3-(piperidin-1-yl)phenyl)piperazine-1-carboxylate (7a);

Tert-butyl 4-(4-(5-cyanofuran-2-carboxamido)-3-(4-methylpiperidin-1-yl)phenyl)piperazine-1-carboxylate (7b);

Tert-butyl 4-(4-(4-cyano-1H-pyrrole-2-carboxamido)-3-(4-methylpiperidin-1-yl)phenyl)piperazine-1-carboxylate (7c);

5-Cyano-N-(4-(piperazin-1-yl)-2-(piperidin-1-yl)phenyl)furan-2-carboxamide (Tb);

5-Cyano-N-(2-(4-methylpiperidin-1-yl)-4-(piperazin-1-yl)phenyl)furan-2-carboxamide (1d);

4-Cyano-N-(2-(4-methylpiperidin-1-yl)-4-(piperazin-1-yl)phenyl)-1H-pyrrole-2-carboxamide (1f);

5-Cyano-N-(4-(4-(2-fluoroethyl)piperazin-1-yl)-2-(piperidin-1-yl)phenyl)furan-2-carboxamide (1k);

4-Cyano-N-(4-(4-(2-fluoroethyl)piperazin-1-yl)-2-(4-methylpiperidin-1-yl)phenyl)-1H-pyrrole-2-carboxamide (1l);

N-(4-(4-(2-bromoethyl)piperazin-1-yl)-2-(piperidin-1-yl) phenyl)-S-cyanofuran-2-carboxamide (1m);

4-Cyano-1H-imidazole-2-carboxylic Acid {2-Cyclohex-1-enyl-4-[1-(2-dimethylamino-acetyl)-piperidin-4-yl]-phenyl}-amide (1g); and 4-Cyano-N-(5-(1-(methylglycyl)piperidin-4-yl)-2',3',4',5'-tetrahydro-[1,1'-biphenyl]-2-yl)-1H-imidazole-2-carboxamide (1h).

In some embodiments, R* is selected from the group consisting of $^{11}C$, $^{18}F$, and $—(CH_2)_m—R_{13}$, wherein $R_{13}$ is $C_1$-$C_8$ straight chain or branched alkyl, which optionally can be substituted with a radioisotope suitable for PET imaging.

In certain embodiments, the radioisotope suitable for PET imaging is selected from the group consisting of $^{11}C$ and $^{18}F$.

In yet more certain embodiments, the compound of formula (I) is:

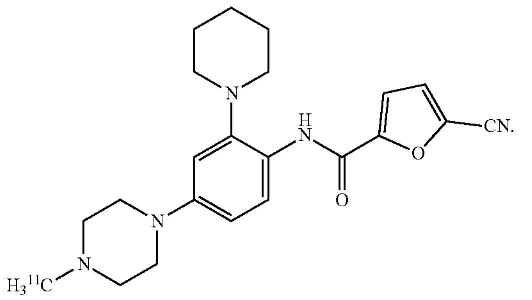

B. Methods of Imaging

In some embodiments, the presently disclosed subject matter provides a method for imaging macrophage colony stimulating factor receptor (CSF1R) in a subject afflicted or suspected of being afflicted with one or more neuroinflammatory or neurodegenerative diseases or conditions, the method comprising administering to the subject an effective amount of an imaging agent of formula (I), or a pharmaceutically acceptable salt thereof and taking a PET image.

In particular embodiments, the neuroinflammatory or neurodegenerative disease or condition is selected from the group consisting of Alzheimer's disease (AD), multiple sclerosis (MS), a traumatic brain injury, a brain tumor, HIV-associated cognitive impairment, and one or more demyelinating diseases.

Examples of demyelinating diseases include, but are not limited to, MS, Devic's disease, and other inflammatory demyelinating diseases; leukodystrophic disorders, including CNS neuropathies, central pontine myelinolysis, tabe dorsalis (syphilitic myelopathy), and progressive multifocal leukoencephalopathy; and demyelinating diseases of the peripheral nervous system, including Guillain-Barre syndrome, chronic inflammatory demyelinating polyneuropathy, Charcot-Marie-Tooth disease, hereditary neuropathy with liability to pressure palsy; and peripheral neuropathy, myelopathy, and optic neuropathy.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

"Contacting" means any action which results in at least one compound of the presently disclosed subject matter physically contacting at least one CSF1R-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The term "combination" is used in its broadest sense and means that a subject is administered at least two agents, more particularly a presently disclosed compound of and at least one other active agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

C. Kits

In yet other embodiments, the presently disclosed subject matter provides a kit comprising a presently disclosed compound.

In certain embodiments, the kit provides packaged pharmaceutical compositions comprising a pharmaceutically acceptable carrier and a compound of the invention. In certain embodiments the packaged pharmaceutical composition will comprise the reaction precursors necessary to generate the compound of the invention upon combination with a radio labeled precursor. Other packaged pharmaceutical compositions provided by the present invention further comprise indicia comprising at least one of: instructions for preparing compounds according to the invention from supplied precursors, instructions for using the composition to image cells or tissues expressing CSF1, or instructions for using the composition to image glutamatergic neurotransmission in a patient suffering from a stress-related disorder, or instructions for using the composition to image prostate cancer.

D. Pharmaceutical Compositions and Administration

In another aspect, the present disclosure provides a pharmaceutical composition including a presently disclosed compound alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. GENERAL DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to the presently disclosed compounds are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., $—CH_2O—$ is equivalent to $—OCH_2—$; —C(═O)O— is equivalent to —OC(═O)—; —OC(═O)NR— is equivalent to —NRC(═O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_1$-20 inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) 0, N, P and S and Si may be placed at any interior position of the heteroalkyl group or at the position at which alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_{25}-S(O)-CH_3$, $-CH_2-CH_2-S(O)_2-CH_3$, $-CH{=}CH-O-CH_3$, $-Si(CH_3)_3$, $-CH_2-CH{=}N-OCH_3$, $-CH{=}CH-N(CH_3)-CH_3$, $O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$.

As described above, heteroalkyl groups, as used herein, include those groups that are attached to the remainder of the molecule through a heteroatom, such as $-C(O)NR'$, $-NR'R''$, $-OR'$, $-SR$, $-S(O)R$, and/or $-S(O_2)R'$. Where "heteroalkyl" is recited, followed by recitations of specific heteroalkyl groups, such as $-NR'R$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($-CH_2-$); ethylene ($-CH_2-CH_2-$); propylene ($-(CH_2)_3-$); cyclohexylene ($-C_6H_{10}-$); $-CH{=}CH-CH{=}CH-$; $-CH{=}CH-CH_2-$; $-CH_2CH_2CH_2CH_2-$, $-CH_2CH{=}CHCH_2-$, $-CH_2CsCCH_2-$, $-CH_2CH_2CH(CH_2CH_2CH_3)CH_2-$, $-(CH_2)_q-N(R)-(CH_2)_r-$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula $-C(O)OR'-$ represents both $-C(O)OR'-$ and $-R'OC(O)-$.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

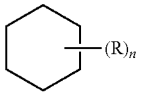
or
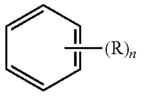

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

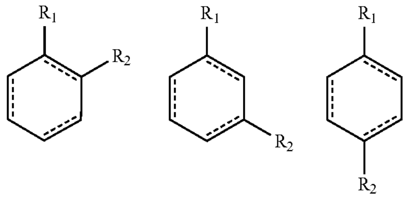

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol () denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R'', —SR', -halogen, —SiR'R''R''', —OC(O)R', —C(O)R', —$CO_2$R', —C(O)NR'R'', —OC(O)NR'R'', —NR''C(O)R', —NR'—C(O)NR''R''', —NR''C(O)OR', —NR—C(NR'R'')=NR''', —S(O)R', —$S(O)_2$R', —$S(O)_2$NR'R'', —NRSO$_2$R', —CN and —$NO_2$ in a number ranging from zero to (2m'+1), where m' is the total number of carbon atoms in such groups. R', R'', R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 4-, 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R'', —SR', —SiR'R''R''', —OC(O)R', —C(O)R', —$CO_2$R', —C(O)NR'R'', —OC(O)NR'R'', —NR''C(O)R', —NR'—C(O)NR''R''', —NR''C(O)OR', —NR—C(NR'R''R''')=NR'''', —NR—C(NR'R'')=NR'''—S(O)R', —$S(O)_2$R', —$S(O)_2$NR'R'', —NRSO$_2$R', —CN and —$NO_2$, —R', —$N_3$, —CH$(Ph)_2$, fluoro($C_1$-$C_4$)alkoxo, and fluoro($C_1$-$C_4$)alkyl, in a number ranging from zero to the total number of open valences on aromatic ring system; and where R', R'', R' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R'', R' and R'''' groups when more than one of these groups is present.

Two of the substituents on adjacent atoms of aryl or heteroaryl ring may optionally form a ring of the formula -T-C(O)—$(CRR')_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula $—(CRR')_s—X'—(C''R''')_d—$, where s and d are independently integers of from 0 to 3, and X' is —O—, —NR'—, —S—, —S(O)—, $—S(O)_2—$, or $—S(O)_2NR'—$. The substituents R, R', R'' and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(═O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(═O)NR', esters, —RC (═O)OR', ketones, —RC(═O)R', and aldehydes, —RC (═O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_1$-20 inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5—CH_2—O—$. An aralkyloxyl group can optionally be substituted.

"Alkoxycarbonyl" refers to an alkyl-O—C(═O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(═O)— group. Exemplary aryloxycarbonyl groups include phenoxy- and naphthoxy-carbonyl.

"Aralkoxycarbonyl" refers to an aralkyl-O—C(═O)— group. An exemplary aralkoxycarbonyl group is benzyloxycarbonyl.

"Carbamoyl" refers to an amide group of the formula $—C(═O)NH_2$. "Alkylcarbamoyl" refers to a R'RN—C (═O)— group wherein one of R and R' is hydrogen and the other of R and R' is alkyl and/or substituted alkyl as previously described. "Dialkylcarbamoyl" refers to a R'RN—C(═O)— group wherein each of R and R' is independently alkyl and/or substituted alkyl as previously described.

The term carbonyldioxyl, as used herein, refers to a carbonate group of the formula —O—C(═O)—OR.

"Acyloxyl" refers to an acyl-O— group wherein acyl is as previously described.

The term "amino" refers to the $—NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R'', wherein R' and R'' are each independently selected from the group consisting of alkyl groups. The term trialkylamino refers to a group having the structure —NR'R''R''', wherein R', R'', and R''' are each independently selected from the group consisting of alkyl groups. Additionally, R', R'', and/or R''' taken together may optionally be $—(CH_2)_k—$ where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R'', wherein R' and R'' are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(═O)— group, and can include an aldehyde group represented by the general formula R—C(═O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the $—NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R

The term ureido refers to a urea group of the formula —NH—CO—$NH_2$.

The term "protecting group" in reference to the presently disclosed compounds refers to a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Representative examples of protecting groups include, but are not limited to, benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.10% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Pet Imaging of Microglia by Targeting Macrophage Colony-Stimulating Factor 1 Receptor (Csf1R)

1.1 Overview 5-cyano-N-(4-(4-[$^{11}$C]methylpiperazin-1-yl)-2-(piperidin-1-yl)phenyl)furan-2-carboxamide ([$^{11}$C]CPPC) is a PET radiotracer specific for CSF1R, a microglia-specific marker. This compound can be used as a noninvasive tool for imaging of reactive microglia, disease-associated microglia and their contribution to neuroinflammation in vivo. Neuroinflammation is posited to be an underlying pathogenic feature of a wide variety of neuropsychiatric disorders. [$^{11}$C]CPPC also may be used to study specifically the immune environment of malignancies of the central nervous system and to monitor potential adverse neuroinflammatory effects of immunotherapy for peripheral malignancies. This PET agent will be valuable in the development of new therapeutics for neuroinflammation, particularly those targeting CSF1R, not only by providing a noninvasive, repeatable readout in patients, but also by enabling measurement of drug target engagement.

While neuroinflammation is an evolving concept and the cells involved and their functions are being defined, microglia are understood to be a key cellular mediator of brain injury and repair. The ability to measure microglial activity specifically and noninvasively would be a boon to the study of neuroinflammation, which is involved in a wide variety of neuropsychiatric disorders including traumatic brain injury, demyelinating disease, Alzheimer's disease (AD), and Parkinson's disease, among others.

[$^{11}$C]CPPC is a positron-emitting, high-affinity ligand that is specific for the macrophage colony-stimulating factor 1 receptor (CSF1R), the expression of which is essentially restricted to microglia within brain. [$^{11}$C]CPPC demonstrates high and specific brain uptake in a murine and nonhuman primate lipopolysaccharide model of neuroinflammation. It also shows specific and elevated uptake in a murine model of AD, experimental allergic encephalomyelitis murine model of demyelination and in postmortem brain tissue of patients with AD. Radiation dosimetry in mice indicated [$^{11}$C]CPPC to be safe for future human studies. [$^{11}$C]CPPC can be synthesized in sufficient radiochemical yield, purity, and specific radioactivity and possesses binding specificity in relevant models that indicate potential for human PET imaging of CSF1R and the microglial component of neuroinflammation.

1.2 Scope of Work

The potent and selective CSF1R inhibitor, 5-cyano-N-(4-(4-methylpiperazin-1-yl)-2-(piperidin-1-yl)phenyl)furan-2-carboxamide, was developed by the pharmaceutical industry (Illig C R, et al. (2008)). Here, the radiosynthesis of its isotopolog, 5-cyano-N-(4-(4-[$^{11}$C]methylpiperazin-1-yl)-2-

(piperidin-1-yl)phenyl) furan-2-carboxamide ([$^{11}$C]CPPC) is described herein, and the potential of [$^{11}$C]CPPC for PET imaging of CSF1R in neuroinflammation is evaluated 1.3 Materials and Methods 1.3.1. Chemistry CSF1R inhibitors BLZ945 (Krauser J A, et al. (2015)) and pexidartinib (PLX3397) (DeNardo D G, et al. (2011)) were obtained commercially, and compound 8 was prepared in-house as described previously (Illig C R, et al. (2008)). The synthesis of CPPC [5-cyano-N-(4-(4-methylpiperazin-1-yl)-2-(piperidin-1-yl)phenyl)furan-2-carboxamide]was performed as described previously (Illig C R, et al. (2008)) and the nor-methyl precursor for radiolabeling of [$^{11}$C]CPPC, 5-cyano-N-(4-(piperazin-1-yl)-2-(piperidin-1-yl)phenyl) furan-2-carboxamide (Pre-CPPC), was prepared similarly (FIG. 8) [$^{11}$C]CPPC was prepared by reaction of [$^{11}$C]$CH_3$I with Pre-CPPC (FIG. 9).

1.3.2 Biodistribution and PET Imaging Studies with [$^{11}$C] CPPC in Animals

Animal protocols were approved by the Animal Care and Use Committee of the Johns Hopkins Medical Institutions.

1.3.3 Animals

C57BL/6J mice (22-27 g) or CD-1 mice (25-27 g) from Charles River Laboratories served as controls. Microglia-depleted mice were obtained as described previously (Elmore M R, et al. (2014)). CSF1R KO (B6.Cg-Csf1r$^{tm1.2Jwp}$/J) mice were purchased from Jackson Laboratories. A mouse model of AD-related amyloidosis-overexpressing Amyloid Precursor Protein with Swedish and Indiana mutations was prepared in-house (Melnikova T, et al. (2013)). Male CD-1 mice were injected intracranially (Dobos N, et al. (2012)) with LPS (5 pug; right forebrain) as an intracranial LPS model of neuroinflammation (i.c.-LPS) An i.p. model of neuroinflammation (i.p.-LPS) was generated by injecting male CD-1 mice with LPS (10 mg/kg: 0.2 mL; i.p.) as described previously (Qin L, et al. (2007)). For the Experimental Autoimmune Encephalitis (EAE) mouse model, female C57BL/6J mice were inoculated with $MOG_{35-55}$ peptide, as described previously (Jones M V, et al. (2008)). Symptomatic MOG-inoculated mice and an uninoculated, healthy mouse were scanned 14 d after the first inoculation.

1.3.4 [$^{11}$C]CPPC Brain Regional Biodistribution in Mice

The outcome of mouse experiments was calculated as percentage of standardized uptake value (% SUV) or % SUV corrected for radioactivity concentration in blood (SUVR):SUVR=% SUV tissue/% SUV bloodSUVR=% SUV tissue/% SUV blood.

1.3.5 Baseline

Control mice were killed by cervical dislocation at various time points following injection of 5.6 MBq (0.15 mCi) [$^{11}$C]CPPC in 0.2 mL of saline into a lateral tail vein. The brains were removed and dissected on ice. Various brain regions were weighed, and their radioactivity content was determined in a γ counter. All other mouse biodistribution studies were performed similarly.

1.3.6 Blocking

Mice (male CD1 or C57BL/6J) were killed by cervical dislocation at 45 min following i.v. injection of [$^{11}$C]CPPC. The blockers, CPPC (0.3, 0.6, 1.2, 3.0, 10, and 20 mg/kg), or CSF1R inhibitor, compound 8 (Illig C R, et al. (2008)) (2 mg/kg), were given i.p., 5 min before [$^{11}$C]CPPC, whereas baseline animals received vehicle. The brains were removed and dissected on ice, and blood samples were taken from the heart. Regional brain uptake of [$^{11}$C]CPPC at baseline was compared with that with blocking.

1.3.7 Biodistribution Studies in Mouse Neuroinflammation Models (LPS-Treated, AD)

These studies were performed similarly to the baseline and blocking experiments in control mice.

1.3.8 Determination of CSF1R Levels in Brains of Control and LPS-Treated Mice

Figure 14:
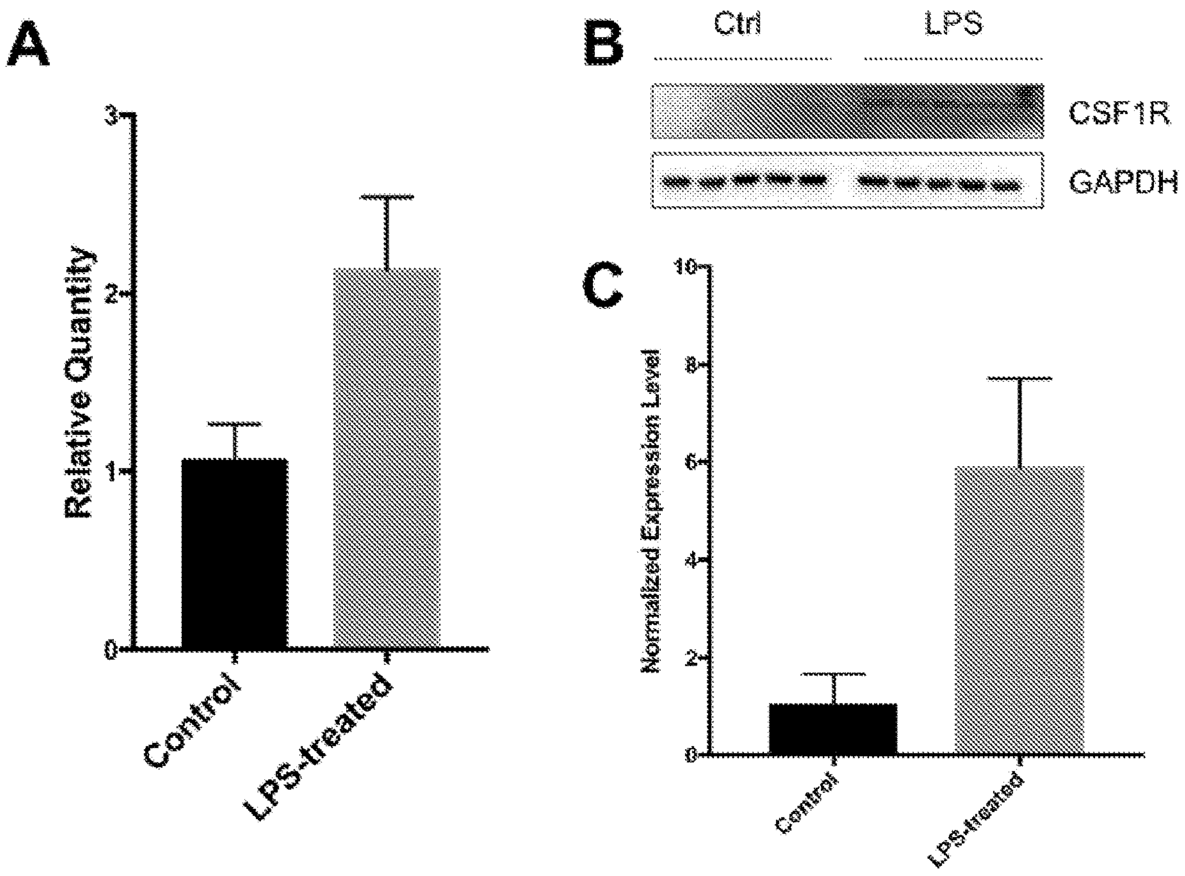

The levels of Csf1r mRNA and CSF1R protein were measured by qRT-PCR and Western blot analyses, respectively (FIG. 14).

1.3.9 PET/CT Imaging in EAE Mice

Each mouse (three EAE and one control) was injected i.v. with [$^{11}$C]CPPC, followed by imaging with a PET/CT scanner. PET and CT data were reconstructed using the manufacturer's software and displayed using a medical imaging data analysis (AMIDE) software (amide.sourceforge.net/). To preserve dynamic range, Harderian and salivary gland PET signal was partially masked.

1.3.10 Whole-Body Radiation Dosimetry in Mice

Male CD-1 mice were injected with [$^{11}$C]CPPC as described above for baseline studies and were euthanized at 10, 30, 45, 60, and 90 min after treatment. The various organs were quickly removed and percentage injected dose (% ID) per organ was determined. The human radiation dosimetry of [$^{11}$C]CPPC was extrapolated from the mouse biodistribution data using SAAM II (Simulation Analysis and Modeling II) and OLINDA/EXM software. The data were analyzed commercially (RADAR, Inc).

1.3.11 Baboon PET Studies with [$^{11}$C]CPPC

Three 90-min dynamic PET scans (first: baseline; second: baseline after LPS treatment: third: LPS treatment-plus-blocking) were performed on a male baboon (*Papio anubis;* 25 kg) using the High Resolution Research Tomograph (CPS Innovations, Inc.). In brief, all PET scans were performed with an i.v. injection of 444-703 MBq (12-19 mCi) [$^{11}$C]CPPC [specific radioactivity: 1,096-1,184 GBq/μmol (29.6-32.0 Ci/μmol)]. In the LPS scans, the baboon was injected i.v. with 0.05 mg/kg LPS 4 h before the radiotracer. In the LPS-plus-blocking scan, the selective CSF1R inhibitor CPPC (1 mg/kg) was given s.c. 1.5 h before the radiotracer. Changes in the serum level of cytokine IL-6 were monitored with ELISA (FIG. 14). PET data analysis and radiometabolite analysis of baboon arterial blood are described in detail herein below.

1.3.12 Postmortem Human Bram Autoradiography

Use of human tissues has been approved by the Institutional Review Board of the Johns Hopkins Medical Institutions. Slices of inferior parietal cortex (20 μm) of three human subjects suffering from AD and one healthy control (see Table 5 for demographics) on glass slides were used for in vitro autoradiography. The baseline slides were probed with [$^{11}$C]CPPC, while blocking slides were probed with [$^{11}$C]CPPC plus blocker (CPPC, BLZ945, pexidartinib, or compound 8) to test CSF1R-binding specificity. The slides were exposed to X-ray film and analyzed with outcome expressed as pmol/$mm^3$ of wet tissue±SD.

TABLE 5

Demographic data related to the post-mortem human brain tissue that was used in the autoradiography study.

| Sample | Diagnosis | CERAD score | Braak score | Age | Sex | Race | Post-mortem delay, h |
|---|---|---|---|---|---|---|---|
| 1-AD | Alzheimer's | C | 6 | 88 | F | white | 8 |
| 2-AD | Alzheimer's | C | 6 | 58 | F | white | 8.5 |

TABLE 5-continued

Demographic data related to the post-mortem human brain tissue that was used in the autoradiography study.

| Sample | Diagnosis | CERAD score | Braak score | Age | Sex | Race | Post-mortem delay, h |
|---|---|---|---|---|---|---|---|
| 3-AD | Alzheimer's | C | 6 | 61 | M | white | 13.5 |
| 4-Ctrl | Healthy control | n/a | n/a | 48 | F | black | 12 |

1.4 Results 1.4.1 Chemistry

The precursor for radiolabeling, Pre-CPPC, was prepared in four steps with an overall yield of 54% (FIG. 7) in multimilligram amounts. Radiotracer [$^{11}$C]CPPC was prepared in a non-decay-corrected radiochemical yield of 21±8% (n=17), radiochemical purity >95%, and specific radioactivity at the end-of-synthesis of 977±451 GBq/μmol (26.4±12.2 Ci/μmol) (FIG. 9).

1.4.2 Regional Brain Biodistribution Studies in Control Mice

The regional brain uptake of [$^{11}$C]CPPC at various time points after injection of radiotracer is shown in Tables 1 and 2. A peak uptake value of 150% SUV was seen in the frontal cortex in 5-15 min after radiotracer injection. Between 30 and 60 min, which encompasses the 45-min time point of several studies described below, changes in % SUV were stable.

1.4.3 Evaluation of Specific Binding of [$^{11}$C]CPPC in Control Mice

1.4.3.1 Blocking Study

Figure 11:
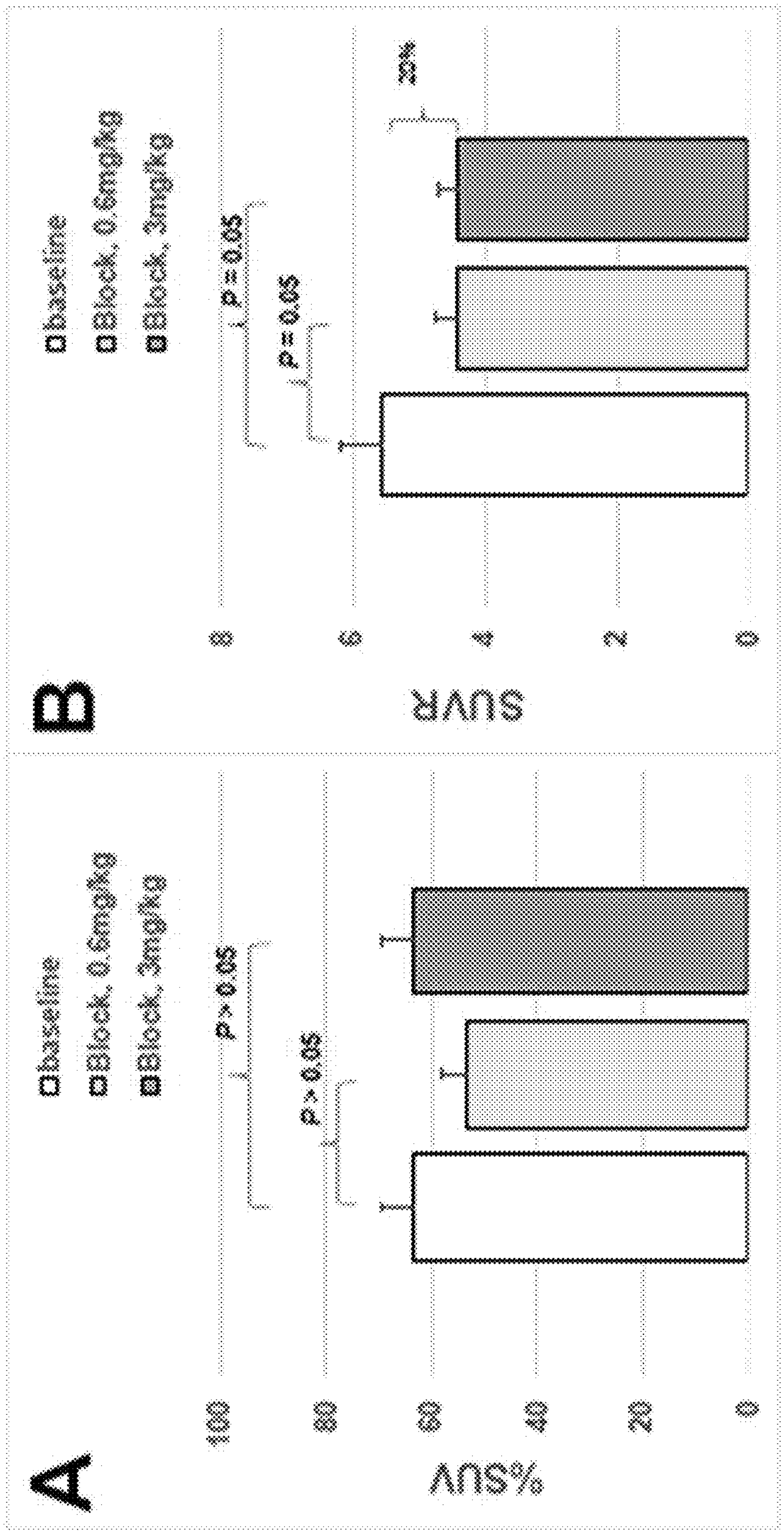

The blocking of [$^{11}$C]CPPC uptake was initially performed with escalating doses of nonradiolabeled CPPC (0.6-20 mg/kg). The study showed no reduction of the radiotracer % SUV uptake at low doses and a gradual trend toward increased uptake at high doses (FIG. 10). When brain uptake was corrected for the blood input function as SUVR, however, a significant blocking effect with 20% reduction of radioactivity was observed (FIG. 11).

1.4.3.2 Comparison of Normal Control Mice Vs. Microglia-Depleted Mice

The study showed a small (14%), but significant, reduction in radiotracer uptake in microglia-depleted mouse brain (FIG. 12A).

1.4.3.3 Comparison of Normal Control Mice Vs. CSF1R KO Mice

The study demonstrated comparable brain uptake (% SUV) of [$^{11}$C]CPPC in the KO mouse brain vs. controls (FIG. 12B).

1.4.4 Biodistribution of [$^{11}$C]CPPC in LPS-Induced Murine Models of Neuroinflammation These studies were performed in two murine LPS-induced neuroinflammation models: intracranial LPS (i.e.-LPS) (Dobos N, et al. (2012)) and i.p. LPS (i.p.-LPS) (Qin L, et al. (2007); Catorce M N and Gevorkian G (2016)). Initially, the induction of CSF1R expression in the brain of i.p.-LPS mice was examined and a twofold increase of Csf1r mRNA and a sixfold increase of the protein by qRT-PCR and Western blot analyses, respectively was found (FIG. 14).

1.4.4.1 i.e.-LPS Mice

Figure 1:
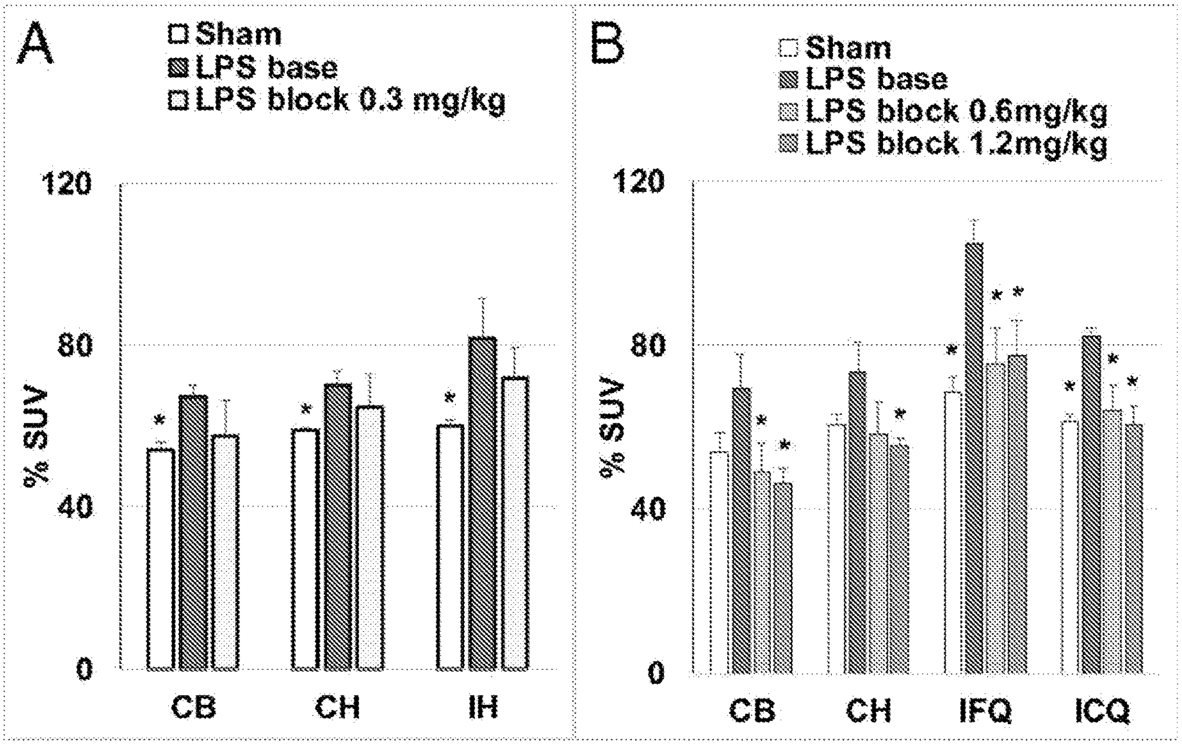

Two independent experiments were performed (FIG. 1). In both experiments, the increase in % SUV in the LPS mice relative to sham mice was significant, and it was higher in the ipsilateral hemisphere than that in the contralateral hemisphere. The greatest increase was observed in the ipsilateral frontal quadrant (53%), where LPS was injected (FIG. 1B). The blockade of [$^{11}$C]CPPC with nonradiolabeled CPPC was dose-dependent. The reduction of uptake in the first experiment was insignificant when a low dose of blocker (0.3 mg/kg) (FIG. 1A) was used. The higher doses of blocker (0.6 or 1.2 mg/kg) significantly reduced the uptake of [$^{11}$C]CPPC in the LPS-treated animals (FIG. 1B).

1.4.4.2 i.p.-LPS Mice

Three independent experiments were performed. In the first experiment in the i.p.-LPS mice, [$^{11}$C]CPPC manifested increased % SUV brain uptake (55%) relative to control animals, but the blocking with nonradiolabeled CPPC did not cause a significant reduction of the % SUV radioactivity in the LPS animals (FIG. 2A). In the second and third experiments, the % SUV uptake was corrected for blood radioactivity as SUVR (FIG. 2B and FIG. 2C). The SUVR uptake was significantly greater in the i.p.-LPS mice than controls. Blocking with two different CSF1R inhibitors, CPPC (FIG. 2B) and compound 8 (FIG. 2C), significantly decreased the uptake to the control level. Blood radioactivity concentration changed in the i.p.-LPS baseline (14% reduction) and i.p.-LPS blocking experiments (39% increase) vs. controls.

1.4.5 Brain Regional Distribution of [$^{11}$C]CPPC in a Transgenic Mouse Model of AD

[$^{11}$C]CPPC uptake was significantly higher in all brain regions of AD mice with greatest increase (31%) in the cortex (FIG. 3).

1.4.6 Whole-Body Radiation Dosimetry in Mice

Most organs received 0.002-0.006 mSv/MBq [0.007-0.011 Roentgen equivalent man (Rem)/mCi]. The small intestine received the highest dose of 0.047 mSv/MBq (0.17 Rem/mCi). The effective dose was 0.0048 mSv/MBq (0.018 Rem/mCi) (Table 3).

1.4.7 [$^{11}$C]CPPC PET/CT in the Murine EAE Model of Multiple Sclerosis

Figure 4:
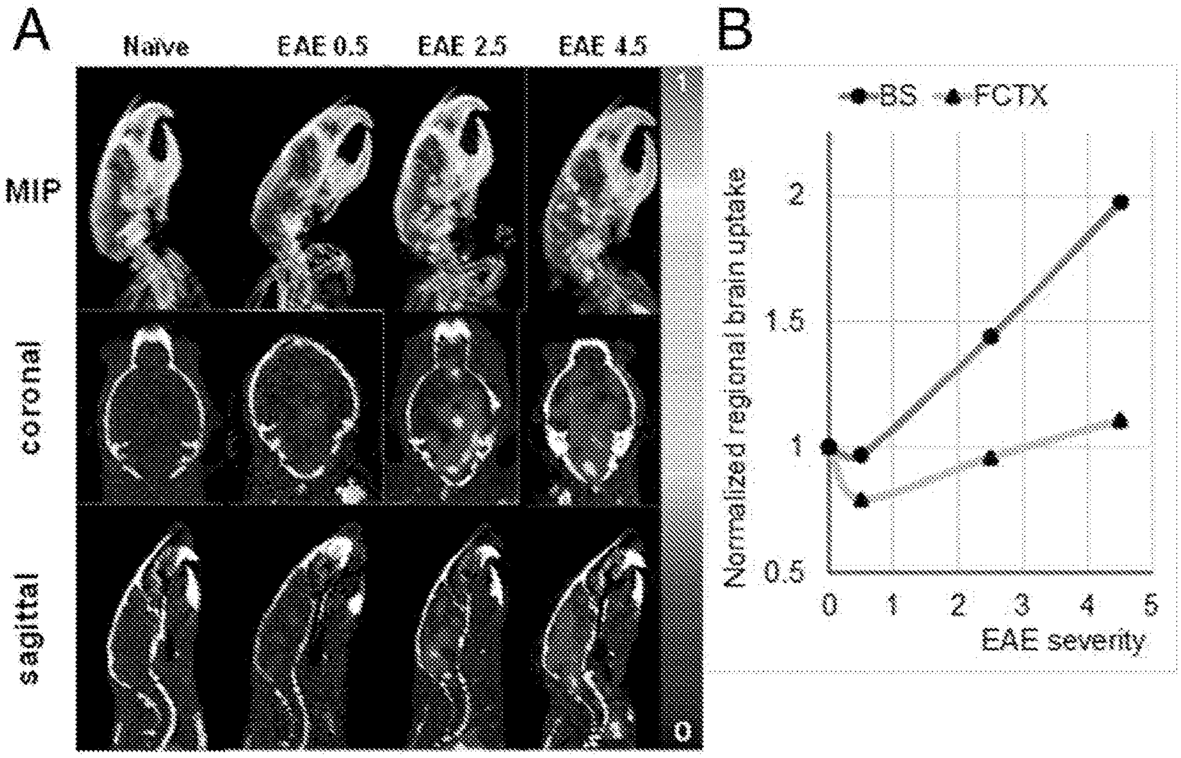

Three mice representing a spectrum of EAE severity (EAE scores of 0.5, 2.5, and 4.5) and a single healthy mouse receiving no antigen or adjuvant were injected with [$^{11}$C]CPPC and dynamically scanned using PET/CT (FIG. 4). The maximum intensity projection (MIP) images and sagittal slices of each mouse (FIG. 4A) show the radiotracer uptake intensity that correlates with disease severity with greatest increase (99%) in the brainstem (FIG. 4B), while muscle uptake was comparable between mice. The raw images without Harderian and salivary gland thresholding are shown in FIG. 13.

1.4.8 PET in Baboon

Comparison of the dynamic PET [$^{11}$C]CPPC scans in the same baboon in baseline, LPS, and LPS-plus-block experiments demonstrated an increase of parametric volume of distribution ($V_T$) after LPS treatment and reduction to the baseline level of the $V_T$ after LPS-plus-blocking treatment (FIG. 5 and FIG. 15). Serum levels of IL-6 strongly increased after the administration of LPS, suggesting successful induction of acute inflammation (FIG. 16).

Dynamic [$^{11}$C]CPPC PET baseline imaging in a baboon showed accumulation of radioactivity in the brain with a peak SUV of 2.5-4.0 at 20 min postinjection, followed by gradual decline (FIG. 5B). Regional $V_T$ was moderately heterogeneous, highest in the putamen, caudate, thalamus, and insula; intermediate in the frontal cortex; and lowest in the cerebellum, hypothalamus, and occipital cortex (FIG. 5A and FIG. 15).

Comparison of baboon PET at baseline vs. LPS vs. LPS-plus-blocking showed a small difference in SUV within brain. However, the washout rate in the baseline scan was more rapid than that in the LPS scan (FIG. 5C).

Figure 17:
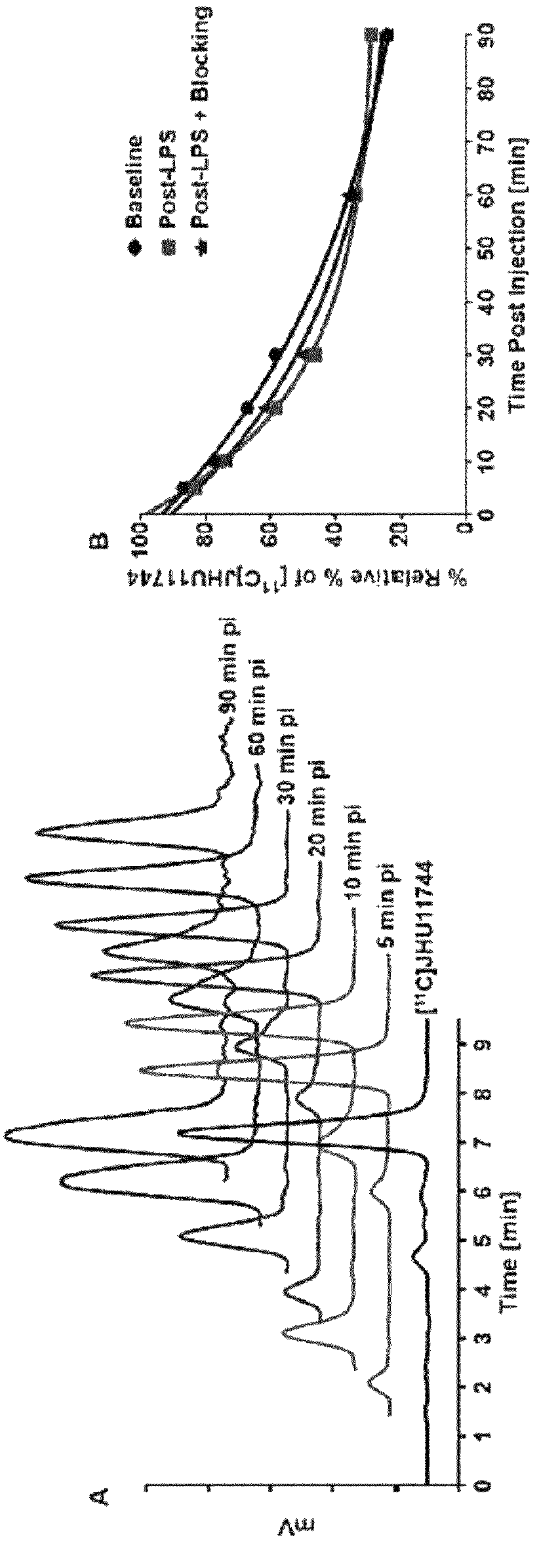

Radiometabolite analysis of blood samples from baboons showed that [$^{11}$C]CPPC was metabolized to two radiometabolites (71-76% total radiometabolites) at 90 min postinjection (FIG. 17). Those hydrophilic radiometabolites entered the brain minimally, as demonstrated in mouse experiments. Analysis by HPLC showed that at least 95% of the radioactivity in the mouse brain was the parent [$^{11}$C]CPPC (Table 4).

Metabolite-corrected [$^{11}$C]CPPC radioactivity in baboon plasma greatly decreased (~50%) in the LPS-treated vs. baseline, with recovery to baseline levels in the LPS-plus-blocking experiment (FIG. 5D). Mathematical modeling using compartmental and Logan analysis (FIG. 18) demonstrated a dramatic increase (90-120%) of parametric $V_T$ values in the LPS-treated baboon ($V_T$=35-52) vs. baseline ($V_T$=15-25), with a return to the baseline level in the LPS-plus-blocking study (FIG. 5 and FIG. 15), whereas the $K_1$ value changed only slightly (FIG. 19). The increase of radiotracer binding in the LPS-treated baboon brain was CSF1R-specific, as demonstrated on the blocking scan.

1.4.9 Postmortem Autoradiography of [$^{11}$C]CPPC in Human Brain

The comparison of [$^{11}$C]CPPC baseline autoradiography in the AD vs. control brain slices (FIG. 6 and Table 6) showed an increase (75-99%) of radiotracer binding in the AD brain. The binding specificity was tested by comparing the baseline binding with binding in blocking experiments using four different CSF1R inhibitors. The baseline/blocking ratio in the AD brain was 1.7-2.7 (blocker: CPPC), whereas in the control brain the ratio was 1.4 (FIG. 6 and Table 6). When other CSF1R blockers (compound 8, BLZ945, and PLX3397) were used in the same AD brains, the baseline/blocking ratios were 2.0±0.23, 1.79±0.88, and 1.25±0.25, respectively (FIG. 20).

TABLE 6

Autoradiography binding (pmol/mm3) of [11C]CPPC in the AD and healthy control post-mortem human brain slices (see also FIG. 13)

| Sample | 1-AD | 2-AD | 3-AD | 4-control |
|---|---|---|---|---|
| Baseline | 8.18 ± 0.68 | 7.20 ± 1.55 | 7.43 ± 1.59 | 4.11 ± 1.14 |
| Blocking with unlabeled CPPC | 4.72 ± 1.07 | 2.67 ± 0.53 | 3.73 ± 1.07 | 2.86 ± 1.06 |

1.5 Discussion

The presently disclosed subject matter provides a PET radiotracer specific for CSF1R in vitro in human brain tissue and in vivo in nonhuman primate and murine models of neuroinflammation. While researchers [see Tronel C, et al. (2017); Janssen B, et al. (2018)] have worked to develop and implement PET biomarkers for neuroinflammation, none has proved selective to microglia, the resident immune cells of the brain, until [$^{11}$C]CPPC.

The lead CSF1R inhibitor for development of [$^{11}$C]CPPC was selected from the literature (Illig C R, et al. (2008)). Original, nonradiolabeled CPPC exhibited high CSF1R inhibitory potency [$IC_{50}$=0.8 nM (Illig C R, et al. (2008))] and suitable physical properties for brain PET, including optimal lipophilicity with a calculated partition coefficient (c log $D_{7.4}$) of 1.6 and molecular mass of 393 Da, which portend blood-brain barrier permeability. [$^{11}$C]CPPC was prepared in suitable radiochemical yield with high purity and specific radioactivity (FIG. 9).

1.5.1 Biodistribution and Specific Binding of [$^{11}$C]CPPC Studies in Control Mice Brain uptake of [$^{11}$C]CPPC in control mice was robust, with a peak of 150% SUV or 6.4% ID/g tissue in frontal cortex, followed by a decline (Table 2). The regional brain distribution was moderately heterogeneous, with the highest accumulation of radioactivity in frontal cortex, in agreement with analysis of CSF1R expression in normal mouse brain (Nandi S, et al. (2012)). Among brain regions studied here, the brainstem and cerebellum showed the lowest accumulation of CSF1R binding specificity of [$^{11}$C]CPPC in normal mouse brain was evaluated using three approaches: comparison of baseline controls with (1) blocking, (ii) microglia-depleted, and (iii) CSF1R KO mice. The initial dose-escalation blocking study in normal mouse brain failed to show a significant reduction of % SUV (FIG. 9 and FIG. 10A). However, when the % SUV was corrected for radioactivity in the blood as SUVR, a moderate, but significant, reduction (20%) was observed (FIG. 10B), demonstrating that [$^{11}$C]CPPC specifically labels CSF1R in normal mouse brain. That [$^{11}$C]CPPC concentration in blood was greater in the blocking studies also is noteworthy.

Chronic treatment of mice with the CSF1R inhibitor PLX3397 (pexidartinib) effectively depletes microglia (90%) and reduces CSF1R in the animal brain (Elmore M R, et al. (2014)). Brain uptake of [$^{11}$C]CPPC in the microglia-depleted mice was lower (14%) than in controls (FIG. 12A). That reduced uptake may be due to a combination of two effects, namely, depletion of microglia and the blocking effect of PLX3397 per se. Finally, the comparison of [$^{11}$C]CPPC uptake in the control and CSF1R KO mice showed comparable radiotracer uptake to the control and KO mice (FIG. 12B). While depleted (PLX3397) or absent (KO) CSF1R target indicates that there should be little to no brain uptake of a CSF1R-specific imaging agent, there is only modest expression of CSF1R in healthy rodent brain (Nandi S, et al. (2012); Michaelson M D, et al. (1996); and Lee S C, et al. (1993)), necessitating attention to relevant animal models where CSF1R would be present in higher amounts.

1.6.2 Evaluation of [$^{11}$C]CPPC in Murine Models of LPS-Induced Neuroinflammation LPS stimulation is a common model of neuroinflammation (Qin L, et al. (2007); Catorce M N and Gevorkian G (2016)). LPS-induced neuroinflammation was used for testing various PET radiotracers in rodents, nonhuman primates, and even human subjects [see Tronel C, et al. (2017)]. Reports describing CSF1R expression in LPS neuroinflammation models are not available. The CSF1R levels in the brain of the i.p.-LPS mice vs. control mice were compared using qRT-PCR and Western blot and a high increase of Csf1r mRNA and CSF1R protein expression was found (FIG. 14). In this study, two murine models of LPS-induced neuroinflammation, i.e.-LPS (Dobos N, et al. (2012); Aid S, et al. (2010) and i.p.-LPS (Qin L, et al. (2007), Catorce M N and Gevorkian G (2016), were used. Even though stereotactic surgery may damage the blood-brain barrier in the i.c-LPS animals, this model, which produces localized neuroinflammation, initially appeared more attractive than the i.p-LPS model with diffused neuroinflammation. However, further studies with [$^{11}$C]CPPC showed comparable results using both models.

Figure 2:
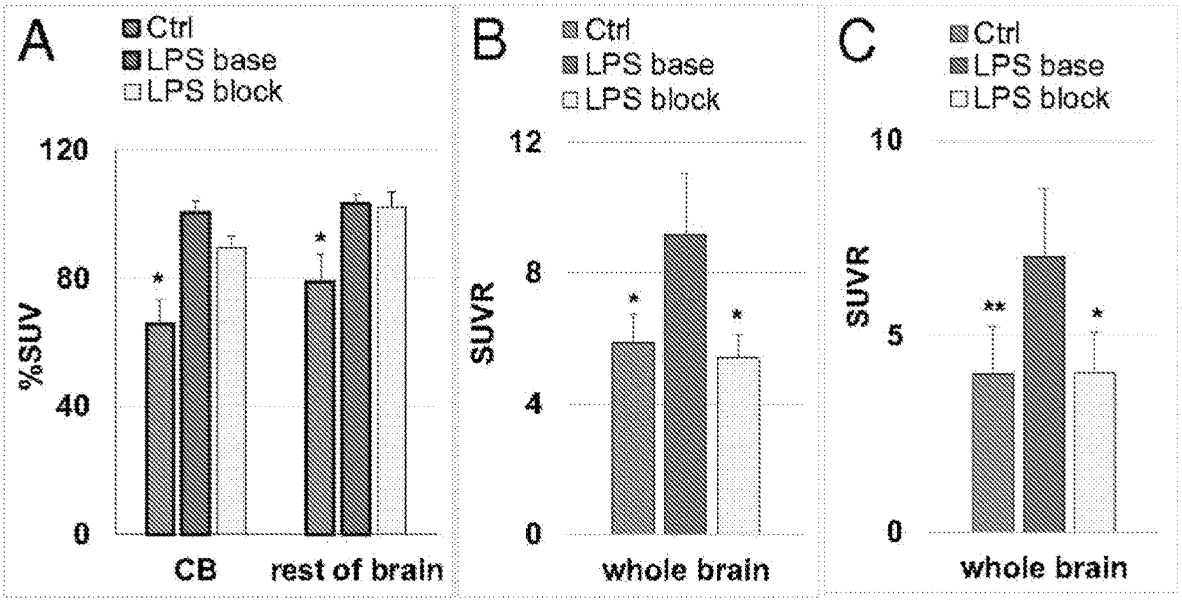

[$^{11}$C]CPPC-binding experiments demonstrated a significant elevation (up to 53%) of uptake in i.e.-LPS mice (FIG. 1). The elevated binding was ~50% specific vs. sham animals and mediated through CSF1R, as demonstrated in the dose-escalation blocking experiments (FIG. 1). In the i.p.-LPS mice, [$^{11}$C]CPPC binding was also significantly higher (up to 55-59%) vs. control animals (FIG. 2). Whole-brain [$^{11}$C]CPPC binding in the i.p.-LPS mice was more than 50% specific and mediated through CSF1R, as demonstrated in blocking experiments using two different CSF1R inhibitors, CPPC (FIG. 2B) and compound 8 (FIG. 2C). In the i.p.-LPS animals, the blood radioactivity concentration changed dramatically, necessitating the correction of % SUV for the blood input function as SUVR (FIG. 2B and FIG. 2C). The blood radioactivity changes may be explained by unavoidable systemic changes of CSF1R levels in the i.p.-LPS mice. The [$^{11}$C]CPPC studies in the intracranial and i.p. murine LPS models showed comparable results demonstrating that the radiotracer specifically labels CSF1R in both models. The ex vivo binding potential ($BP_{ex\ vivo}$=0.53-0.62) of [$^{11}$C]CPPC in the LPS mice was estimated as LPS uptake -sham uptake/sham uptakeLPS uptake -sham uptake/sham uptake. A previous study in LPS-treated rats with the TSPO radiotracer [$^{11}$C]PK11195 gave a comparable BP value of 0.47 (Dickens A M, et al. (2014)).

1.5.3 [$^{11}$C]CPPC Imaging of EAE Mice

PET/CT imaging in the C57BL/6 $MOG_{35-55}$ EAE model showed that the PET signal intensity was proportional to disease score (FIG. 4) and largely concentrated in the brainstem, cerebellum, and cervical spine, in agreement with the regional distribution of demyelination in the EAE model. The brainstem uptake of [$^{11}$C]CPPC was up to twofold greater in the BAB mice vs. control animals.

1.5.4 Whole-Body Radiation Dosimetry in Mice

Dosimetry was performed for future translation of [$^{11}$C]CPPC to humans. The mouse study demonstrated that a proposed dose of 740 MBq (20 mCi) [$^{11}$C]CPPC administered to a human subject would result in a radiation burden below the current Food and Drug Administration limit (5 Rem; (5. Federal Register § 361.1 (2018)), but an actual study in human subjects is needed to confirm this estimate.

1.5.5 PET Imaging in Baboon

Systemic administration of LPS to baboon causes microglial activation (Hannestad J, et al. (2012)). In this report, binding properties of [$^{11}$C]CPPC were tested in a control baboon and in the same baboon injected with a low dose of LPS (0.05 mg/kg, i.v.). More than a twofold increase of distribution volume ($V_T$) values was observed in all brain regions of the LPS-treated animal (FIG. 5 and FIG. 15). The increase of parametric $V_T$ in the LPS-baboon was fully blocked by injection of nonradiolabeled CPPC (FIG. 5A and FIG. 15). The parametric modeling of those images is essential because injection of LPS and blocker cause changes in the blood input function (FIG. 5D), most likely due to CSF1R changes in the periphery. Parametric modeling did not require inclusion of brain radiometabolites, because HPLC analysis showed mostly unchanged parent [$^{11}$C]CPPC in the animal brain (>95%)

[$^{11}$C]CPPC PET scans demonstrated that radiotracer binding in the LPS-treated baboon brain was specific and mediated by CSF1R, rendering this agent suitable for imaging of neuroinflammation in nonhuman primates. The increase of [$^{11}$C]CPPC $V_T$ (85-120%) in the baboon treated with LPS (0.05 mg/kg) was at least the same or higher than that for the TSPO radiotracer [$^{11}$C]PBR28 (range, 35.6-100.7%) in response to a greater dose of LPS (0.1 mg/kg), as shown in a previous report (Hannestad J, et al. (2012)). Accordingly, [$^{11}$C]CPPC might provide an innovative tool with high sensitivity for quantitative imaging of activated microglia in neuroinflammation.

1.5.6 [$^{11}$C]CPPC Binding in AD Brain

There is an immune component to AD, particularly involving the innate immune system, which is different from "typical" neuroinflammatory diseases, such as multiple sclerosis or several of the models described above (Heppner F L, et al. (2015)). Previous research provided evidence of up-regulation of CSF1R in the brains of human subjects suffering from AD (Akiyama H, et al. (1994); Walker D G, et al. (2017); Lue L F, et al. (2001)) and in transgenic mouse models of AD (Murphy G M Jr, et al., (2000); Yan S D, et al. (1997); and Boissonneault V, et al. (2009)). The binding of [$^{11}$C]CPPC was tested in transgenic AD mouse brain and in postmortem AD human brain tissue. In agreement with previous data (Murphy G M Jr, et al., (2000); Yan S D, et al. (1997); and Boissonneault V, et al. (2009)), the ex vivo brain uptake of [$^{11}$C]CPPC in transgenic AD mice was significantly higher (up to 31%) than that in control animals (FIG. 3).

Postmortem human in vitro autoradiography showed that [$^{11}$C]CPPC specifically labeled CSF1R in the AD brain (baseline/self-blocking ratio up to 2.7) (FIG. 6 and Table 6). In a separate experiment, CSF1R inhibitors, structurally different from CPPC [compound 8, $IC_{50}$=0.8 nM (Illig C R, et al. (2008)); BLZ945, $IC_{50}$=1.2 nM (Krauser J A, et al. (2015)); and PLX3397, $IC_{50}$=20 nM (DeNardo D G, et al. (2011))], blocked [$^{11}$C]CPPC binding in the same AD tissue (FIG. 20), confirming that binding was CSF1R-specific (FIG. 6, FIG. 20, and Table 6. The baseline/blocking ratios for more potent CSF1R inhibitors, namely, compound 8 and BLZ945, were up to two times greater than that of less potent PLX3397. Those findings may be extended to imaging other neurodegenerative disorders or conditions with an innate immune component, such as amyotrophic lateral sclerosis, aging, or Parkinson's disease (Deczkowska A, et al. (2018)), which involve DAM. [$^{11}$C]CPPC may also provide an indirect imaging readout for TREM2 signaling (Deczkowska A, et al. (2018); Hickman S E and El Khoury J (2014)), which has not been imaged in vivo.

1.6 Summary

The presently disclosed subject matter provides, in part, [$^{11}$C]CPPC, a PET radiotracer for imaging CSF1R in neuroinflammation. Specific binding of the radiotracer is increased in mouse (up to 59%) and baboon (up to 120%) models of LPS-induced neuroinflammation, murine models of AD (31%) and multiple sclerosis (up to 100%), and in postmortem AD human brain tissue (base/block ratio of 2.7). Radiation dosimetry studies in mice demonstrated that [$^{11}$C]CPPC is safe for human studies. [$^{11}$C]CPPC radiometabolites minimally enter the animal brain, indicating that their inclusion in image analysis is not required. [$^{11}$C]CPPC is poised for clinical translation to study CSF1R in a variety of clinical scenarios.

1.7 Supplemental Material and Methods 1.7.1 CSF1R Inhibitors

BLZ945 (Krauser J A, et al. (2015)) was purchased from AstaTech (Bristol, PA), pexidartinib (PLX3397) (DeNardo D G, et al. (2011)) from eNovation Chemicals (Bridgewater, NJ) and compound 8 was prepared inhouse as described previously (Illig C R, et al. (2008)).

1.7.2 Chemistry $^1$H NMR spectra were recorded with a Bruker-500 NMR spectrometer at nominal resonance frequencies of 500 MHz in $CDCl_3$, $CD_3OD$ or DMSO-$d_6$ (referenced to internal $Me_4Si$ at δ 0 ppm). High-resolution mass spectra were recorded commercially utilizing electrospray ionization (ESI) at the University of Notre Dame Mass Spectrometry facility.

Synthesis of 5-Cyano-N-(4-(4-methylpiperazin-1-yl)-2-(piperidin-1-yl)phenyl)furan-2-carboxamide (CPPC) was performed as described elsewhere (Illig C R, et al. (2008)).

1-(5-Chloro-2-nitrophenyl)piperidine: To a cooled (0 °C) solution of 1.0 g (10.0 mmol) of 4-chloro-2-fluoronitrobenzene in 15 mL of EtOH was added 1.7 mL (30.0 mmol) of piperidine dropwise over 5 min. The solution stirred at 0 °C for 10 min and then at 23 °C for 30 min. The mixture was poured into water (225 mL) and extracted with EtOAc (2×30 mL). The combined extracts were washed with saturated aq $NaHCO_3$ and brine (30 mL each) and then dried over $Na_2SO_4$ and evaporated to get the crude compound. The resulting residue was purified by silica gel column chromatography (Hexane:EtOAc=9.5:0.5) to give 1-(5-chloro-2-nitrophenyl)piperidine as a yellow solid (1.32 g, 96% yield). $^1$H NMR (500 MHz, $CDCl_3$) δ 7.77 (d, J=5.0 Hz, 1H), 7.13 (s, 1H), 6.93 (d, J=10.0 Hz, 1H), 3.30-3.27 (m, 2H), 2.91-2.86 (m, 2H), 1.90-1.86 (m, 1H), 1.75-1.73 (m, 2H), 1.49-1.42 (m, 1H).

1-Methyl-4-(4-nitro-3-(piperidin-1-yl)phenyl)piperazine: A mixture of 1-(5-chloro-2-nitrophenyl)piperidine (1.0 g, 4.15 mmol) and 1-methylpiperazine (1.38 mL, 12.46 mmol) were heated with stirring under $N_2$ at 138 °C for 12 h. After cooling to rt, the mixture was poured into water and extracted with ethyl acetate (2×100 mL). The combined extracts were washed with water and brine and then dried over $Na_2SO_4$ and evaporated to get the crude compound. The resulting residue was purified by silica gel column chromatography ($CH_2Cl_2$:MeOH=9:1) to give 1-methyl-4-(4-nitro-3-(piperidin-1-yl)phenyl)piperazine as a yellow solid (1.2 g, 96% yield). $^1$H NMR (500 MHz, $CDCl_3$) δ 7.62 (d, J=5.0 Hz, 1H), 6.80 (s, 1H), 6.43 (d, J=10.0 Hz, 1H), 3.84 (t, J=5.0 Hz, 4H), 3.71 (t, J=5.0 Hz, 2H), 3.60 (t, J=5.0 Hz, 4H), 3.50 (d, J=10.0 Hz, 2H), 3.80 (d, J=5.0 Hz, 2H), 1.55-1.51 (m, 3H).

4-(4-methylpiperazin-1-yl)-2-(piperidin-1-yl)aniline: To a mixture of 1-methyl-4-(4-nitro-3-(piperidin-1-yl)phenyl) piperazine (1.2 g, 3.94 mmol), and $NH_4Cl$ (2.10 g, 39.4 mmol) in THF/MeOH/$H_2O$ (10:5:3) (20 mL), was added Zn dust (2.57 g, 39.4 mmol) at 90 °C, then the mixture was refluxed for 1 h. After completion of the reaction, the reaction mixture was filtered through Celite and partitioned between EtOAc and brine. The organic layer was separated, dried over anhydrous $MgSO_4$, filtered, and concentrated in vacuo. The resulting residue was purified by silica gel column chromatography ($CH_2Cl_2$:MeOH=9:1) to give 4-(4-methylpiperazin-1-yl)-2-(piperidin-1-yl)aniline as a brown solid (0.98 g, 90.7% yield).

5-Cyano-N-(4-(4-methylpiperazin-1-yl)-2-(piperidin-1-yl)phenyl)furan-2-carboxamide (CPPC): To the mixture of 4-(4-methylpiperazin-1-yl)-2-(piperidin-1-yl)aniline (0.5 g, 1.82 mmol), 5-cyanofuran-2-carboxylic acid (0.3 g, 2.18 mmol), HATU (0.83 g, 2.18 mmol), in DMF (10 mL) was added DIPEA (0.63 mL, 3.64 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give 5-cyano-N-(4-(4-methylpiperazin-1-yl)-2-(piperidin-1-yl)phenyl)furan-2-carboxamide as a yellow solid (0.6 g, 84.5% yield). $^1$H NMR (500 MHz, $CDCl_3$) δ 9.53 (s, 1H), 8.31 (d, J=8.7 Hz, 1H), 7.23 (d, J=16.6 Hz, 2H), 6.80 (s, 1H), 6.72 (d, J=8.8 Hz, 1H), 3.20 (s, 4H), 2.85 (s, 4H), 2.59 (s, 4H), 2.36 (s, 3H), 1.80 (s, 4H), 1.65 (s, 2H). HRMS calculated for $C_{22}H_{28}N_5O_2$ ([M+H])394.223752, found 394.223065.

Synthesis of 5-Cyano-N-(4-(piperazin-1-yl)-2-(piperidin-1-yl)phenyl)furan-2-carboxamide (Pre-CPPC)

Referring now to FIG. 8 is the synthesis of 5-Cyano-N-(4-(piperazin-1-yl)-2-(piperidin-1-yl)phenyl)furan-2-carboxamide (Pre-CPPC):

Step a. Tert-butyl 4-(4-nitro-3-(piperidin-1-yl)phenyl)piperazine-1-carboxylate: To the mixture of 1-(5-chloro-2-nitrophenyl)piperidine (1.0 g, 4.15 mmol) and tert-butyl piperazine-1-carboxylate (1.55 g, 8.30 mmol), in DMSO (10 mL) was added $K_2CO_3$ (1.72 g, 12.45 mmol). The reaction mixture was stirred at 110 °C for 12 h and then partitioned between EtOAc and brine. The organic layer was separated, dried over anhydrous $MgSO_4$, filtered, and concentrated under a vacuum. The resulting residue was purified by silica gel column chromatography (Hexane:EtOAc=3:7) to give tert-butyl 4-(4-nitro-3-(piperidin-1-yl)phenyl)piperazine-1-carboxylate as a white solid (1.40 g, 86.4% yield). $^1$H NMR (500 MHz, $CDCl_3$) δ 7.99 (d, J=10.0 Hz, 1H), 6.38 (d, J=10.0 Hz, 1H), 6.31 (s, 1H), 3.58 (t, J=5.0 Hz, 4H), 3.34 (t, J=5.0 Hz, 4H), 2.28 (t, J=5.0 Hz, 2H), 2.78 (d, J=10.0 Hz, 2H), 1.70 (d, J=5.0 Hz, 2H), 1.55-1.51 (m, 3H), 1.47 (s, 9H).

Step b. Tert-butyl 4-(4-amino-3-(piperidin-1-yl)phenyl) piperazine-1-carboxylate: To a mixture of tert-butyl 4-(4-nitro-3-(piperidin-1-yl)phenyl)piperazine-1-carboxylate (1.20 g, 3.07 mmol), and $NH_4Cl$ (1.64 g, 30.7 mmol) in THF/MeOH/$H_2O$ (10:5:3) (20 mL), was added Zn dust (2.0 g, 30.7 mmol) at 90 °C, then the mixture was refluxed for 1 h. After completion of the reaction, the reaction mixture was filtered through Celite and partitioned between EtOAc and brine. The organic layer was separated, dried over anhydrous $MgSO_4$, filtered, and concentrated in vacuo. The resulting residue was purified by silica gel column chromatography ($CH_2Cl_2$:MeOH=9:1) to give tert-butyl 4-(4-amino-3-(piperidin-1-yl)phenyl)piperazine-1-carboxylate as a brown solid (1.0 g, 90.3% yield).

Step c. Tert-butyl 4-(4-(5-cyanofuran-2-carboxamido)-3-(piperidin-1-yl)phenyl)piperazine-1-carboxylate: To the mixture of tert-butyl 4-(4-amino-3-(piperidin-1-yl)phenyl) piperazine-1-carboxylate (0.5 g, 1.38 mmol), 5-cyanofuran-2-carboxylic acid (0.23 g, 1.66 mmol), HATU (0.63 g, 1.66 mmol), in DMF (10 mL) was added DIPEA (0.48 mL, 2.76 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give tert-butyl 4-(4-(5-cyanofuran-2-carboxamido)-3-(piperidin-1-yl)phenyl)piperazine-1-carboxylate as a yellow solid (0.60 g, 90.9% yield). $^1H$ NMR (500 MHz, $CDCl_3$) δ 9.59 (s, 1H), 8.31 (d, J=5.0 Hz, 1H), 7.25 (d, J=5.0 Hz, 1H), 7.21 (d, J=5.0 Hz, 1H), 6.79 (s, 1H), 6.72 (d, J=5.0 Hz, 1H), 3.58 (t, J=5.0 Hz, 4H), 3.10 (t, J=5.0 Hz, 4H), 2.99 (t, J=5.0 Hz, 2H), 2.72 (t, J=10.0 Hz, 2H), 1.83 (d, J=10.0 Hz, 2H), 1.55-1.51 (m, 3H), 1.49 (s, 9H).

Step d. 5-Cyano-N-(4-(piperazin-1-yl)-2-(piperidin-1-yl) phenyl)furan-2-carboxamide (Pre-CPPC): To a solution of tert-butyl 4-(4-(5-cyanofuran-2-carboxamido)-3-(piperidin-1-yl)phenyl)piperazine-1-carboxylate (0.5 g, 1.04 mmol) in methylene chloride (5 mL) was added trifluoroacetic acid (0.39 mL, 5.21 mmol) dropwise at 0 °C, and then, the mixture was stirred at room temperature for 12 h. After completion of the reaction, the reaction mixture was concentrated under reduced pressure. The resulting residue was purified by silica gel column chromatography ($CH_2Cl_2$: MeOH=9:1) to give 5-cyano-N-(4-(piperazin-1-yl)-2-(piperidin-1-yl)phenyl)furan-2-carboxamide as a pale yellow solid (0.3 g, 76.0% yield). $^1H$ NMR (500 MHz, $CDCl_3$) δ 9.60 (s, 1H), 8.31 (d, J=5.0 Hz, 1H), 7.25 (d, J=5.0 Hz, 1H), 7.21 (d, J=5.0 Hz, 1H), 6.79 (s, 1H), 6.72 (d, J=5.0 Hz, 1H), 3.15 (t, J=5.0 Hz, 4H), 3.08 (t, J=5.0 Hz, 4H), 2.99 (t, J=5.0 Hz, 2H), 2.73 (t, J=10.0 Hz, 2H), 1.84 (d, J=10.0 Hz, 2H), 1.57 (s, 1H), 1.55-1.51 (m, 3H); HRMS calculated for $C_{21}H_{26}N_5O_2$ ([M+H)]380.208102, found 380.207980.

Referring now to FIG. 9, is the radiosynthesis of [$^{11}C$] CPPC:

To a 1 mL V-vial, Pre-CPPC (1 mg) was added to 0.2 mL of anhydrous DMF. [$^{11}C$]Methyl iodide, carried by a stream of helium, was trapped in the above mentioned solution. The reaction was heated in 80 °C for 3.5 min, then quenched with 0.2 mL of water. The crude reaction product was purified by reverse-phase high performance liquid chromatography (HPLC) at a flow rate of 12 mL/min. The radiolabeled product ($t_R$=6.5-7.2 min) that was fully separated from the precursor ($t_R$=2.5 min) was remotely collected in a solution of 0.3 g sodium ascorbate in a mixture of 50 mL water with 1 mL 8.4% aq. $NaHCO_3$. The aqueous solution was transferred through an activated Waters Oasis Sep-Pak light cartridge (Milford, MA). After washing the cartridge with 10 mL saline, the product was eluted with 1 mL of ethanol through a 0.2 μM sterile filter into a sterile, pyrogen-free vial and 10 mL of 0.9% saline was added through the same filter. The final product, [$^{11}C$]CPPC, was analyzed by analytical HPLC to determine the radiochemical purity and specific radioactivity.

1.7.3 HPLC Conditions

Preparative: Column, XBridge C18, 10×250 mm (Waters, Milford, MA). Mobile phase: 45%:55% acetonitrile:triethylamine-phosphate buffer, pH 7.2. Flow rate: 12 mL/min, retention time 7 min. Analytical: Column, Luna C18, 10 micron, 4.6×250 mm (Phenomenex, Torrance, CA). Mobile phase: 60%:40% acetonitrile: 0.1M aq. ammonium formate. Flow rate: 3 mL/min, retention time 3.5 min.

1.8.4 Biodistribution and PET Imaging Studies with [$^{11}C$] CPPC in Mice

TABLE 1

Summary of [11C]CPPC biodistribution and other studies in mice

| Study | Mice (number of animals) | Blocker (doses) | FIG. or Table |
|---|---|---|---|
| Controls, Baseline | C57BL/6J (3 per time point; Total: 12) | — | Table 2 |
| Controls, blocking - dose escalation | CD1 (5 per dose; Total: 30) | CPPC (0-20 mg/kg, IP) | FIG. 10 |
| Controls, baseline vs blocking, without blood (FIG. S5A) and with blood correction (FIG. S5B) | CD1 (3 per group; Total: 9) | CPPC (0, 0.6 or 3.0 mg/kg, IP) | FIG. 11 |
| Controls vs microglia-depleted | C57BL/6J (5 per group: 10 total) | PLX3397 (290 mg/kg chow) | FIG. 12A |
| Controls vs CSF1R-KO | Controls - C57BL/6J (5), CSF1R-KO - B6.Cg-Csf1r$^{tm1.2/Jwp}$/J (5) Total: 10 | — | FIG. 12B |
| Controls vs LPS (intracranial) Experiment 1 | Sham baseline - CD1 (3) LFS baseline - CD1 (3) LPS block - CD1 (3) Total: 9 | CPPC (0.3 mg/kg; IP) | FIG. 1A |
| Controls vs LPS (intracranial) Experiment 2 | Sham - CD1 (4) LPS baseline - CD1 (4) LPS block-1 - CD1 (4) LPS block-2 - CD1 (4) Total mice: 16 | Block-1: CPPC (0.6 mg/kg, IP) Block-2: CPPC (1.2 mg/kg, IP) | FIG. 1B |
| Controls vs LPS (IP) Experiment 1 | Controls - CD1 (5), IP LPS mice baseline - CD1 (5) IP LPS mice blocking - CD1 (5) Total mice: 15 | CPPC (1 mg/kg, IP) | FIG. 2A |
| Controls vs LPS (IP) Experiment 2 | Controls - CD1 (5), IP LPS mice baseline - CD1 (5) IP LPS mice blocking - CD1 (5) Total mice: 15 CD1 (6) Total mice: 15 | CPPC (1 mg/kg, IP) | FIG. 2B |

TABLE 1-continued

| Summary of [11C]CPPC biodistribution and other studies in mice | | | |
|---|---|---|---|
| Study | Mice (number of animals) | Blocker (doses) | FIG. or Table |
| Controls vs Alzheimer's mouse model | Controls - (6)<br>Transgenic APP - (6)<br>Total mice: 12 | — | FIG. 3 |
| Full body radiation dosimetry | CD1 (3 per time point)<br>Total: 15 | — | Table 3 |
| PET/CT, EAE mice | EAE mice (3)<br>Control (1)<br>Total: 4 | — | FIG. 4<br>FIG. 13 |
| Radiometabolites in mouse plasma and brain | CD1 (3 per time point)<br>Total: 6 | — | Table 4 |
| PCR and Western blot of LPS mouse brains | Controls - CD1 (6)<br>LPS i.p. treated - CD1 (6)<br>Total: 12 | — | FIG. 14 |

1.7.5 Brain Regional Distribution of [$^{11}$C]CPPC in Normal Control Mice, Baseline Male C57BL/6J mice of four to eight weeks of age, weighing 22-24 g from Charles River Laboratories (Wilmington, MA) were used. Animals were sacrificed by cervical dislocation at 5, 15, 30 and 60 min (3 mice per time-point) following injection of 5.6 MBq (0.15 mCi) [$^{11}$C]CPPC [specific radioactivity=462 GBq/μmol (12.5 Ci/μmol)] in 0.2 mL saline into a lateral tail vein. The brains were removed and dissected on ice. The brain regions (cerebellum, olfactory bulbs, hippocampus, frontal cortex, brain stem and rest of brain) were weighed and their radioactivity content was determined in a γ-counter LKB/Wallac 1283 CompuGamma CS (Bridgeport, CT). The percentage of standardized uptake value (% SUV) was calculated (Table 2).

TABLE 2

| Regional brain distribution of [11C]CPPC in control mice after radiotracer injection: SUV ± SD (n = 3) | | | | |
|---|---|---|---|---|
| | 5 min | 15 min | 30 min | 60 min |
| Cerebellum | 138 ± 9 | 110 ± 17 | 70 ± 4 | 71 ± 3 |
| Olfactory bulbs | 142 ± 12 | 124 ± 21 | 86 ± 9 | 90 ± 3 |
| Hippocampus | 124 ± 4 | 121 ± 25 | 94 ± 12 | 95 ± 3 |
| Frontal Cortex | 147 ± 8 | 150 ± 30 | 102 ± 16 | 107 ± 8 |
| Brain stem | 120 ± 19 | 106 ± 17 | 75 ± 11 | 70 ± 3 |
| Rest of brain | 137 ± 7 | 118 ± 21 | 81 ± 7 | 82 ± 3 |

1.7.6 Evaluation of Specific Binding of [$^{11}$C]CPPC in Control Mice 1.7.6.1 Brain Regional Distribution of [$^{11}$C]CPPC in Normal Control Mice, Dose Escalation Blocking Study with Unlabeled CPPC (FIG. 10)

Male CD-1 mice (26-28 g, age=six to seven weeks) from Charles River Laboratories were used. The CPPC solution (0.3, 0.6, 1.2, 3.0, 10, and 20 mg/kg) was given IP 5 min before IV [$^{11}$C]CPPC, whereas baseline animals received vehicle (n=5 per dose). Animals were sacrificed by cervical dislocation at 45 min following injection of 5.1 MBq (0.14 mCi) [$^{11}$C]CPPC [specific radioactivity=511 GBq/μmol (13.8 Ci/μmol)] in 0.2 mL saline into a lateral tail vein. The whole brains were removed, weighed and their radioactivity content was determined in a γ-counter LKB/Wallac 1283 CompuGamma CS (Bridgeport, CT). The percentage of standardized uptake value (% SUV) was calculated.

1.7.7 Comparison of Baseline and Blocking Uptake of [$^{11}$C]CPPC in the Same Experiment without and with Blood Correction (FIG. 11)

Male CD-1 mice (25-27 g, age=six to seven weeks) from Charles River Laboratories were used. The CPPC solutions (0.6 or 3.0 mg/kg) was given IP 5 min before IV [$^{11}$C]CPPC, whereas baseline animals received vehicle (n=3 per dose). Animals were sacrificed by cervical dislocation at 45 min following injection of 5.0 MBq (0.135 mCi) [$^{11}$C]CPPC [specific radioactivity=390 GBq/μmol (10.5 Ci/μmol)] in 0.2 mL saline into a lateral tail vein. The brains were removed, cortex was rapidly dissected on ice and blood samples (0.2-0.5 cc) were taken from heart. The cortex and blood samples were weighed and their radioactivity content was determined in a γ-counter LKB/Wallac 1283 CompuGamma CS (Bridgeport, CT). The outcome variables for the cortex are presented without blood correction as % SUV (FIG. 11A) and with blood correction as SUVR (FIG. 11B).

1.7.7.1 Brain Uptake of [$^{11}$C]CPPC in the Microglia-Depleted and Control Mice (FIG. 12A)

Male C57BL/6J mice (22-24 g) from Charles River Laboratories were purchased. Microglia-depleted mice were obtained by feeding the C57BL/6 mice (5 animals) for 3 weeks with pexidartinib (PLX3397)-formulated mouse chow (290 mg/kg) as described previously (Elmore M R, et al. (2014)). The control C57BL/6J mice (5 animals) were fed with standard mouse chow for 3 weeks. On the last day of treatment, all animals were sacrificed by cervical dislocation at 45 min following injection of 5.0 MBq (0.135 mCi) [$^{11}$C]CPPC [specific radioactivity=475 GBq/μmol (12.8 Ci/μmol)] in 0.2 mL saline into a lateral tail vein. The brains were removed, weighed and their radioactivity content was determined in a γ-counter LKB/Wallac 1283 CompuGamma CS (Bridgeport, CT). The outcome variables were calculated as % SUV.

1.7.7.2 Brain Uptake of [$^{11}$C]CPPC in the CSF1R Knock-Out and Control Mice (FIG. 12B). Methods B6.Cg-Csf1rtm1.2Jwp/J (CSF1R knock-out, KO) mice (21-23 g; age=four to eight weeks; Jackson Laboratories, Bar Harbor, ME) (5 animals) and age-matched C57BL/6J controls (23-27 g) (5 animals) were used. The animals were injected IV with 3.7 MBq (0.1 mCi) [$^{11}$C]CPPC [specific radioactivity=306 GBq/μmol (8.3 Ci/μmol)] and sacrificed by cervical dislocation at 45 min after the radiotracer injection. The whole brains were removed and blood samples (0.2-0.5 cc) were taken from heart. The whole brain and blood samples were weighed and their radioactivity content was determined in a γ-counter LKB/Wallac 1283 CompuGamma CS. The outcome variables were calculated as % SUV.

1.7.7.3 [$^{11}$C]CPPC Brain Uptake in the Control and LPS—Treated (Intracranial) Mice (FIG. 1)

Experiment 1, FIG. 1A. Nine male CD-1 mice (25-27 g, age=six to seven weeks) from Charles River Laboratories were divided in three cohorts: 1) sham-treated mice (n=3), baseline; 2) lipopolysaccharide (LPS-intracranial)—treated mice (n=3), baseline; and 3) lipopolysaccharide (LPS-intracranial)—treated mice (n=3), blocking. CD1 mice were anaesthetized with avertin (250 mg/kg, IP). Peri-procedural analgesia was provided with finadine (2.5 mg/kg, SC). The coordinates for intraparenchymal injection in the right forebrain were AP −0.5 mm' DV −2.5 mm; and ML 1.0 right of midline. The holes were drilled perpendicularly to the previously exposed skull. Sterile phosphate buffered saline (PBS) (0.5 μL) or 5 μg lipopolysaccharide (LPS, O11:B4, Calbiochem, San Diego, CA) in 0.5 μL PBS was injected into the brain parenchyma using a 1 μL Hamilton syringe. After injection, the needle was kept in the brain for additional 3 min and slowly removed. The incision was sealed with dental cement. The radiotracer study was performed on the 3rd day after LPS administration. The CPPC solution (0.3 mg/kg) was given IP, 5 min before IV [$^{11}$C]CPPC, whereas baseline animals received vehicle. The LPS and control animals were injected IV with 3.7 MBq (0.1 mCi) [$^{11}$C]CPPC [specific radioactivity=274 GBq/μmol (7.4 Ci/μmol)] and sacrificed by cervical dislocation at 45 min after the radiotracer injection. The whole brains were removed and dissected on ice. The cerebellum, ipsilateral brain hemisphere and contralateral brain hemisphere and blood samples were weighed and their radioactivity content was determined in a γ-counter LKB/Wallac 1283 CompuGamma CS. The outcome variables were calculated as % SUV.

Experiment 2, FIG. 1B. Sixteen male CD-1 mice (25-27 g, age=six to seven weeks) from Charles River Laboratories were divided in four cohorts: 1) sham-treated mice (n=4), baseline; 2) lipopolysaccharide (LPS-intracranial)—treated mice (n=4), baseline; 3) lipopolysaccharide (LPS-intracranial)—treated mice (n=4), blocking-0.6 mg/kg CPPC; 4) lipopolysaccharide (LPSintracranial)—treated mice (n=4), blocking-1.2 mg/kg CPPC. The mice were anaesthetized with avertin (250 mg/kg, IP). Peri-procedural analgesia was provided with finadine (2.5 mg/kg, SC). The coordinates for intraparenchymal injection in the right forebrain were AP −0.5 mm' DV −2.5 mm; and ML 1.0 right of midline. The holes were drilled perpendicularly to the previously exposed skull. Sterile phosphate buffered saline (PBS) (0.5 μL) or 5 μg lipopolysaccharide (LPS, O11:B4, Calbiochem, San Diego, CA) in 0.5 μL PBS was injected into the brain parenchyma using a 1 μL Hamilton syringe. After injection, the needle was kept in the brain for additional 3 min and slowly removed. The incision was sealed with dental cement. The radiotracer study was performed on the 3rd day after LPS administration. The CPPC solution (0.3 mg/kg) was given IP, 5 min before IV [$^{11}$C]CPPC, whereas baseline animals received vehicle. The LPS and control animals were injected IV with 3.7 MBq (0.1 mCi) [$^{11}$C]CPPC [specific radioactivity=366 GBq/μmol (9.9 Ci/μmol)] and sacrificed by cervical dislocation at 45 min after the radiotracer injection. The whole brains were removed and dissected on ice. The cerebellum, the ipsilateral brain hemisphere that was further cut into two quadrants, frontal and caudal, and contralateral brain hemisphere and blood samples were weighed and their radioactivity content was determined in a γ-counter LKB/Wallac 1283 CompuGamma CS. The outcome variables were calculated as % SUV.

1.7.7.4 [$^{11}$C]CPPC Brain Uptake in the Control and LPS—Treated (Intraperitoneal) Mice (FIG. 2)

Experiment 1, FIG. 2A. Fifteen male CD-1 mice (25-27 g, age=six to seven weeks) from Charles River Laboratories were divided in three cohorts: 1) control mice (n=5), baseline; 2) lipopolysaccharide (LPS)—IP treated (n=5) mice, baseline; and 3) lipopolysaccharide (LPS)—IP treated (n=5) mice, blocking with CPPC. The LPS (O111:B4, Calbiochem, San Diego, CA) solution in sterile saline (10 mg/kg, 0.2 mL) was administered intraperitoneally and the radiotracer study was performed on the 5th day after LPS administration. The CPPC solution (1 mg/kg) was given IP, 5 min before IV [$^{11}$C]CPPC, whereas baseline animals received vehicle. The LPS and control animals were injected IV with 3.7 MBq (0.1 mCi) [$^{11}$C]CPPC [specific radioactivity=444 GBq/μmol (12.0 Ci/μmol)] and sacrificed by cervical dislocation at 45 min after the radiotracer injection. The whole brains were removed and dissected on ice. The cerebellum and rest of brain were weighed and their radioactivity content was determined in a γ-counter LKB/Wallac 1283 CompuGamma CS. The outcome variables were calculated as % SUV.

Experiment 2, FIG. 2B. Fifteen male CD-1 mice (25-27 g, age=six to seven weeks) from Charles River Laboratories were divided in three cohorts: 1) control mice (n=5), baseline; 2) lipopolysaccharide (LPS)—IP treated (n=5) mice, baseline; and 3) lipopolysaccharide (LPS)—IP treated (n=5) mice, blocking with CPPC. The LPS (O111:B4, Calbiochem, San Diego, CA) solution in sterile saline (10 mg/kg, 0.2 mL) was administered intraperitoneally and the radiotracer study was performed on the 3rd day after LPS administration. The CPPC solution (1 mg/kg) was given IP, 5 min before IV [$^{11}$C]CPPC, whereas baseline animals received vehicle. The LPS and control animals were injected IV with 3.7 MBq (0.1 mCi) [$^{11}$C]CPPC [specific radioactivity=374 GBq/μmol (10.1 Ci/μmol)] and sacrificed by cervical dislocation at 45 min after the radiotracer injection. The whole brains were removed and dissected on ice and blood samples (0.2-0.5 cc) were taken from heart. The whole brain and blood samples were weighed and their radioactivity content was determined in a γ-counter LKB/Wallac 1283 CompuGamma CS. The outcome variables were calculated as SUVR.

Experiment 3, FIG. 2C. Fifteen male CD-1 mice (25-27 g, age=six to seven weeks) from Charles River Laboratories were divided in three cohorts: 1) control mice (n=3), baseline; 2) lipopolysaccharide (LPS)—IP treated (n=6) mice, baseline; and 3) lipopolysaccharide (LPS)—IP treated (n=6) mice, blocking with compound 8. The LPS (O111:B4, Calbiochem, San Diego, CA) solution in sterile saline (10 mg/kg, 0.2 mL) was administered intraperitoneally and the radiotracer study was performed on the 3rd day after LPS administration. The compound 8 solution (2 mg/kg) was given IP, 5 min before IV [$^{11}$C]CPPC, whereas baseline animals received vehicle. The LPS and control animals were injected IV with 3.0 MBq (0.08 mCi) [$^{11}C$]CPPC [specific radioactivity=148 GBq/μmol (4.0 Ci/μmol)] and sacrificed by cervical dislocation at 45 min after the radiotracer injection. The whole brains were removed and dissected on ice and blood samples (0.2-0.5 cc) were taken from heart. The whole brain and blood samples were weighed and their radioactivity content was determined in a γ-counter LKB/Wallac 1283 CompuGamma CS. The outcome variables were calculated as SUVR to blood.

1.7.7.5 [$^{11}C$]CPPC Brain Uptake in the Alzheimer's Mouse Model and Control Mice (FIG. 3)

Mouse model of Alzheimer's disease-related amyloidosis overexpressed Amyloid Precursor Protein (APP) with Swedish and Indiana mutations was used. The transgenic APP had tetracycline transactivator (tTa)—sensitive promoter that was activated by over-expressing tTa driven by CaMKII promoter (5). Due to such combination of transgenes, the overexpression of transgenic APP was observed only in principal neurons of the forebrain. Mice that did not express any of the transgenes served as controls. The Alzheimer's male mice (AD) and their sex-matched control littermates were 16 months of age at the time of the study. At this age, the AD mice have significant Aβ amyloid plaque deposition in the forebrain including the cortex and hippocampus (Melnikova T, et al. (2013). Six AD mice and six age-matched controls were used for this study. The animals were injected IV with 5.6 MBq (0.15 mCi) [$^{11}C$]CPPC [specific radioactivity=340 GBq/μmol (9.2 Ci/μmol)] and sacrificed by cervical dislocation at 45 min after the radiotracer injection. The whole brains were removed and rapidly dissected on ice. The cerebellum and rest of brain were weighed and their radioactivity content was determined in a γ-counter LKB/Wallac 1283 CompuGamma CS. The outcome variables were calculated as % SUV.

1.7.8 [$^{11}C$]CPPC Full Body Radiation Dosimetry in Mice Methods

Radiation dosimetry for [$^{11}C$]CPPC was studied in fifteen male CD-1 mice (23-27 g) following our published procedure (Stabin M G, et al. (2005)). A solution of [$^{11}C$]CPPC in 0.2 ml of saline (7.4 MBq or 0.2 mCi) was injected as a bolus into the lateral tail vein, and groups of mice (n=3) were euthanized at 10, 30, 45, 60, and 90 min after the radiotracer injection. The lungs, heart, kidneys, liver, spleen, intestine, stomach, and brain were quickly removed and put on ice. One femur and samples of thigh muscle, bone marrow and blood were also collected. The organs were weighed, and the tissue radioactivity was measured with an automated gamma counter (LKB Wallac 1282 CompuGamma CS Universal Gamma Counter). The percent injected dose per organ (% ID/organ) was calculated by comparison with samples of a standard dilution of the initial dose. All measurements were corrected for decay. Resultant values of % ID/organ were fit using the SAAM II software (Foster D M (1998)). Time integrals of activity (Stabin M G and Siegel J A (2003)) were entered into the OLINDA/EXM software (Stabin M G, et al. (2005)), using the adult male model. Activity was observed in the intestines (~35%). The number of disintegrations in the remainder of body was assumed to be equal to 100% of the activity administered integrated to total decay of $^{11}C$, minus the disintegrations in other body organs.

1.7.8.1 Results

The fitted metabolic model, number of disintegrations in the source organs, and organ doses are summarized below:

The fitted metabolic model was as follows:

| Organ | % | T-bio (hr) | % | T-bio (hr) |
|---|---|---|---|---|
| Brain | 3.83 | 0.302 | 0.38 | ∞ |
| Heart | 1.00 | 0.272 | 0.14 | ∞ |
| Lungs | 8.27 | 0.159 | 1.53 | 2.27 |
| Liver | 97.6 | 0.764 | −100 | 0.335 |
| Kidneys | 8.32 | 0.297 | 1.52 | ∞ |
| Spleen | 1.43 | 0.823 | −1.24 | 0.145 |

The numbers of disintegrations in the source organs (in MBq-hr/MBq administered) were:

| | |
|---|---|
| Brain | 1.10E−02 |
| LLI | 7.00E−04 |
| Small Intestine | 1.53E−01 |
| ULI | 1.81E−02 |
| Heart Wall | 2.80E−03 |
| Kidneys | 2.65E−02 |
| Liver | 8.80E−02 |
| Lungs | 2.00E−02 |
| Spleen | 3.00E−03 |
| Remainder | 1.68E−01 |

TABLE 3

Estimated Human Doses

| Target Organ | mSv/MBg | rem/mCi |
|---|---|---|
| Adrenals | 3.11E−03 | 1.15E−02 |
| Brain | 2.70E−03 | 9.99E−03 |
| Breasts | 1.29E−03 | 4.76E−03 |
| Gallbladder Wall | 5.35E−03 | 1.98E−02 |
| LLI Wall | 4.29E−03 | 1.59E−02 |
| Small Intestine | 4.73E−02 | 1.75E−01 |
| Stomach Wall | 2.76E−03 | 1.02E−02 |
| ULI Wall | 1.73E−02 | 6.42E−02 |
| Heart Wall | 3.72E−03 | 1.38E−02 |
| Kidneys | 2.56E−02 | 9.48E−02 |
| Liver | 1.60E−02 | 5.90E−02 |
| Lungs | 6.10E−03 | 2.26E−02 |
| Muscle | 1.84E−03 | 6.79E−03 |
| Ovaries | 5.21E−03 | 1.93E−02 |
| Pancreas | 3.18E−03 | 1.18E−02 |
| Red Marrow | 2.19E−03 | 8.09E−03 |
| Osteogenic Cells | 2.13E−03 | 7.87E−03 |
| Skin | 1.19E−03 | 4.41E−03 |
| Spleen | 6.08E−03 | 2.25E−02 |
| Testes | 1.20E−03 | 4.42E−03 |
| Thymus | 1.44E−03 | 5.33E−03 |
| Thyroid | 1.18E−03 | 4.38E−03 |
| Urinary Bladder Wall | 2.14E−03 | 7.92E−03 |
| Uterus | 4.57E−03 | 1.69E−02 |
| Total Body | 2.90E−03 | 1.07E−02 |
| Effective Dose | 4.80E−03 | 1.78E−02 |

1.7.8.2 Summary of Radiation Dosimetry Study

The data were all well fit with two exponential functions. Most organs appear to receive around 0.002-0.006 mSv/MBq (0.007 to 0.011 rem/mCi). The small intestine appears to receive the highest dose, around 0.047 mSv/MBq (0.17 rem/mCi). The effective dose is about 0.0048 mSv/MBq (0.018 rem/mCi).

1.7.9 PET CT Imaging in Mice with Experimental Autoimmune Encephalitis (FIG. 4, FIG. 13)

Adult female C57BL/6J mice, age=13 weeks (Jackson Laboratories, Bar Harbor M E) were inoculated with MOG35-55 peptide and behaviorally scored as described previously (Jones M V, et al. (2008)): Briefly, incomplete Freund's adjuvant (Pierce) containing 8 mg/ml of heat-killed *Mycobacterium tuberculosis* H37 RA (Difco) was mixed at 1:1 with a 2 mg/ml solution of MOG35-55 (Johns Hopkins Biosynthesis & Sequencing Facility): $NH_2$-MEVGWYR-SPFSRVVHLYRNGK-COOH diluted in phosphate-buffered saline (PBS). After forming a stable emulsion, a total of 100 μl of the resulting mixture was divided between two subcutaneous injection sites at the base of the tail (i.e. 400 μg of *M. tuberculosis* and 100 μg of MOG35-55 per mouse). On the day of immunization (day 0 post-immunization: day 0 p.i.) and 2 days later, 250 ng of pertussis toxin (EMD/Calbiochem, USA) diluted in PBS was injected intravenously. Symptomatic MOG-inoculated mice and an uninoculated, healthy mouse were scanned 14 days after the first inoculation. Scoring is determined according to (Beeton C, et al. (2007)). Briefly, mice are scored from 0-5, where a score of 0 represents no clinically observed features and a score of 5 represents complete hind limb paralysis with incontinence. A score of 3 represents moderate paraparesis with occasional tripping. Scores of 0.5 (distal limp tail), 2.5 (mild/moderate paraparesis with tripping) and 4.5 (complete hind limb paralysis) were assayed in this study. Each mouse was injected IV with 8.14 MBq [220 μCi, SA>370 GBq/μmol (>10 Ci/μmol)] proceeded using a Sedecal SuperArgus PET/CT scanner (Madrid, Spain). CT scans for anatomic co-registration were performed over 512 slices at 60 kVp. PET and CT data were reconstructed using the manufacturer's software and displayed using AMIDE software (http://amide.sourceforge.net/). To preserve dynamic range, harderian and salivary gland PET signal was partially masked using a thresholding method (FIG. 4), whereas unmasked images are shown in FIG. 13. Regions of interest were drawn over PET visible lesions through three slices and quantitated in the regions indicated.

1.7.10 Mouse Plasma and Brain Radiometabolite Analysis

Six male CD-1 mice (25-27 g, age=six to seven weeks) from Charles River Laboratories were used. The animals were injected IV with 37 MBq (1 mCi) [$^{11}$C]CPPC [specific radioactivity=673 GBq/μmol (18.2 Ci/μmol)] and sacrificed by cervical dislocation at 10 min (3 animals) and 30 min (3 animals) after the radiotracer injection. The whole brains were removed and dissected on ice and blood samples (0.5 cc) were taken from heart. Radiometabolites of [$^{11}$C]CPPC in the mouse plasma and brain were analyzed using a general HPLC method described above for baboon. Before the HPLC analysis the mouse brain was homogenized in 2 mL of mixture 50% acetonitrile: 50% phosphate buffer (Et3N, H3PO4, pH 7.2). The homogenates were centrifuged (14000 g for 5 min) and supernatants filtered using 0.2 micron filter and filtrate was analyzed by radio-HPLC with phenomenex Gemini C18, 10μ, 4.6×250 mm and 2 mL/min isocratic elution and 50% acetonitrile-50% aqueous triethylamine, c=0.06 M and pH=7.2 as mobile phase. The study demonstrated that in mouse plasma the radiotracer [$^{11}$C]CPPC forms the same two radiometabolites as those in baboon plasma (FIG. 17). The radiometabolites poorly penetrate the blood-brain barrier and their presence in the brain is low (Table 4)

TABLE 4

Parent [$^{11}$C]CPPC and its radiometabolites in mouse plasma and brain.

| | Plasma | | Brain | |
|---|---|---|---|---|
| Time-point | Metabolites, % | Parent [$^{11}$C]CPPC, % | Metabolites, % | Parent [$^{11}$C]CPPC, % |
| 10 min | 29.9 ± 2.3 | 70.2 ± 2.2 | 3.4 ± 0.1 | 96.6 ± 0.1 |
| 30 min | 60.3 ± 1.4 | 39.7 ± 1.3 | 4.9 ± 1.7 | 85.1 ± 1.6 |

1.7.11 Quantitative Real Time PCR (qRT-PCR) and Western Blot Analyses of Whole Brain of Control and LPS-Treated CD1 Mice.

Six male CD-1 mice (25-27 g, Charles River) were intraperitoneally injected with LPS (O111:B4, Calbiochem, San Diego, CA, 10 mg/kg, 0.2 mL). Mice were euthanized on day 4 postLPS injection and whole brains were collected. Half of the brains were snap frozen in liquid nitrogen and stored at −80 °C for western blot analyses. The other half of brains were immediately stored in 1 mL of the RNAlater® (Millipore Sigma, St. Luis, MO) at 4 °C. After 24 hr, RNAlater® solution was removed from the samples and the brain was frozen at −80 °C for total RNA isolation.

Western Blot: For western blot, the brain samples were homogenized with T-PER Tissue Protein Extraction Reagent (Thermo Fisher Scientific, Halethorpe, MD) for 30 seconds total of 6 times and centrifuged at 12000 rpm for 5 min. Supernatant were collected and 10 μg of proteins were separated by SDS-PAGE and transferred onto the NC membrane. The following antibodies were used for Western blot analysis: α-mCSF1R Ab (Cell Signaling Technology, Danver, MA), αmGAPDH Ab (Santa Cruz Biotechnology, Inc., Dallas, TX). The blots were visualized by Clarity Western ECL Substrate (Bio-Rad, Hercules, CA) and Gel Doc™ XR+ System (Bio-Rad). The band intensity was measured and calculated by Image Lab™ Software (Bio-Rad).

qRT-PCR: For qRT-PCR, total RNA was isolated from the brain using Quick-RNA™ Miniprep Kit, (Zymo Research, Irvine, CA) and cDNA were synthesized from the isolated RNA using High-capacity cDNA reverse transcription kit (Thermo Fisher Scientific). qPCR reactions were performed using the following Tagman™ assays: Csf1r: Mm01266652_m1, Pgk1: Mm00435617_m1, Gapdh: Mm99999915_g1). Relative quantity was calculated using Pgk1 and Gapdh as internal controls.

1.7.12 Baboon Radiometabolite Analysis

Baboon PET studies are demonstrated in FIG. 15 and FIG. 16.

The relative percentage of [$^{11}$C]CPPC in plasma was determined by high performance liquid chromatography (HLPC) in blood samples drawn at 5, 10, 20, 30, 60, and 90 min after radiotracer injection. The modified column-switching HPLC method was used (Coughlin, NeuroImage 165, 2018, page 120). The HPLC system containing of a 1260 infinity quaternary pump, a 1260 infinity column compartment module, a 1260 infinity UV and a Raytest GABI Star radiation detectors was operated with OpenLab CDS EZChrom (A.01.04) software. 0.4-1.5 mL of plasma samples loaded into a 2 mL Rheodyne injector loop were initially directed to the capture column (packed with Phenomenex Strata-X 33 μm polymeric reversed phase sorbent) and both detectors with 1% acetonitrile and 99% water mobile phase at 2 mL/min. After 1 min of isocratic elution, analytical mobile phase composed of 65% acetonitrile and 35% aqueous solution triethylamine, c=0.06M and pH=7.2

(adjusted with phosphoric acid) was applied to direct trapped on the capture column non-polar compounds to an analytical column (Gemini C18(2) 10 μm 4.62×50 mm) and detectors at 2 mL/min. The HPLC system was standardized using nonradioactive CPPC and [$^{11}$C]CPPC prior to analysis of blood plasma samples, which were spiked with 5 μL of CPPC at concentration of 1 mg/mL. The total plasma time-activity curves were obtained by analyzing of 0.3 mL of blood plasma samples on a PerkinElmer Wizard 2480 automatic gamma counter. Plasma free fraction (fp) of [$^{11}$C]CPPC was determined using centrifree ultrafiltration devices.

Radiometabolite analysis was carried out using a column-switching HPLC method, which allows to inject blood plasma directly into HPLC system without time consuming prior protein precipitation and extraction. Initially sample is directed into capture column for solid phase extraction of parent tracer and its non-polar radiometabolites. Most of blood plasma constituents and polar radiometabolites of parent radiotracer do not retain on a capture column and are eluted into detectors. Then analytical mobile is applied to elute trapped compounds on the capture column into analytical column, where they are separated and further directed into detectors. This way all radioactive compounds present in the sample can be detected allowing for precise quantification of relative percentage of parent tracer versus its radiometabolites. As presented in the FIG. 17A, 100% of injected [$^{11}$C]CPPC could be effectively trapped on a capture column used and with analytical mobile phase it elutes at 7.35 min. Representative HPLC chromatogram of plasma samples obtained at different time intervals are presented in FIG. 17A and time dependent blood plasma relative percentage of [$^{11}$C]CPPC in non-treated control and LPS or LPS+blocking agent treated baboons is presented in the FIG. 17B. Administration of LPS or LPS and blocking agent did not affect metabolic pattern and rate of [$^{11}$C]CPPC. Two peaks at 0.97 min and 4.82 min of elution related to less lipophilic radiometabolite of parent tracer were detected. The relative percentage of [$^{11}$C]CPPC was 84.87±2.01, 75.57±1.76, 62.5±4.47, 51.73±6.14, 34.8±1.31 and 25.6±2.77 at 5, 10, 20, 30, 60, and 90 min post radiotracer injection.

Plasma free fraction of [$^{11}$C]CPPC determined using centrifree ultrafiltration devices was also not affected by LPS or LPS and blocking treatment and it was 5.48±0.98%.

1.7.13 Baboon PET Imaging Methods

PET images were acquired using a CPS/CTI High Resolution Research Tomograph (HRRT), which has an axial resolution (FWHM) of 2.4 mm, and in plane resolution of 2.4-2.8 mm. The animal was anesthetized and handled as described previously (*Horti* A G, et al. (2016)). The 90 min PET data were binned into 30 frames: four 15-sec, four 30-sec, three 1-min, two 2-min, five 4-min, and twelve 5-min frames. Images were reconstructed using the iterative ordered subset expectation maximization (OS-EM) algorithm (with six iterations and 16 subsets) with correction for radioactive decay, deadtime, attenuation, scatter and randoms (Rahmim A, et al. (2005)). The reconstructed image space consisted of cubic voxels, each 1.22 $mm^3$ in size, and spanning dimensions of 31 cm×31 cm (transaxially) and 25 cm (axially).

Blood samples were obtained via the arterial catheter at continually prolonged intervals throughout the 90 min scan (as rapidly as possible for the first 90 seconds, with samples acquired at increasingly longer intervals thereafter). Samples were centrifuged at 1,200×g and the radioactivity in plasma were measured with a cross-calibrated gamma counter. Selected plasma samples (5, 10, 20, 30, 60, and 90 min) were analyzed with high performance liquid chromatography (HPLC) for radioactive metabolites in plasma as described above.

1.7.14 Baboon PET Data Analysis

The image analysis and kinetic modeling were performed using software PMOD (v3.7, PMOD Technologies Ltd, Zurich, Switzerland). Dynamic PET images were first co-registered with the MRI images. A locally developed volume-of-interest (VOI) template, including 13 representative baboon brain structures, was then transferred to the animal's MRI image. The VOIs included frontal and temporal gyrus, thalamus, hippocampus, caudate, putamen, amygdala, globus pallidus, insula, hypothalamus, cerebellum, corpus callosum, and white matter. Time activity curve (TAC) of each VOI was obtained by applying the VOI on PET frames.

Next, based on the TACs and the metabolite-corrected arterial plasma input functions, kinetic modeling was performed to quantitatively characterize the [$^{11}$C]CMPFF binding in brain. For brain uptake, the primary outcome measure is the regional brain distribution volume ($V_T$) of [$^{11}$C]CPPC, defined as concentration of the radiotracer in regional tissue relative to that in blood at equilibrium. Regional $V_T$ is proportional to the receptor density in the defined VOL. Because it is not anticipated that any brain region to be devoid of specific [$^{11}$C]CPPC uptake, another commonly used outcome measure, namely, the non-displaceable binding potential (BPND), may not be obtained reliably. For each VOI, $V_T$ was calculated using both compartmental modeling and the Logan graphical method. Logan J, et al. (1990). Time-consistency analysis was also performed. Representative results are presented in FIG. 18.

Figure 18:
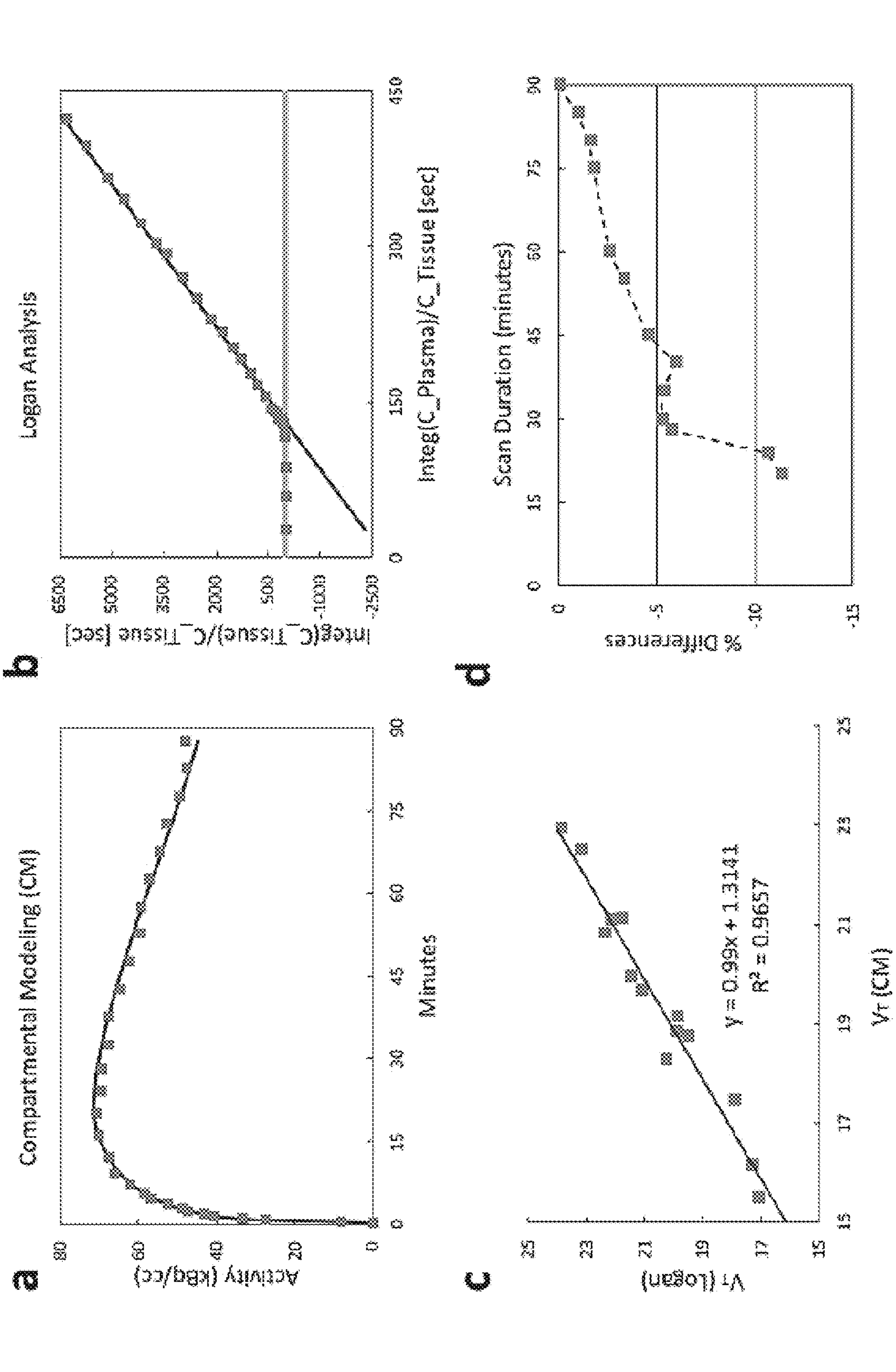

In summary, both compartmental modeling and Logan method are suitable for analyzing the [$^{11}$C]CPPC PET data (example shown in FIG. 18-*a* and *b*), and they generated very comparable regional $V_T$ results (FIG. 18-*c*). All brain regions yielded stable $V_T$ estimates for scan durations longer than 60 minutes (FIG. 18-*d*). To facilitate obtaining $V_T$ parametric images (FIG. 5 and FIG. 13), the Logan method was selected for presenting all $V_T$ values herein.

Example 2

Synthesis of Arylamides

In general, the synthesis route started with the SNAr reaction of 2-fluoro-4-chloronitrobenzene 2 with piperidine or 4-methylpiperidine in ethanol to give the N-alkylated compounds 4a-b in very high yield. The N-methyl piperazine reacts with 4a-b in neat reaction at 140 °C to afford the compounds 5a-b. On other hand, the N-Boc piperazine reacts with 4a-b in the presence of inorganic base $K_2CO_3$ with DMSO as solvent to produce the compounds 5c-5d. The reduction of the nitro group to the aniline followed by standard amide bond formation with 5-cyanofuran-2-carboxylic acid or 4-cyano-1H-pyrrole-2-carboxylic acid afforded the desired products 1a, 1c, 1e and 7a-c. For the radiosynthesis, the precursor 1b, 1d and if obtained from 7a-c with N-Boc deprotection using TFA in methylene chloride.

The synthesis also included a Suzuki-Miyaura coupling, see Miyaura and Suzuki, 1995, between the anilinoboronic ester 8 (which is distinguished from "compound 8" referred to hereinabove) and the enol triflate ester derivative of N-Boc-protected piperidinone 9. See Wustrow and Wise, 1991. After hydrogenation of the olefin 10, the resulting aniline 11 was brominated with N-bromosuccinimide (NBS)

to give 12. After that Suzuki-Miyaura coupling with 1-cyclohexeneboronic acid and compound 12 afforded the amine compound 13. The potassium salt of the trimethylsilylethoxymethyl (SEM)-protected imidazole-2-carboxylate was prepared according to the reported procedure. See Wall et al., 2008. The compound 13 is coupled to 14 using HATU and N,N-diisopropylethylamine (DIPEA) in DMF to provide amide 15 in good yield. Simultaneous removal of both the Boc and the SEM groups with trifluoroacetic acid (TFA) afforded an intermediate 16 that was used for the preparation of 1g and 17. Boc removal provided the precursor compound 1h.

Synthesis of Arylamides 7a-d and 8a-b.

Reagents and conditions: (a) Ethanol, 0 °C to rt, 0.5h, 96%; (b) 140 °C, 12 h for 5a-b, $K_2CO_3$, DMSO, 110 °C, 12 h for 5c-d, 80% to 95%; (c) Zn, $NH_4Cl$, THF/MeOH/$H_2O$, reflux, 1h, 90%; (d) HATU, DIPEA, DMF, rt, 5-cyanofuran-2-carboxylic acid for 1a, 1c, 7a-b and 4-cyano-1H-pyrrole-2-carboxylic acid for 1e, 7c, 12 h, 75-82%; (e) TFA, MC, rt, 12 h, 90%.

The synthesis of arylamides 1a-1 is provided below:

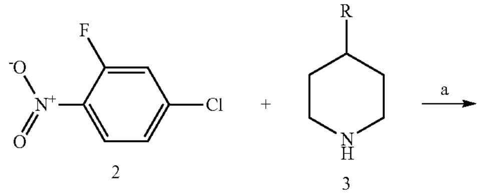

2

3

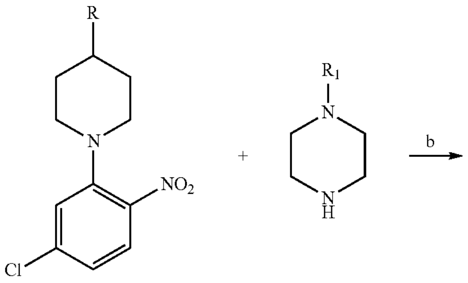

4a-b

4a: R = H

4b: R = $CH_3$

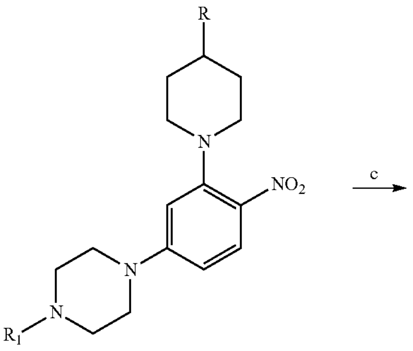

5a-d

5a: R = H, $R_1 = CH_3$

5b: R = $CH_3$, $R_1 = CH_3$

5c: R = H, R1 = COOC(CH3)$_3$

5d: R = $CH_3$, R1 = COOC(CH3)$_3$

-continued

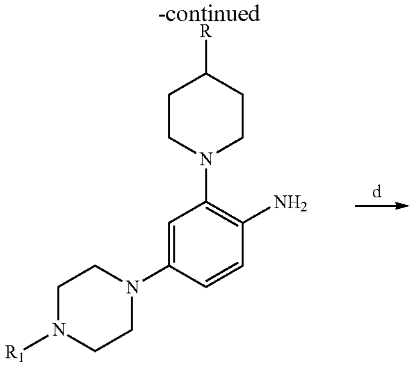

6a-d

6a: R = H, $R_1 = CH_3$

6b: R = $CH_3$, $R_1 = CH_3$

6c: R = H, R1 = COOC(CH3)$_3$

6d: R = $CH_3$, R1 = COOC(CH3)$_3$

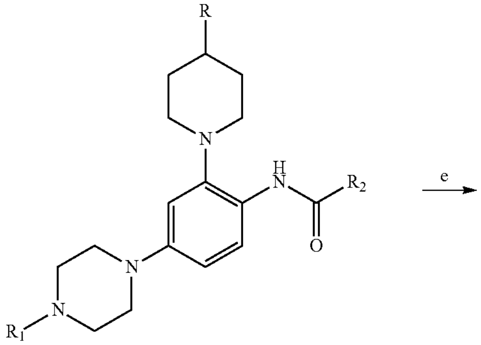

1a, 1c, 1e, 1g-i and 7a-c

1a: R = H, $R_1 = CH_3$, $R_2$ = 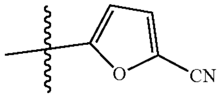

1c: R = $CH_3$, $R_1 = CH_3$, $R_2$ = 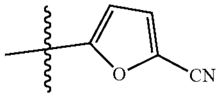

1e: R = $CH_3$, $R_1 = CH_3$, $R_2$ = 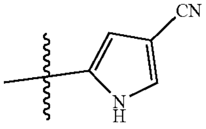

1g: R = H, $R_1 = CH_3$, $R_2$ = 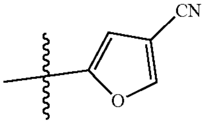

1h: R = H, $R_1 = CH_3$, $R_2$ = 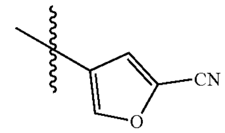

1i: R = H, $R_1 = CH_3$, $R_2$ = 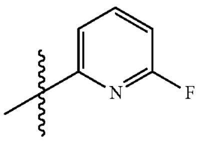

1j: R = H, $R_1 = CH_3$, $R_2$ = 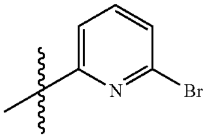

-continued

7a: R = H, $R_1$ = COOC(CH3)$_3$, $R_2$ =

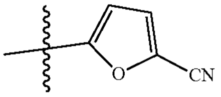

7b: R = $CH_3$, $R_1$ = COOC(CH3)$_3$, $R_2$ =

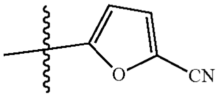

7c: R = $CH_3$, $R_1$ = COOC(CH3)$_3$, $R_2$ =

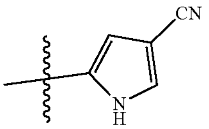

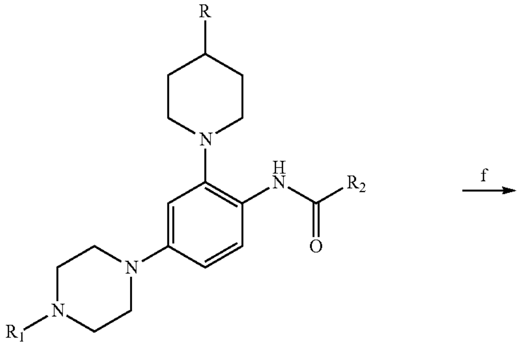

1b, 1d, and 1f

1b: R = H, $R_1$ = H, $R_2$ =

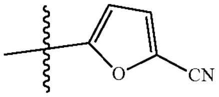

1d: R = $CH_3$, $R_1$ = H, $R_2$ =

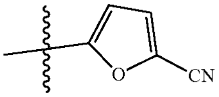

1f: R = $CH_3$, $R_1$ = H, $R_2$ =

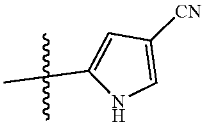

-continued

1m: R = H, $R_1$ = H, $R_2$ =

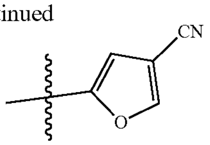

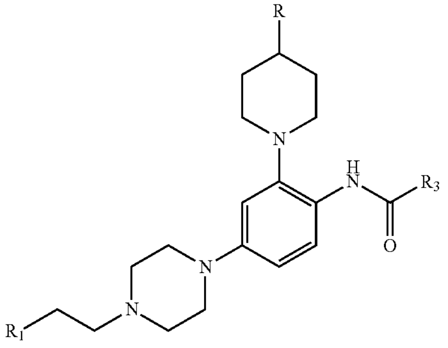

1k-m

1k: R = H, $R_1$ = $CH_2CH_2F$, $R_3$ =

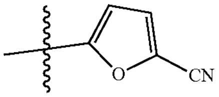

1l: R = $CH_3$, $R_1$ = $CH_2CH_2F$, $R_3$ =

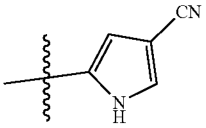

1m: R = H, $R_1$ = $CH_2CH_2Br$, $R_3$ =

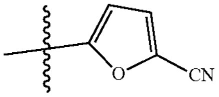

Reagents and conditions: (a) Ethanol, 0 °C to rt, 0.5h, 96%; (b) 140 °C, 12 h for 5a-b, $K_2C_{03}$, DMSO, 110 °C, 12 h for 5c-d, 80% to 95%; (c) Zn, $NH_4Cl$, THF/MeOH/$H_2O$, reflux, 1 h, 90%; (d) Carboxylic acid, HATU, DIPEA, DMF, 12 h, 75-82%; (e) TFA, MC, rt, 12 h, 90%; f) Fluoroethyl tosylate, Et3N, ACN, 90 °C, 12 h, 60-70% for 1k-1 and 1,2-dibromoethane, Et3N, ACN, 90 °C, 12h, for 1 m, 65%.

The synthesis of aryl amides 1g and 1 h is provided below:

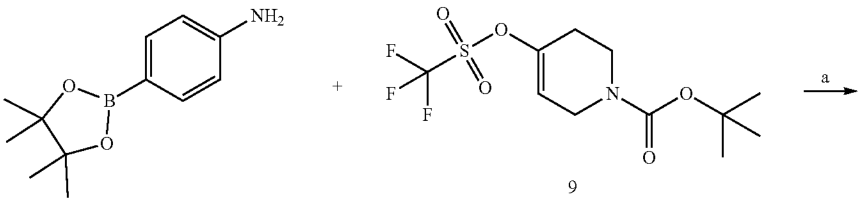

8

9

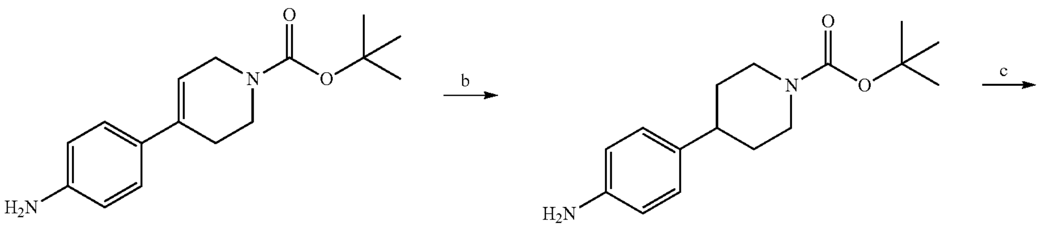

10

11

-continued
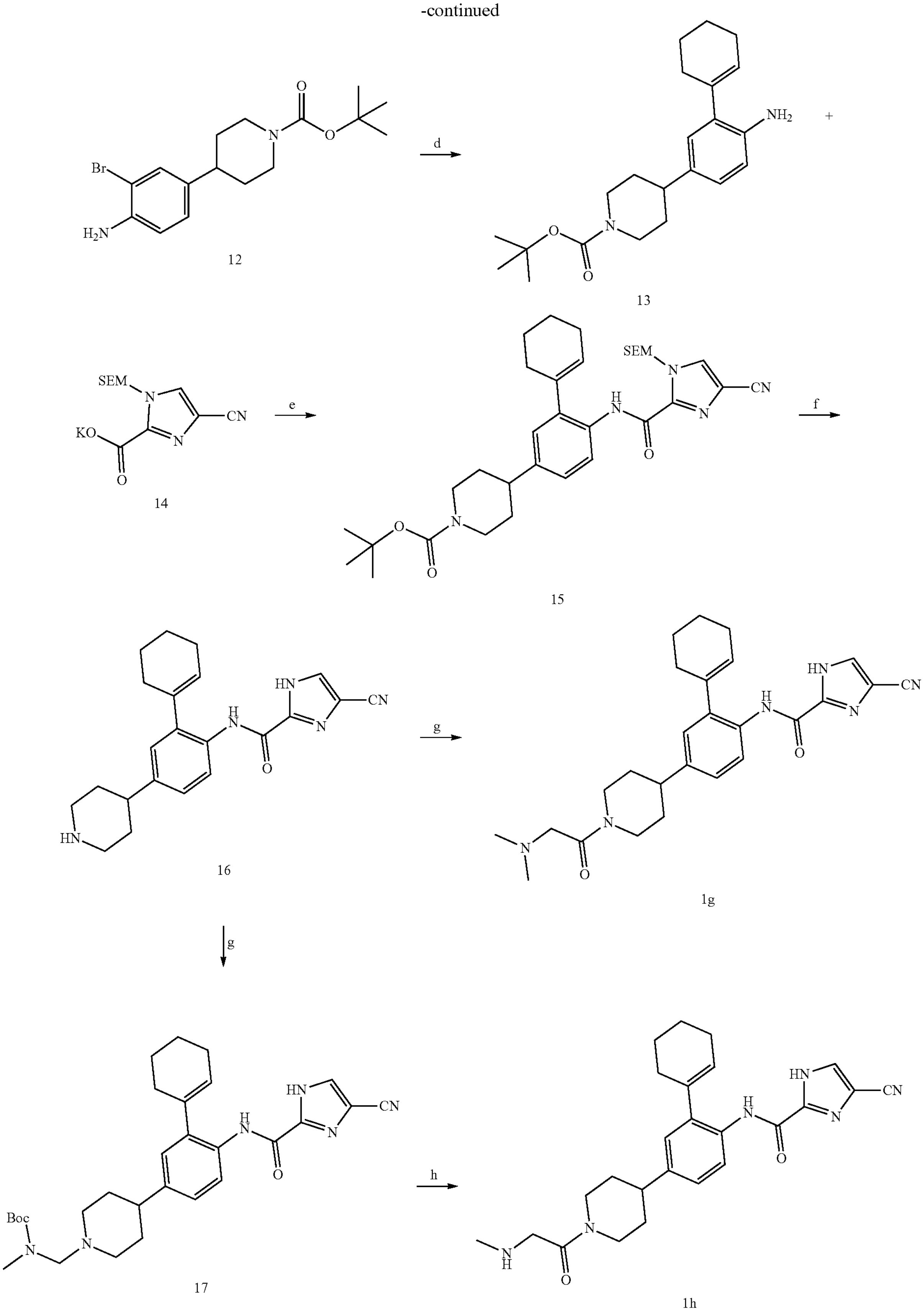
12 13 14 15 16 1g 17 1h

Reagents and conditions: (a) $Pd(PPh_3)_4$, LiCl, 2 M $Na_2CO_3$, dioxane, 1000 °C, 2 h. (b) H2, 10% Pd/C, MeOH, 20 psi, 1 h. (c) NBS, $CH_2Cl_2$, room temperature, 10 h. (d) Pd(dppf) $Cl_2$·DCM, 2 M $Na_2CO_3$, 1,4-Dioxane, 100 °C, 15 h. (e) HATU, DIPEA, DMF, 10 h. (f) TFA, $CH_2Cl_2$, room temperature, 20 h, g) HATU, DIPEA, DMF, dimethylglycine for 1g and N-(tert-butoxy carbonyl)-N-methylglycine for 17, 12h, h) TFA, $CH_2Cl_2$, room temperature, 20 h.

1-(5-Chloro-2-nitrophenyl)piperidine (4a): To a cooled (0 °C) solution of 1.0 g (10.0 mmol) of 4-chloro-2-fluoronitrobenzene in 15 mL of EtOH was added 1.7 mL (30.0 mmol) of piperidine dropwise over 5 min. The solution stirred at 0 °C for 10 min and then at 23 °C for 30 min. The mixture was poured into water (225 mL) and extracted with EtOAc (2×30 mL). The combined extracts were washed with saturated aq $NaHCO_3$ and brine (30 mL each) and then dried over $Na_2SO_4$ and evaporated to get the crude compound. The resulting residue was purified by silica gel column chromatography (Hexane:EtOAc=9.5:0.5) to give 1-(5-chloro-2-nitrophenyl)piperidine as a yellow solid (1.32 g, 96% N yield). H NMR (500 MHz, $CDCl_3$) δ7.77 (d, J=5.0 Hz, 1H), 7.13 (s, 1H), 6.93 (d, J=10.0 Hz, 1H), 3.30-3.27 (m, 2H), 2.91-2.86 (m, 2H), 1.90-1.86 (m, 1H), 1.75-1.73 (m, 2H), 1.49-1.42 (m, 1H).

1-(5-Chloro-2-nitrophenyl)-4-methylpiperidine (4b): To a cooled (0 °C) solution of 1.0 g (10.0 mmol) of 4-chloro-2-fluoronitrobenzene in 15 mL of EtOH was added 1.01 mL (30.0 mmol) of 4-methylpiperidine dropwise over 5 min. The solution stirred at 0 °C for 10 min and then at 23 °C for 30 min. The mixture was poured into water (225 mL) and extracted with EtOAc (2×30 mL). The combined extracts were washed with saturated aq $NaHCO_3$ and brine (30 mL each) and then dried over $Na_2SO_4$ and evaporated to get the crude compound. The resulting residue was purified by silica gel column chromatography (Hexane:EtOAc=9.5:0.5) to give 1-(5-chloro-2-nitrophenyl)-4-methylpiperidine as a yellow solid (1.4 g, 96% yield). $^1$H NMR (500 MHz, $CDCl_3$) δ7.77 (d, J=5.0 Hz, 1H), 7.13 (s, 1H), 6.93 (d, J=10.0 Hz, 1H), 3.30-3.27 (m, 2H), 2.91-2.86 (m, 2H), 1.90-1.86 (m, 1H), 1.75-1.73 (m, 2H), 1.49-1.42 (m, 1H), 1.02 (d, J=5.0 Hz, 3H).

1-Methyl-4-(4-nitro-3-(piperidin-1-yl)phenyl)piperazine (5a): A mixture of 1-(5-chloro-2-nitrophenyl)piperidine (1.0 g, 4.15 mmol) and 1-methylpiperazine (1.38 mL, 12.46 mmol) were heated with stirring under $N_2$ at 138 °C for 12 h. After cooling to rt, the mixture was poured into water and extracted with ethyl acetate (2×100 mL). The combined extracts were washed with water and brine and then dried over $Na_2SO_4$ and evaporated to get the crude compound. The resulting residue was purified by silica gel column chromatography ($CH_2Cl_2$:MeOH=9:1) to give 1-methyl-4-(4-nitro-3-(piperidin-1-yl)phenyl)piperazine as a yellow solid (1.2 g, 96% yield). $^1$H NMR (500 MHz, $CDCl_3$) δ7.62 (d, J=5.0 Hz, 1H), 6.80 (s, 1H), 6.43 (d, J=10.0 Hz, 1H), 3.84 (t, J=5.0 Hz, 4H), 3.71 (t, J=5.0 Hz, 2H), 3.60 (t, J=5.0 Hz, 4H), 3.50 (d, J=10.0 Hz, 2H), 3.80 (d, J=5.0 Hz, 2H), 1.55-1.51 (m, 3H).

1-Methyl-4-(3-(4-methylpiperidin-1-yl)-4-nitrophenyl) piperazine (5b): A mixture of 1-(5-chloro-2-nitrophenyl)-4-methylpiperidine (1.0 g, 3.92 mmol) and 1-methylpiperazine (1.30 mL, 11.77 mmol) were heated with stirring under $N_2$ at 138 °C for 12 h. After cooling to rt, the mixture was poured into water and extracted with ethyl acetate (2×100 mL). The combined extracts were washed with water and brine and then dried over $Na_2SO_4$ and evaporated to get the crude compound. The resulting residue was purified by silica gel column chromatography ($CH_2Cl_2$:MeOH=9:1) to give 1-methyl-4-(3-(4-methylpiperidin-1-yl)-4-nitrophenyl)piperazine as a yellow solid (1.2 g, 96% yield). $^1$H NMR (500 MHz, $CDCl_3$) δ7.62 (d, J=5.0 Hz, 1H), 6.80 (s, 1H), 6.43 (d, J=10.0 Hz, 1H), 3.84 (t, J=5.0 Hz, 4H), 3.71 (t, J=5.0 Hz, 2H), 3.60 (t, J=5.0 Hz, 4H), 3.50 (d, J=10.0 Hz, 2H), 1.80 (d, J=5.0 Hz, 2H), 1.55-1.51 (m, 3H), 1.03 (d, J=5.0 Hz, 3H).

Tert-butyl 4-(4-nitro-3-(piperidin-1-yl)phenyl)piperazine-1-carboxylate (5c): To the mixture of 1-(5-chloro-2-nitrophenyl)piperidine (1.0 g, 4.15 mmol) and tert-butyl piperazine-1-carboxylate (1.55 g, 8.30 mmol), in DMSO (10 mL) was added $K_2CO_3$ (1.72 g, 12.45 mmol). The reaction mixture was stirred at 110 °C for 12 h and then partitioned between EtOAc and brine. The organic layer was separated, dried over anhydrous $MgSO_4$, filtered, and concentrated under a vacuum. The resulting residue was purified by silica gel column chromatography (Hexane:EtOAc=3:7) to give tert-butyl 4-(4-nitro-3-(piperidin-1-yl)phenyl)piperazine-1-carboxylate as a white solid (1.40 g, 86.4% yield). $^1$H NMR (500 MHz, $CDCl_3$) δ7.99 (d, J=10.0 Hz, 1H), 6.38 (d, J=10.0 Hz, 1H), 6.31 (s, 1H), 3.58 (t, J=5.0 Hz, 4H), 3.34 (t, J=5.0 Hz, 4H), 2.28 (t, J=5.0 Hz, 2H), 2.78 (d, J=10.0 Hz, 2H), 1.70 (d, J=5.0 Hz, 2H), 1.55-1.51 (m, 3H), 1.47 (s, 9H).

Tert-butyl 4-(3-(4-methylpiperidin-1-yl)-4-nitrophenyl) piperazine-1-carboxylate (5d): To the mixture of 1-(5-Chloro-2-nitrophenyl)-4-methylpiperidine (1.0 g, 3.92 mmol) and tert-butyl piperazine-1-carboxylate (1.46 g, 7.85 mmol), in DMSO (10 mL) was added $K_2CO_3$ (1.62 g, 11.77 mmol). The reaction mixture was stirred at 110 °C for 12 h and then partitioned between EtOAc and brine. The organic layer was separated, dried over anhydrous $MgSO_4$, filtered, and concentrated under a vacuum. The resulting residue was purified by silica gel column chromatography (Hexane: EtOAc=3:7) to give tert-butyl 4-(3-(4-methylpiperidin-1-yl)-4-nitrophenyl)piperazine-1-carboxylate as a white solid (1.42 g, 89.8% yield). $^1$H NMR (500 MHz, $CDCl_3$) δ7.99 (d, J=10.0 Hz, 1H), 6.38 (d, J=10.0 Hz, 1H), 6.31 (s, 1H), 3.58 (t, J=5.0 Hz, 4H), 3.34 (t, J=5.0 Hz, 4H), 2.28 (t, J=5.0 Hz, 2H), 2.78 (d, J=10.0 Hz, 2H), 1.70 (d, J=5.0 Hz, 2H), 1.55-1.51 (m, 3H), 1.47 (s, 9H), 1.00 (d, J=5.0 Hz, 3H).

4-(4-methylpiperazin-1-yl)-2-(piperidin-1-yl)aniline (6a): To a mixture of 1-methyl-4-(4-nitro-3-(piperidin-1-yl)phenyl)piperazine (1.2 g, 3.94 mmol), and $NH_4Cl$ (2.10 g, 39.4 mmol) in THF/MeOH/$H_2O$ (10:5:3) (20 mL), was added Zn dust (2.57 g, 39.4 mmol) at 90 °C, then the mixture was refluxed for 1 h. After completion of the reaction, the reaction mixture was filtered through Celite and partitioned between EtOAc and brine. The organic layer was separated, dried over anhydrous $MgSO_4$, filtered, and concentrated in vacuo. The resulting residue was purified by silica gel column chromatography ($CH_2Cl_2$:MeOH=9:1) to give 4-(4-methylpiperazin-1-yl)-2-(piperidin-1-yl)aniline as a brown solid (0.98 g, 90.7% yield).

4-(4-Methylpiperazin-1-yl)-2-(4-methylpiperidin-1-yl) aniline (6b): To a mixture of 1-Methyl-4-(3-(4-methylpiperidin-1-yl)-4-nitrophenyl)piperazine (1.2 g, 3.76 mmol), and $NH_4Cl$ (2.01 g, 37.6 mmol) in THF/MeOH/$H_2O$ (10:5:3) (20 mL), was added Zn dust (2.46 g, 37.6 mmol) at 90 °C, then the mixture was refluxed for 1 h. After completion of the reaction, the reaction mixture was filtered through Celite and partitioned between EtOAc and brine. The organic layer was separated, dried over anhydrous $MgSO_4$, filtered, and concentrated in vacuo. The resulting residue was purified by silica gel column chromatography ($CH_2Cl_2$:MeOH=9:1) to give 4-(4-methylpiperazin-1-yl)-2-(4-methylpiperidin-1-yl) aniline as a brown solid (1.0 g, 92.0% yield).

Tert-butyl 4-(4-amino-3-(piperidin-1-yl)phenyl)piperazine-1-carboxylate (6c): To a mixture of tert-butyl 4-(4-nitro-3-(piperidin-1-yl)phenyl)piperazine-1-carboxylate (1.20 g, 3.07 mmol), and $NH_4Cl$ (1.64 g, 30.7 mmol) in THF/MeOH/$H_2O$ (10:5:3) (20 mL), was added Zn dust (2.0 g, 30.7 mmol) at 90 °C, then the mixture was refluxed for 1 h. After completion of the reaction, the reaction mixture was filtered through Celite and partitioned between EtOAc and brine. The organic layer was separated, dried over anhydrous $MgSO_4$, filtered, and concentrated in vacuo. The resulting residue was purified by silica gel column chromatography ($CH_2Cl_2$:MeOH=9:1) to give tert-butyl 4-(4-amino-3-(piperidin-1-yl)phenyl)piperazine-1-carboxylate as a brown solid (1.0 g, 90.3% yield).

Tert-butyl 4-(4-amino-3-(4-methylpiperidin-1-yl)phenyl) piperazine-1-carboxylate (6d): To a mixture of tert-butyl 4-(3-(4-methylpiperidin-1-yl)-4-nitrophenyl)piperazine-1-carboxylate (1.2 g, 2.96 mmol), and $NH_4Cl$ (1.58 g, 29.6 mmol) in THF/MeOH/$H_2O$ (10:5:3) (20 mL), was added Zn dust (1.93 g, 29.6 mmol) at 90 °C, then the mixture was refluxed for 1 h. After completion of the reaction, the reaction mixture was filtered through Celite and partitioned between EtOAc and brine. The organic layer was separated, dried over anhydrous $MgSO_4$, filtered, and concentrated in vacuo. The resulting residue was purified by silica gel column chromatography ($CH_2Cl_2$:MeOH=9:1) to give tert-butyl 4-(4-amino-3-(piperidin-1-yl)phenyl)piperazine-1-carboxylate as a brown solid (1.0 g, 90.0% yield).

5-Cyano-N-(4-(4-methylpiperazin-1-yl)-2-(piperidin-1-yl)phenyl)furan-2-carboxamide (1a) (JHU11744): To the mixture of 4-(4-methylpiperazin-1-yl)-2-(piperidin-1-yl) aniline (0.5 g, 1.82 mmol), 5-cyanofuran-2-carboxylic acid (0.3 g, 2.18 mmol), HATU (0.83 g, 2.18 mmol), in DMF (10 mL) was added DIPEA (0.63 mL, 3.64 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give 5-cyano-N-(4-(4-methylpiperazin-1-yl)-2-(piperidin-1-yl)phenyl)furan-2-carboxamide as a yellow solid (0.6 g, 84.5% yield). $^1$H NMR (500 MHz, $CDCl_3$) δ 9.53 (s, 1H), 8.31 (d, J=8.7 Hz, 1H), 7.23 (d, J=16.6 Hz, 2H), 6.80 (s, 1H), 6.72 (d, J=8.8 Hz, 1H), 3.20 (s, 4H), 2.85 (s, 4H), 2.59 (s, 4H), 2.36 (s, 3H), 1.80 (s, 4H), 1.65 (s, 2H).

5-Cyano-N-(4-(4-methylpiperazin-1-yl)-2-(4-methylpiperidin-1-yl)phenyl)furan-2-carboxamide (1c) (JHU11734): To the mixture of 4-(4-Methylpiperazin-1-yl)-2-(4-methylpiperidin-1-yl)aniline (0.5 g, 1.73 mmol), 5-cyanofuran-2-carboxylic acid (0.28 g, 2.08 mmol), HATU (0.79 g, 2.08 mmol), in DMF (10 mL) was added DIPEA (0.60 mL, 3.46 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give 5-cyano-N-(4-(4-methylpiperazin-1-yl)-2-(4-methylpiperidin-1-yl)phenyl) furan-2-carboxamide as a yellow solid (0.62 g, 87.8% yield). $^1$H NMR (500 MHz, $CDCl_3$) δ9.60 (s, 1H), 8.30 (d, J=5.0 Hz, 1H), 7.25 (d, J=5.0 Hz, 1H), 7.21 (d, J=5.0 Hz, 1H), 6.79 (s, 1H), 6.72 (d, J=5.0 Hz, 1H), 3.19 (t, J=5.0 Hz, 4H), 2.99 (t, J=5.0 Hz, 2H), 2.73 (t, J=10.0 Hz, 2H), 2.59 (t, J=5.0 Hz, 4H), 2.36 (s, 3H), 1.84 (d, J=10.0 Hz, 2H), 1.52-1.47 (m, 3H), 1.07 (d, J=5.0 Hz, 3H).

4-Cyano-N-(4-(4-methylpiperazin-1-yl)-2-(4-methylpiperidin-1-yl)phenyl)-1H-pyrrole-2-carboxamide (1e) (JHU11761): To the mixture of 4-(4-Methylpiperazin-1-yl)-2-(4-methylpiperidin-1-yl)aniline (0.5 g, 1.73 mmol), 5-cyanofuran-2-carboxylic acid (0.28 g, 2.08 mmol), HATU (0.79 g, 2.08 mmol), in DMF (10 mL) was added DIPEA (0.60 mL, 3.46 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give 4-cyano-N-(4-(4-methylpiperazin-1-yl)-2-(4-methylpiperidin-1-yl)phenyl)-1H-pyrrole-2-carboxamide as a brown solid (0.62 g, 87.8% yield). $^1$H NMR (500 MHz, $CDCl_3$) δ10.58 (s, 1H), 9.0 (s, 1H), 8.25 (d, J=5.0 Hz, 1H), 7.45 (s, 1H), 6.82 (d, J=10.0 Hz, 2H), 6.72 (d, J=5.0 Hz, 1H), 3.19 (t, J=5.0 Hz, 4H), 2.99 (t, J=5.0 Hz, 2H), 2.73 (t, J=10.0 Hz, 2H), 2.60 (t, J=5.0 Hz, 4H), 2.37 (s, 3H), 1.84 (d, J=10.0 Hz, 3H), 1.52-1.47 (m, 2H), 1.08 (d, J=5.0 Hz, 3H).

4-Cyano-N-(4-(4-methylpiperazin-1-yl)-2-(piperidin-1-yl)phenyl)furan-2-carboxamide (1g) (JHU11765): To the mixture of 4-(4-methylpiperazin-1-yl)-2-(piperidin-1-yl) aniline (0.5 g, 1.82 mmol), 4-cyanofuran-2-carboxylic acid (0.3 g, 2.18 mmol), HATU (0.83 g, 2.18 mmol), in DMF (10 mL) was added DIPEA (0.63 mL, 3.64 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give 4-cyano-N-(4-(4-methylpiperazin-1-yl)-2-(piperidin-1-yl)phenyl)furan-2-carboxamide as a pale yellow solid (0.62 g, 86.1% yield). $^1$H NMR (500 MHz, $CDCl_3$) δ9.41 (s, 1H), 8.31 (d, J=8.7 Hz, 1H), 8.03 (s, 1H), 7.33 (s, 1H), 6.78 (s, 1H), 6.72 (d, J=8.8 Hz, 1H), 3.19 (s, 4H), 2.83 (s, 4H), 2.59 (s, 4H), 2.36 (s, 3H), 1.76 (s, 4H), 1.63 (s, 2H).

5-Cyano-N-(4-(4-methylpiperazin-1-yl)-2-(piperidin-1-yl)phenyl)furan-3-carboxamide (1h) (JHU11766): To the mixture of 4-(4-methylpiperazin-1-yl)-2-(piperidin-1-yl) aniline (0.5 g, 1.82 mmol), 5-cyanofuran-3-carboxylic acid (0.3 g, 2.18 mmol), HATU (0.83 g, 2.18 mmol), in DMF (10 mL) was added DIPEA (0.63 mL, 3.64 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give 5-cyano-N-(4-(4-methylpiperazin-1-yl)-2-(piperidin-1-yl)phenyl)furan-3-carboxamide as a yellow solid (0.6 g, 84.5% yield). $^1$H NMR (500 MHz, $CDCl_3$) δ 8.92 (s, 1H), 8.28 (d, J=8.3 Hz, 1H), 8.11 (s, 1H), 7.37 (s, 1H), 6.79 (s, 1H), 6.73 (d, J=8.7 Hz, 1H), 3.18 (s, 4H), 2.82 (s, 4H), 2.59 (s, 4H), 2.36 (s, 3H), 1.74 (s, 4H), 1.65 (s, 2H).

6-Fluoro-N-(4-(4-methylpiperazin-1-yl)-2-(piperidin-1-yl)phenyl)picolinamide (1i) (JHU11767): To the mixture of 4-(4-methylpiperazin-1-yl)-2-(piperidin-1-yl)aniline (0.5 g, 1.82 mmol), 6-fluoropicolinic acid (0.308 g, 2.18 mmol), HATU (0.83 g, 2.18 mmol), in DMF (10 mL) was added DIPEA (0.63 mL, 3.64 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give 5-cyano-N-(4-(4-methylpiperazin-1-yl)-2-(piperidin-1-yl) phenyl)furan-2-carboxamide as a yellow solid (0.52 g, 72.2% yield). $^1$H NMR (500 MHz, $CDCl_3$) (10.66 (s, 1H), 8.45 (d, J=8.8 Hz, 1H), 8.17 (d, J=7.0 Hz, 1H), 7.10 (d, J=8.2

Hz, 1H), 6.78 (s, 1H), 6.72 (d, J=8.8 Hz, 1H), 3.21 (s, 4H), 2.87 (s, 4H), 2.62 (s, 4H), 2.38 (s, 3H), 1.87 (s, 4H), 1.64 (s, 2H).

6-Bromo-N-(4-(4-methylpiperazin-1-yl)-2-(piperidin-1-yl)phenyl)picolinamide (1i) (JHU11769): To the mixture of 4-(4-methylpiperazin-1-yl)-2-(piperidin-1-yl)aniline (0.5 g, 1.82 mmol), 6-bromopicolinic acid (0.441 g, 2.18 mmol), HATU (0.83 g, 2.18 mmol), in DMF (10 mL) was added DIPEA (0.63 mL, 3.64 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give 5-cyano-N-(4-(4-methylpiperazin-1-yl)-2-(piperidin-1-yl) phenyl)furan-2-carboxamide as a yellow solid (0.53 g, 63.8% yield). $^1H$ NMR (500 MHz, $CDCl_3$) δ10.89 (s, 1H), 8.45 (d, J=8.7 Hz, 1H), 8.23 (d, J=7.0 Hz, 1H), 7.74 (t, J=7.6 Hz, 1H), 7.62 (d, J=7.3 Hz, 1H), 6.79 (s, 1H), 6.73 (d, J=8.8 Hz, 1H), 3.20 (s, 4H), 2.87 (s, 4H), 2.60 (s, 4H), 2.36 (s, 3H), 1.91 (s, 4H), 1.64 (s, 2H).

Tert-butyl 4-(4-(5-cyanofuran-2-carboxamido)-3-(piperidin-1-yl)phenyl)piperazine-1-carboxylate (7a): To the mixture of tert-butyl 4-(4-amino-3-(piperidin-1-yl)phenyl)piperazine-1-carboxylate (0.5 g, 1.38 mmol), 5-cyanofuran-2-carboxylic acid (0.23 g, 1.66 mmol), HATU (0.63 g, 1.66 mmol), in DMF (10 mL) was added DIPEA (0.48 mL, 2.76 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give tert-butyl 4-(4-(5-cyanofuran-2-carboxamido)-3-(piperidin-1-yl)phenyl)piperazine-1-carboxylate as a yellow solid (0.60 g, 90.9% yield). $^1H$ NMR (500 MHz, $CDCl_3$) 59.59 (s, 1H), 8.31 (d, J=5.0 Hz, 1H), 7.25 (d, J 10=5.0 Hz, 1H), 7.21 (d, J=5.0 Hz, 1H), 6.79 (s, 1H), 6.72 (d, J=5.0 Hz, 1H), 3.58 (t, J=5.0 Hz, 4H), 3.10 (t, J=5.0 Hz, 4H), 2.99 (t, J=5.0 Hz, 2H), 2.72 (t, J=10.0 Hz, 2H), 1.83 (d, J=10.0 Hz, 2H), 1.55-1.51 (m, 3H), 1.49 (s, 9H).

Tert-butyl 4-(4-(5-cyanofuran-2-carboxamido)-3-(4-methylpiperidin-1-yl)phenyl)piperazine-1-carboxylate (7b): To the mixture of tert-butyl 4-(4-amino-3-(4-methylpiperidin-1-yl)phenyl)piperazine-1-carboxylate (0.5 g, 1.33 mmol), 5-cyanofuran-2-carboxylic acid (0.22 g, 1.60 mmol), HATU (0.61 g, 1.60 mmol), in DMF (10 mL) was added DIPEA (0.46 mL, 2.66 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give Tert-butyl 4-(4-(5-cyanofuran-2-carboxamido)-3-(4-methylpiperidin-1-yl)phenyl)piperazine-1-carboxylate as a yellow solid (0.58 g, 88.0% yield). $^1H$ NMR (500 MHz, $CDCl_3$) δ9.59 (s, 1H), 8.31 (d, J=5.0 Hz, 1H), 7.25 (d, J=5.0 Hz, 1H), 7.21 (d, J=5.0 Hz, 1H), 6.79 (s, 1H), 6.72 (d, J=5.0 Hz, 1H), 3.58 (t, J=5.0 Hz, 4H), 3.10 (t, J=5.0 Hz, 4H), 2.99 (t, J=5.0 Hz, 2H), 2.72 (t, J=10.0 Hz, 2H), 1.83 (d, J=10.0 Hz, 2H), 1.55-1.51 (m, 3H), 1.49 (s, 9H), 1.07 (d, J=5.0 Hz, 3H).

Tert-butyl 4-(4-(4-cyano-1H-pyrrole-2-carboxamido)-3-(4-methylpiperidin-1-yl)phenyl)piperazine-1-carboxylate (7c): To the mixture of tert-butyl 4-(4-amino-3-(4-methylpiperidin-1-yl)phenyl)piperazine-1-carboxylate (0.5 g, 1.33 mmol), 4-cyano-1H-pyrrole-2-carboxylic acid (0.23 g, 1.60 mmol), HATU (0.61 g, 1.60 mmol), in DMF (10 mL) was added DIPEA (0.46 mL, 2.66 mmol). The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give Tert-butyl 4-(4-(4-cyano-1H-pyrrole-2-carboxamido)-3-(4-methylpiperidin-1-yl)phenyl)piperazine-1-carboxylate as a yellow solid (0.58 g, 88.0% yield). $^1H$ NMR (500 MHz, $CDCl_3$) δ10.40 (s, 1H), 8.99 (s, 1H), 8.26 (d, J=5.0 Hz, 1H), 7.45 (s, 1H), 6.83 (d, J=10.0 Hz, 2H), 6.73 (d, J=5.0 Hz, 1H), 3.58 (t, J=5.0 Hz, 4H), 3.10 (t, J=5.0 Hz, 4H), 2.99 (t, J=5.0 Hz, 2H), 2.72 (t, J=10.0 Hz, 2H), 1.83 (d, J=10.0 Hz, 2H), 1.55-1.51 (m, 3H), 1.49 (s, 9H), 1.07 (d, J=5.0 Hz, 3H).

5-Cyano-N-(4-(piperazin-1-yl)-2-(piperidin-1-yl)phenyl) furan-2-carboxamide (1b) (JHU11745): To a solution of tert-butyl 4-(4-(5-cyanofuran-2-carboxamido)-3-(piperidin-1-yl)phenyl)piperazine-1-carboxylate (0.5 g, 1.04 mmol) in methylene chloride (5 mL) was added trifluoroacetic acid (0.39 mL, 5.21 mmol) dropwise at 0 °C, and then, the mixture was stirred at room temperature for 12 h. After completion of the reaction, the reaction mixture was concentrated under reduced pressure. The resulting residue was purified by silica gel column chromatography ($CH_2Cl_2$:MeOH=9:1) to give 5-cyano-N-(4-(piperazin-1-yl)-2-(piperidin-1-yl)phenyl)furan-2-carboxamide as a pale yellow solid (0.3 g, 76.0% yield). $^1H$ NMR (500 MHz, $CDCl_3$) δ9.54 (s, 1H), 8.31 (d, J=5.0 Hz, 1H), 7.25 (d, J=5.0 Hz, 1H), 7.21 (d, J=5.0 Hz, 1H), 6.79 (s, 1H), 6.73 (d, J=8.8 Hz, 1H), 3.18 (s, 4H), 3.11 (s, 4H), 2.85 (s, 4H), 2.36 (s, 1H), 1.80 (s, 4H), 1.66 (s, 2H).

5-Cyano-N-(2-(4-methylpiperidin-1-yl)-4-(piperazin-1-yl)phenyl)furan-2-carboxamide (1d) (JHU11735): To a solution of tert-butyl 4-(4-(5-cyanofuran-2-carboxamido)-3-(4-methylpiperidin-1-yl)phenyl)piperazine-1-carboxylate (0.5 g, 1.01 mmol) in methylene chloride (5 mL) was added trifluoroacetic acid (0.37 mL, 5.05 mmol) dropwise at 0 °C, and then, the mixture was stirred at room temperature for 12 h. After completion of the reaction, the reaction mixture was concentrated under reduced pressure. The resulting residue was purified by silica gel column chromatography ($CH_2Cl_2$:MeOH=9:1) to give 5-cyano-N-(2-(4-methylpiperidin-1-yl)-4-(piperazin-1-yl)phenyl)furan-2-carboxamide as a pale yellow solid (0.32 g, 80.4% yield). $^1H$ NMR (500 MHz, $CDCl_3$) δ9.60 (s, 1H), 8.31 (d, J=5.0 Hz, 1H), 7.25 (d, J=5.0 Hz, 1H), 7.21 (d, J=5.0 Hz, 1H), 6.79 (s, 1H), 6.72 (d, J=5.0 Hz, 1H), 3.15 (t, J=5.0 Hz, 4H), 3.08 (t, J=5.0 Hz, 4H), 2.99 (t, J=5.0 Hz, 2H), 2.73 (t, J=10.0 Hz, 2H), 1.84 (d, J=10.0 Hz, 2H), 1.57 (s, 1H), 1.55-1.51 (m, 3H), 1.07 (d, J=5.0 Hz, 3H).

4-Cyano-N-(2-(4-methylpiperidin-1-yl)-4-(piperazin-1-yl)phenyl)-1H-pyrrole-2-carboxamide (if) (JHU11762): To a solution of tert-butyl 4-(4-(4-cyano-1H-pyrrole-2-carboxamido)-3-(4-methylpiperidin-1-yl)phenyl)piperazine-1-carboxylate (0.5 g, 1.02 mmol) in methylene chloride (5 mL) was added trifluoroacetic acid (0.37 mL, 5.05 mmol) dropwise at 0 °C, and then, the mixture was stirred at room temperature for 12 h. After completion of the reaction, the reaction mixture was concentrated under reduced pressure. The resulting residue was purified by silica gel column chromatography ($CH_2Cl_2$:MeOH=9:1) to give 4-cyano-N-(2-(4-methylpiperidin-1-yl)-4-(piperazin-1-yl)phenyl)-1H-pyrrole-2-carboxamide as a pale white solid (0.30 g, 78.4% yield). $^1H$ NMR (500 MHz, MeOD) δ10.45 (s, 1H), 8.98 (s, 1H), 8.24 (d, J=5.0 Hz, 1H), 7.45 (d, J=5.0 Hz, 1H), 6.83 (d, J=10.0 Hz, 2H), 6.72 (d, J=5.0 Hz, 1H), 3.15 (t, J=5.0 Hz, 4H), 3.08 (t, J=5.0 Hz, 4H), 2.99 (t, J=5.0 Hz, 2H), 2.73 (t, J=10.0 Hz, 2H), 1.84 (d, J=10.0 Hz, 2H), 1.57 (s, 1H), 1.55-1.51 (m, 3H), 1.07 (d, J=5.0 Hz, 3H).

5-Cyano-N-(4-(4-(2-fluoroethyl)piperazin-1-yl)-2-(piperidin-1-yl)phenyl)furan-2-carboxamide (1k) (JHU11763): To a solution of 5-cyano-N-(4-(piperazin-1-yl)-2-(piperidin-1-yl)phenyl)furan-2-carboxamide (1b) (0.1 g, 0.26 mmol) in Acetonitrile (1 mL) was added 2-fluoroethyl tosylate (0.07 g, 0.31 mmol) and triethylamine (0.053 g, 0.52 mmol). The reaction mixture was stirred at 90 °C overnight and then partitioned between EtOAc and brine. The organic layer was separated, dried over anhydrous $MgSO_4$, filtered, and concentrated under a vacuum. The resulting residue was purified by silica gel column chromatography (Methanol:Dichloromethane=0.5:9.5) to give 1k as a pale yellow solid (0.06 g, 53.57% yield). $^1$H NMR (500 MHz, $CDCl_3$) δ9.53 (s, 1H), 8.31 (d, J=8.7 Hz, 1H), 7.25 (s, 1H), 7.21 (s, 1H), 6.79 (s, 1H), 6.72 (d, J=8.8 Hz, 1H), 4.67 (s, 1H), 4.58 (s, 1H), 3.21 (s, 4H), 2.89-2.68 (m, 10H), 1.80 (s, 4H), 1.65 (s, 2H).

4-Cyano-N-(4-(4-(2-fluoroethyl)piperazin-1-yl)-2-(4-methylpiperidin-1-yl)phenyl)-1H-pyrrole-2-carboxamide (11) (JHU11764): To a solution of 4-Cyano-N-(2-(4-methylpiperidin-1-yl)-4-(piperazin-1-yl)phenyl)-1H-pyrrole-2-carboxamide (if) (0.1 g, 0.25 mmol) in Acetonitrile (1 mL) was added 2-fluoroethyl tosylate (0.066 g, 0.305 mmol) and triethylamine (0.051 g, 0.50 mmol). The reaction mixture was stirred at 90 °C overnight and then partitioned between EtOAc and brine. The organic layer was separated, dried over anhydrous $MgSO_4$, filtered, and concentrated under a vacuum. The resulting residue was purified by silica gel column chromatography (Methanol:Dichloromethane=0.5:9.5) to give 11 as a pale yellow solid (0.057 g, 51.35% yield). $^1$H NMR (500 MHz, $CDCl_3$) δ10.83 (s, 1H), 9.01 (s, 1H), 8.26 (d, J=8.4 Hz, 1H), 7.45 (s, 1H), 6.83 (d, J=15.7 Hz, 2H), 6.74 (d, J=8.6 Hz, 1H), 4.67 (s, 1H), 4.58 (s, 1H), 3.21 (s, 4H), 2.98 (d, J=11.2 Hz, 2H), 2.84-2.67 (m, 8H), 1.85 (d, J=12.8 Hz, 2H), 1.43-1.26 (m, 3H), 1.08 (d, J=6.4 Hz, 3H).

N-(4-(4-(2-bromoethyl)piperazin-1-yl)-2-(piperidin-1-yl)phenyl)-S-cyanofuran-2-carboxamide (1m) (JHU11768): To a solution of 5-cyano-N-(4-(piperazin-1-yl)-2-(piperidin-1-yl)phenyl)furan-2-carboxamide (1b) (0.01 g, 0.026 mmol) in Acetonitrile (1 mL) was added 1,2-dibromoethane (0.039 g, 2.10 mmol) and triethylamine (0.0053 g, 0.052 mmol). The reaction mixture was stirred at 90 °C overnight and then partitioned between EtOAc and brine. The organic layer was separated, dried over anhydrous $MgSO_4$, filtered, and concentrated under a vacuum. The resulting residue was purified by silica gel column chromatography (Methanol:Dichloromethane=0.5:9.5) to give 1 m as a pale yellow solid (0.01 g, 83.33% yield). $^1$H NMR (500 MHz, $CDCl_3$) δ9.53 (s, 1H), 8.31 (d, J=8.7 Hz, 1H), 7.23 (d, J=17.5 Hz, 2H), 6.80 (s, 1H), 6.72 (d, J=8.8 Hz, 1H), 3.20 (s, 4H), 2.84 (s, 4H), 2.69 (s, 4H), 2.64 (s, 2H), 1.80 (s, 4H), 1.65 (s, 2H).

4-(4-Amino-phenyl)-3,6-dihydro-2H-pyridine-1-carboxylic acid tert-butyl ester (10): A solution of 4-(4,4,5,5-tetramethyl-[1,3,2]-dioxaborolan-2-yl)-phenylamine (4.0 g, 18 mmol), 4-trifluoromethanesulfonyloxy-3,6-dihydro-2H-pyridine-1-carboxylic acid tert-butyl ester (7.4 g, 22 mmol), and 2 M aqueous $Na_2CO_3$ (80 mL) in toluene (160 mL) and EtOH (80 mL) was placed under argon and heated to 80 °C for 3 h. The mixture was washed with 1 M aqueous NaOH, and the organic layer was removed, dried ($Na_2SO_4$), and concentrated in vacuo. The residue was purified by silica gel chromatography, eluting with 20% EtOAc/hexanes to afford 3.2 g (63%) of the title compound as a yellow foam. $^1$H NMR ($CDCl_3$, 500 MHz): δ 7.18-7.23 (m, 2H, J=8.4 Hz), 6.64-6.69 (m, 2H, J=8.6 Hz), 5.90 (br s, 1H), 4.02-4.08 (m, 2H), 3.68 (s, 2H), 3.62 (t, 2H, J=5.6 Hz), 2.48 (br s, 2H), 1.49 (s, 9H).

4-(4-Amino-phenyl)-piperidine-1-carboxylic Acid tert-butyl ester (11): A solution of 4-(4-amino-phenyl)-3,6-dihydro-2H-pyridine-1-carboxylic acid tert-butyl ester (0.350 g, 1.28 mmol) in methanol was hydrogenated over 10% Pd/C at 20 psi for 1 h. The solution was filtered through diatomaceous earth, and the filtrate was concentrated to give 0.35 g (100%) of the title compound as a yellow solid. $^1$H NMR ($CDCl_3$, 500 MHz): δ 6.96-7.01 (d, 2H, J=8.4 Hz), 6.62-6.67 (d, 2H, J=8.4 Hz), 4.21 (br s, 2H), 3.58 (br s, 2H), 2.77 (t, 2H, J=12.6 Hz), 2.53 (tt, 1H, J=12.1, 3.5 Hz), 1.77 (d, 2H, J=12.3 Hz), 1.52-1.59, (m, 2H), 1.48 (s, 9H).

4-(4-Amino-3-bromo-phenyl)-piperidine-1-carboxylic Acid tert-butyl ester (12): To a solution of 4-(4-amino-phenyl)-piperidine-1-carboxylic acid tert-butyl ester (0.20 g, 0.71 mmol) in $CH_2Cl_2$ (3 mL) was added N-bromosuccinimide (NBS) (0.13 g, 0.71 mmol), and the reaction was stirred at room temperature for 10 h. The reaction was diluted with EtOAc (10 mL) and washed with saturated aqueous $NaHCO_3$ (2×10 mL) and brine (10 mL). Concentration of the organic layer gave 0.26 g (100%) of the title compound as a yellow foam. 1H NMR ($CDCl_3$, 500 MHz): δ 7.27 (d, 1H, J=2.1 Hz), 6.96 (dd, 1H, J=8.1, 1.9 Hz), 6.73 (d, 1H, J=8.1 Hz), 4.24 (br s, 2H), 4.01 (br s, 2H), 2.78 (t, 2H, J=12.2 Hz), 2.53 (tt, 1H, J=12.2, 3.3 Hz), 1.79 (d, 2H, J=12.6 Hz), 1.52-1.59 (m, 2H), 1.50 (s, 9H).

4-(4-Amino-3-cyclohex-1-enyl-phenyl)-piperidine-1-carboxylic acid tert-butyl ester (13): 4-(4-Amino-3-bromo-phenyl)-piperidine-1-carboxylic acid tert-butyl ester (0.13 g, 0.42 mmol), cyclohex-1-enyl boronic acid 4 (0.08 g, 0.63 mmol), Pd(dppf)$Cl_2$. DCM (0.034 g, 0.042) aqueous 2 M $Na_2CO_3$ (1.5 mL), in 1,4-dioxane were heated at 100 °C for 20 h. The reaction was diluted with EtOAc (10 mL) and washed with saturated aqueous $NaHCO_3$ (2×10 mL) and brine (10 mL), and the organic layer was dried over $Na_2SO_4$ and then concentrated. The residue was purified silica gel chromatography, 30% EtOAc/hexane to give 0.12 g (85%) of the title compound as a yellow oil. $^1$H NMR ($CDCl_3$, 500 MHz): δ 6.90 (dd, 1H, J=8.1, 2.1 Hz), 6.85 (d, 1H, J=1.9 Hz), 6.67 (d, 1H, J=8.1 Hz), 5.76 (dq, 1H, J=3.5, 1.8 Hz), 4.23 (br s, 2H), 3.71 (s, 2H), 2.79 (t, 2H, J=12.7 Hz), 2.54 (tt, 1H, J=12.3, 3.4 Hz), 2.22-2.29 (m, 2H), 2.16-2.22 (m, 2H), 1.62-1.85 (m, 8H), 1.50 (s, 9H).

(4-{[4-Cyano-1-(2-trimethylsilanyl-ethoxymethyl)-1H-imidazole-2-carbonyl]-amino}-3-cyclohex-1-enyl-phenyl)-piperidine-1-carboxylic acid tert-butyl ester (15): To a solution of 4-cyano-1-(2-trimethylsilanyl-ethoxymethyl)-1H-imidazole-2-carboxylate potassium salt (3.34 g, 10.9 mmol) in 20 mL of DMF were added DIPEA (3.80 mL, 21.8 mmol) and HATU (11.02 g, 12.0 mmol), and the reaction was stirred at 25 °C for 15 min. A solution of 4-(4-amino-3-cyclohex-1-enyl-phenyl)-piperidine-1-carboxylic acid tert-butyl ester (3.92 g, 11.0 mmol) in 10 mL of DMF was added, and the reaction was stirred for 12 h at 25 °C. The reaction was diluted with EtOAc (60 mL) and washed with saturated aqueous $NaHCO_3$ (2×60 mL) and brine (100 mL), and the organic layer was dried over $Na_2SO_4$ and then concentrated. The residue was purified by flash chromatography (silica gel, 2% EtOAc/$CH_2Cl_2$) to give 5.5 g (85%) of the title compound as a yellow oil. $^1$H NMR ($CDCl_3$, 500 MHz): δ 9.68 (s, 1H), 8.25 (d, 1H, J=8.4 Hz), 7.78 (s, 1H), 7.12 (dd, 1H, J=8.6, 2.1 Hz), 7.02 (d, 1H, J=2.1 Hz), 5.96 (s, 2H), 5.83 (dt, 1H, J=3.6, 1.9 Hz), 4.25 (br s, 2H), 3.63-3.69 (m, 2H), 2.80 (t, 2H, J=11.7 Hz), 2.63 (tt, 1H, J=12.2, 3.5 Hz), 2.27-2.33 (m, 2H), 2.20-2.27 (m, 2H), 1.77-1.87 (m, 6H), 1.56-1.68 (m, 2H), 1.49 (s, 9H), 0.95-1.00 (m, 2H), 0.01 (s, 9H).

4-Cyano-1H-imidazole-2-carboxylic acid (2-Cyclohex-1-enyl-4-piperidin-4-yl-phenyl)-amide trifluoroacetic acid salt (16): To a solution of 4-(4-{[4-cyano-1-(2-trimethylsilanyl-ethoxymethyl)-1Himidazole-2-carbonyl]-amino}-3-cyclohex-1-enyl-phenyl)-piperidine-1-carboxylic acid tert-butyl ester 7 (1.50 g, 2.48 mmol) in 10 mL of $CH_2Cl_2$ was added 3 mL of TFA, and the solution was stirred for 20 h at 25 °C. The reaction was diluted with 5 mL of EtOH and then concentrated. The residue was crystallized from methanol and ethyl ether to give 0.85 g (70%) of the title compound as a white solid. $^1$H NMR ($CD_3OD$, 500 MHz): δ 8.18 (d, 1H, J=8.4 Hz), 8.04 (s, 1H), 7.22 (dd, 1H, J=8.6, 2.1 Hz), 7.12 (d, 1H, J=2.3 Hz), 5.76 (m, 1H), 3.54 (m, 2H), 3.16 (m, 2H), 2.92 (m, 1H), 2.30 (m, 4H), 2.10 (m, 2H), 1.87 (m, 6H).

4-Cyano-1H-imidazole-2-carboxylic Acid {2-Cyclohex-1-enyl-4-[1-(2-dimethylamino-acetyl)-piperidin-4-yl]-phenyl}-amide (1g) (JHU11759): A suspension of 4-cyano-1H-imidazole-2-carboxylic acid (2-cyclohex-1-enyl-4-piperidin-4-yl-phenyl)-amide trifluoroacetic acid salt (0.655 g, 1.34 mmol) in DMF (15 mL) were added HATU (0.61 g, 1.60 mmol) and DIPEA (0.932 mL, 5.35 mmol) and stirred for 15 mins. Dimethylglycine (0.15 g, 1.47 mmol) was then added. The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give the title compound as a white solid. $^1$H NMR ($CDCl_3$, 500 MHz): δ 9.49 (s, 1H), 8.24 (d, 1H, J=8.3 Hz), 7.70 (s, 1H), 7.12 (dd, 1H, J=8.4, 2.1 Hz), 7.01 (d, 1H, J=2.1 Hz), 5.82 (m, 1H), 4.75 (d, 1H, J=13.4 Hz), 4.13 (d, 1H, J=13.4 Hz), 3.57 (d, 1H, J=14.2 Hz), 3.18 (d, 1H, J=14.2 Hz), 3.12 (td, 1H, J=13.3, 2.4 Hz), 2.73 (dddd, 1H, J=11.9, 11.9, 3.8, 3.8 Hz), 2.65 (ddd, 1H, J=13.3, 13.3, 2.4 Hz), 2.40 (s, 6H), 2.18-2.32 (m, 4H), 1.60-1.98 (m, 9H).

Tert-butyl ((4-(6-(4-cyano-1H-imidazole-2-carboxamido)-2',3',4',5'-tetrahydro-[1,1'-biphenyl]-3-yl)piperidin-1-yl)methyl)(methyl)carbamate (17): A suspension of 4-cyano-1H-imidazole-2-carboxylic acid (2-cyclohex-1-enyl-4-piperidin-4-yl-phenyl)-amide trifluoroacetic acid salt (0.15 g, 0.30 mmol) in DMF (15 mL) were added HATU (0.14 g, 0.36 mmol) and DIPEA (0.212 mL, 1.22 mmol) and stirred for 15 mins. N-(tert-butoxycarbonyl)-N-methylglycine (0.063 g, 0.33 mmol) was then added. The reaction mixture was stirred at room temperature overnight and then partitioned between EtOAc and brine. The organic layer was separated, dried over anhydrous $MgSO_4$, filtered, and concentrated under a vacuum. The resulting residue was purified by silica gel column chromatography ($CH_2Cl_2$:MeOH=9:1) to give the title compound as a white solid. $^1$H NMR ($CDCl_3$, 500 MHz): δ 12.57 (s, 1H), 9.53 (s, 1H), 8.27 (d, J=5.0 Hz, 1H), 7.75 (s, 1H), 7.15-7.04 (m, 2H), 5.86 (s, 1H), 4.80 (s, 1H), 4.24-3.95 (m, 3H), 3.18 (d, J=10.0 Hz, 1H), 2.95 (s, 3H), 2.74-2.61 (m, 2H), 2.32-2.25 (m, 4H), 1.85-1.73 (m, 6H), 1.49 (s, 9H).

4-Cyano-N-(5-(1-(methylglycyl)piperidin-4-yl)-2',3',4',5'-tetrahydro-[1,1'-biphenyl]-2-yl)-1H-imidazole-2-carboxamide (1h) (JHU11760): To a solution of tert-butyl ((4-(6-(4-cyano-1H-imidazole-2-carboxamido)-2',3',4',5'-tetrahydro-[1,1'-biphenyl]-3-yl)piperidin-1-yl)methyl)(methyl)carbamate (0.1 g, 0.18 mmol) in methylene chloride (5 mL) was added trifluoroacetic acid (0.056 mL, 0.73 mmol) dropwise at 0 °C, and then, the mixture was stirred at room temperature for 12 h. After completion of the reaction, the reaction mixture was concentrated under reduced pressure. The resulting residue was purified by silica gel column chromatography ($CH_2Cl_2$:MeOH=9:1) to give 4-cyano-N-(5-(1-(methylglycyl)piperidin-4-yl)-2',3',4',5'-tetrahydro-[1,1'-biphenyl]-2-yl)-1H-imidazole-2-carboxamide as a pale yellow solid (0.04 g, 46.0% yield). $^1$H NMR ($CDCl_3$, 500 MHz): δ 9.51 (s, 1H), 8.14 (d, J=5.0 Hz, 1H), 7.65 (s, 1H), 6.97-6.85 (m, 2H), 5.76 (s, 1H), 4.73 (d, J=10.0, 1H), 4.00-3.66 (m, 3H), 3.14 (d, J=10.0 Hz, 1H), 2.71-2.67 (m, 6H), 2.24 (d, J=5.0, 3H), 2.17-2.15 (m, 1H), 1.87-1.74 (s, 8H).

Example 3

Binding Affinity of Csf1R Derivatives 1a, 1c, 1e, 1g-11

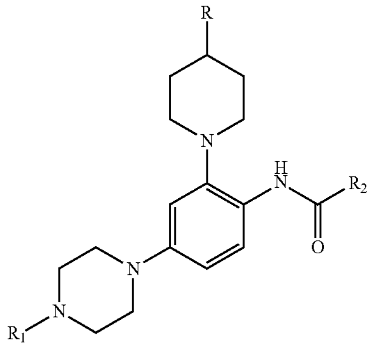

| Compound Name | R | $R_1$ | $R_2$ | IC50, nM Illig et al., 2008 | $IC_{50}$, nM* | $K_D$, nM** |
|---|---|---|---|---|---|---|
| 1a JHU11744 | H | $CH_3$ | 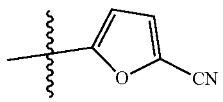 [SMILES: *c1ccc(C#N)o1] | 0.8 | 4.1 | 8.2 |
| 1c JHU11734 | $CH_3$ | $CH_3$ | 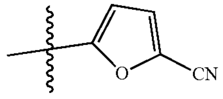 [SMILES: *c1ccc(C#N)o1] | 1 | 1.9 | 2.5 |

-continued

| Compound Name | R | $R_1$ | $R_2$ | IC50, nM Illig et al., 2008 | $IC_{50}$, nM* | $K_D$, nM** |
|---|---|---|---|---|---|---|
| 1e JHU11761 | $CH_3$ | $CH_3$ | 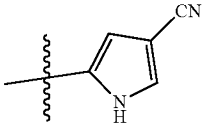 [SMILES: *c1cc(C#N)c[nH]1] | 0.8 | 3.94 | 0.54 |
| 1g JHU11765 | H | $CH_3$ | 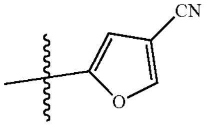 [SMILES: *c1cc(C#N)co1] | | | >1000 |
| 1h JHU11766 | H | $CH_3$ | 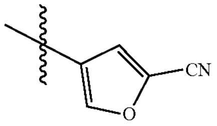 [SMILES: *c1coc(C#N)c1] | | | >1000 |
| 1i JHU11767 | H | $CH_3$ | 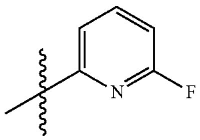 [SMILES: *c1cccc(F)n1] | | | 30 |
| 1k JHU11763 | H | $-CH_2CH_2F$ | 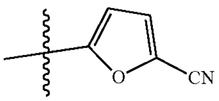 [SMILES: *c1ccc(C#N)o1] | | 12.9 | 32 |
| 1l JHU11764 | $CH_3$ | $-CH_2CH_2F$ | 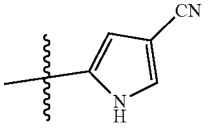 [SMILES: *c1cc(C#N)c[nH]1] | | 3.14 | 2.6 |

*CSF1R Human RTK Kinase. Enzymatic Radiometric Assay, Eurofins, commercial assay;

**CSF1R competition binding assay, KinomeScan, DiscoverX, commercial assay

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Masgrau R, Guaza C, Ransohoff R M, Galea E (2017) Should we stop saying 'glia' and 'neuroinflammation'?Trends Mol Med 23:486-500.

Tronel C, et al. (2017) Molecular targets for PET imaging of activated microglia: The current situation and future expectations. Int J Mol Sci 18:E802.

Janssen B, Vugts D J, Windhorst A D, Mach R H (2018) PET imaging of microglial activation-beyond targeting TSPO. Molecules 23:607.

Aguzzi A, Barres B A, Bennett M L (2013) Microglia: Scapegoat, saboteur, or something else?Science 339:156-161.

Akiyama H, et al. (1994) Expression of the receptor for macrophage colony stimulating factor by brain microglia and its upregulation in brains of patients with Alzheimer's disease and amyotrophic lateral sclerosis. Brain Res 639: 171-174.

Zhang Y, et al. (2014) An RNA-sequencing transcriptome and splicing database of glia, neurons, and vascular cells of the cerebral cortex. J Neurosci 34:11929-11947.

Peyraud F, Cousin S, Italiano A (2017) CSF-1R inhibitor development: Current clinical status. Curr Oncol Rep 19:70.

Chitu V, Gokhan S, Nandi S, Mehler M F, Stanley E R (2016) Emerging roles for CSF-1 receptor and its ligands in the nervous system. Trends Neurosci 39:378-393.

Ginhoux F, et al. (2010) Fate mapping analysis reveals that adult microglia derive from primitive macrophages. Science 330:841-845.

Elmore M R, et al. (2014) Colony-stimulating factor 1 receptor signaling is necessary for microglia viability, unmasking a microglia progenitor cell in the adult brain. Neuron 82:380-397.

Walker D G, Tang T M, Lue L F (2017) Studies on colony stimulating factor receptor-1 and ligands colony stimulating factor-1 and interleukin-34 in Alzheimer's disease brains and human microglia. Front Aging Neurosci 9:244.

Smith A M, et al. (2013) M-CSF increases proliferation and phagocytosis while modulating receptor and transcription factor expression in adult human microglia. J Neuroinflammation 10:85.

Palle P, Monaghan K L, Milne S M, Wan E C K (2017) Cytokine signaling in multiple sclerosis and its therapeutic applications. Med Sci (Basel) 5:E0023.

El-Gamal M I, et al. (2018) Recent advances of colony-stimulating factor-1 receptor (CSF-1R) kinase and its inhibitors. J Med Chem 61:5450-5466.

Lue L F, et al. (2001) Inflammatory repertoire of Alzheimer's disease and nondemented elderly microglia in vitro. Glia 35:72-79.

Murphy G M Jr, Zhao F, Yang L, Cordell B (2000) Expression of macrophage colony-stimulating factor receptor is increased in the AbetaPP(V717F) transgenic mouse model of Alzheimer's disease. Am J Pathol 157:895-904.

Yan S D, et al. (1997) An intracellular protein that binds amyloid-beta peptide and mediates neurotoxicity in Alzheimer's disease. Nature 389:689-695.

Boissonneault V, et al. (2009) Powerful beneficial effects of macrophage colony-stimulating factor on beta-amyloid deposition and cognitive impairment in Alzheimer's disease. Brain 132:1078-1092.

Deczkowska A, et al. (2018) Disease-associated microglia: A universal immune sensor of neurodegeneration. Cell 173:1073-1081.

Keren-Shaul H, et al. (2017) A unique microglia type associated with restricting development of Alzheimer's disease. Cell 169:1276-1290.e17.

Raivich G, et al. (1998) Regulation of MCSF receptors on microglia in the normal and injured mouse central nervous system: A quantitative immunofluorescence study using confocal laser microscopy. J Comp Neurol 395:342-358.

Prieto-Morin C, Ayrignac X, Ellie E, Tournier-Lasserve E, Labauge P (2016) CSF1R-related leukoencephalopathy mimicking primary progressive multiple sclerosis. J Neurol 263:1864-1865.

Alterman R L, Stanley E R (1994) Colony stimulating factor-1 expression in human glioma. Mol Chem Neuropathol 21:177-188.

Lentz M R, et al. (2010) Exploring the relationship of macrophage colony-stimulating factor levels on neuroaxonal metabolism and cognition during chronic human immunodeficiency virus infection. J Neurovirol 16:368-376.

Bernard-Gauthier V, Schirrmacher R (2014) 5-(4-((4-[(18)F]Fluorobenzyl)oxy)-3-methoxybenzyl)pyrimidine-2,4-diamine: A selective dual inhibitor for potential PET imaging of Trk/CSF-1R. Bioorg Med Chem Lett 24:4784-4790.

Illig C R, et al. (2008) Discovery of novel FMS kinase inhibitors as anti-inflammatory agents. Bioorg Med Chem Lett 18:1642-1648.

Krauser J A, et al. (2015) Phenotypic and metabolic investigation of a CSF-1R kinase receptor inhibitor (BLZ945) and its pharmacologically active metabolite. Xenobiotica 45:107-123.

DeNardo D G, et al. (2011) Leukocyte complexity predicts breast cancer survival and functionally regulates response to chemotherapy. Cancer Discov 1:54-67.

Melnikova T, et al. (2013) Reversible pathologic and cognitive phenotypes in an inducible model of Alzheimer-amyloidosis. J Neurosci 33:3765-3779.

Dobos N, et al. (2012) The role of indoleamine 2,3-dioxygenase in a mouse model of neuroinflammation-induced depression. J Alzheimers Dis 28:905-915.

Qin L, et al. (2007) Systemic LPS causes chronic neuroinflammation and progressive neurodegeneration. Glia 55:453-462.

Jones M V, et al. (2008) Behavioral and pathological outcomes in MOG 35-55 experimental autoimmune encephalomyelitis. J Neuroimmunol 199:83-93.

Catorce M N, Gevorkian G (2016) LPS-induced murine neuroinflammation model: Main features and suitability for pre-clinical assessment of nutraceuticals. Curr Neuropharmacol 14:155-164.

Nandi S, et al. (2012) The CSF-1 receptor ligands IL-34 and CSF-1 exhibit distinct developmental brain expression patterns and regulate neural progenitor cell maintenance and maturation. Dev Biol 367:100-113.

Michaelson M D, et al. (1996) CSF-1 deficiency in mice results in abnormal brain development. Development 122:2661-2672.

Lee S C, et al. (1993) Macrophage colony-stimulating factor in human fetal astrocytes and microglia. Differential regulation by cytokines and lipopolysaccharide, and modulation of class II MHC on microglia. J Immunol 150:594-604.

Aid S, Parikh N, Palumbo S, Bosetti F (2010) Neuronal overexpression of cyclooxygenase-2 does not alter the neuroinflammatory response during brain innate immune activation. Neurosci Lett 478:113-118.

Dickens A M, et al. (2014) Detection of microglial activation in an acute model of neuroinflammation using PET and radiotracers $^{11}$C—(R)—PK11195 and 18F-GE-180. J Nucl Med 55:466-472.

5. Federal Register § 361.1 (2018), pp 21378-21381.

Hannestad J, et al. (2012) Endotoxin-induced systemic inflammation activates microglia: [$^{11}$C]PBR28 positron emission tomography in nonhuman primates. Neuroimage 63:232-239.

Heppner F L, Ransohoff R M, Becher B (2015) Immune attack: The role of inflammation in Alzheimer disease. Nat Rev Neurosci 16:358-372.

Hickman S E, El Khoury J (2014) TREM2 and the neuroimmunology of Alzheimer's disease. Biochem Pharmacol 88:495-498.

Stabin M G, Sparks R B, & Crowe E (2005) OLINDA/EXM: the second-generation personal computer software for internal dose assessment in nuclear medicine. J. Nucl. Med. 46(6):1023-1027.

Foster D M (1998) Developing and testing integrated multicompartment models to describe a single-input multiple-output study using the SAAM II software system. Adv Exp Med Biol 445:59-78.

Stabin M G & Siegel J A (2003) Physical models and dose factors for use in internal dose assessment. Health Phys. 85(3):294-310.

Beeton C, Garcia A, & Chandy K G (2007) Induction and clinical scoring of chronic-relapsing experimental autoimmune encephalomyelitis. J Vis Exp (5):224.

Horti A G, et al. (2016) 18F-FNDP for PET Imaging of Soluble Epoxide Hydrolase. J. Nucl. Med. 57(11):1817-1822.

Rahmim A, Cheng J C, Blinder S, Camborde M L, & Sossi V (2005) Statistical dynamic image reconstruction in state-of-the-art high-resolution PET. Phys. Med. Biol. 50(20):4887-4912.

Logan J, et al. (1990) Graphical analysis of reversible radioligand binding from time-activity measurements applied to [N-11C-methyl]-(−)-cocaine PET studies in human subjects. J. Cereb. Blood Flow Metab. 10(5):740-747.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula:

(1k)

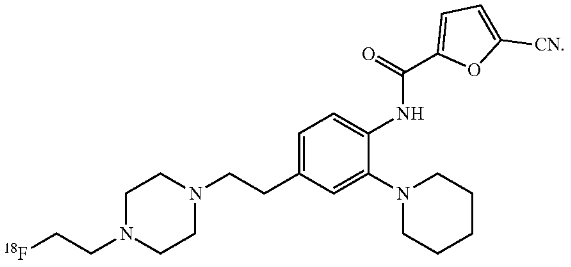

2. A method for imaging macrophage colony stimulating factor receptor (CSF1R) in a subject afflicted or suspected of being afflicted with one or more neuroinflammatory or neurodegenerative diseases or conditions, the method comprising administering to the subject an effective amount of a compound of claim 1, or a pharmaceutically acceptable salt thereof and taking a PET image.

3. The method of claim 2, wherein the neuroinflammatory or neurodegenerative disease or condition is selected from the group consisting of Alzheimer's disease (AD), multiple sclerosis (MS), a traumatic brain injury, a brain tumor, HIV-associated cognitive impairment, and one or more demyelinating diseases.

* * * * *